US010538768B2

(12) United States Patent
Jaschinski et al.

(10) Patent No.: US 10,538,768 B2
(45) Date of Patent: Jan. 21, 2020

(54) MODIFIED TGF-BETA OLIGONUCLEOTIDES

(71) Applicant: ISARNA THERAPEUTICS GMBH, München (DE)

(72) Inventors: Frank Jaschinski, Puchheim (DE); Michel Janicot, Brussels (BE); Eugen Uhlmann, Glashütten (DE)

(73) Assignee: ISARNA THERAPEUTICS GMBH, München (DE)

( * ) Notice: Subject to any disclaimer, the term of this patent is extended or adjusted under 35 U.S.C. 154(b) by 0 days.

(21) Appl. No.: 15/882,221

(22) Filed: Jan. 29, 2018

(65) Prior Publication Data

US 2018/0230473 A1 Aug. 16, 2018

Related U.S. Application Data

(62) Division of application No. 14/780,043, filed as application No. PCT/EP2014/056221 on Mar. 27, 2014, now Pat. No. 9,926,563.

(30) Foreign Application Priority Data

Mar. 27, 2013 (EP) .................................... 13161474
Jun. 20, 2013 (EP) .................................... 13173078
Dec. 30, 2013 (EP) .................................... 13199826

(51) Int. Cl.
*C12N 15/113* (2010.01)

(52) U.S. Cl.
CPC ...... *C12N 15/1136* (2013.01); *C12N 2310/11* (2013.01); *C12N 2310/3231* (2013.01); *C12N 2310/341* (2013.01); *C12N 2310/351* (2013.01)

(58) Field of Classification Search
None
See application file for complete search history.

(56) References Cited

U.S. PATENT DOCUMENTS

2004/0006030 A1 1/2004 Monia
2011/0136893 A1 6/2011 Schlingensiepen
2015/0099791 A1 4/2015 Krieg et al.

FOREIGN PATENT DOCUMENTS

EP 1008649 A2 6/2000
EP 2399611 A2 12/2011
EP 2453017 A1 5/2012
WO 1994025588 A2 11/1994
WO 2004005552 A1 1/2004
WO 2005084712 A2 9/2005
WO 2011154542 A1 12/2011

OTHER PUBLICATIONS

Stanton, Robert, et al., "Chemical Modification Study of Antisense Gapmers," Nucleic Acid Therapeutics, Oct. 2012, pp. 344-359, vol. 22, No. 5.
Gordon, Kelly J., et al., "Role of transforming growth factor-beta superfamily signaling pathways in human disease," Biochimica Et Biophysica Acta, Molecular Basis of Disease, Feb. 11, 2008, pp. 197-228, vol. 1782, No. 4.
Takagi-Sato, Miho, et al., "Design of ENA® gapmers as tine-tuning antisense oligonucleotides with sequence-specific inhibitory activity on mouse PADI4 mRNA expression," Nucleic Acids Symposium Series, 2006, pp. 319-320, No. 50.
Prendes, Mark A., et al., "The role of transforming growth factor beta in glaucoma and the therapeutic implications," British Journal of Ophthalmology, Jan. 15, 2013, pp. 680-686, vol. 97, No. 6.

*Primary Examiner* — J. E. Angell
(74) *Attorney, Agent, or Firm* — Gianna J. Arnold; Saul Ewing Arnstein & Lehr LLP

(57) ABSTRACT

The invention refers to an oligonucleotide consisting of 10 to 20 nucleotides of selected regions of the TGF-beta1, TGF-beta2 or TGF-beta3 nucleic acid sequence, which comprises modified nucleotides such as LNA, ENA, polyalkylene oxide-, 2'-fluoro, 2'-O-methoxy and/or 2'-O-methyl modified nucleotides. The selected regions are preferably the region of nucleic acid no. 1380 to 1510, no. 1660 to 1680, no. 2390 to 2410, or no. 2740 to 2810 of the TGF-beta2 nucleic acid sequence of SEQ ID NO. 1, specific regions of the TGF-beta1 nucleic acid sequence of SEQ ID NO. 149, or specific regions of the TGF-beta3 nucleic acid sequence of SEQ ID No. 267. The invention further relates to pharmaceutical compositions comprising such oligonucleotide, wherein the composition or the oligonucleotide is used in the prevention and/or treatment of a malignant and/or benign tumor, an immunologic disease, fibrosis, glaucoma, etc.

5 Claims, 67 Drawing Sheets

Specification includes a Sequence Listing.

FIG. 1: Nucleotide modifications
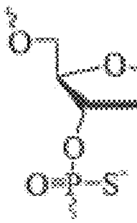
Phosphorthioate
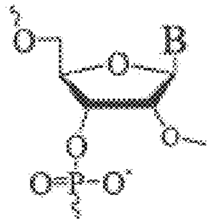
2'-O-Methyl
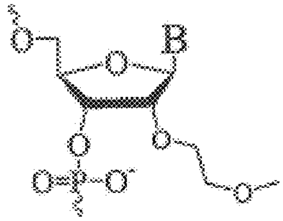
2'-MOE
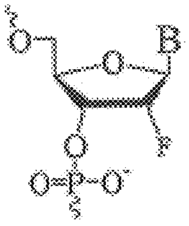
2'-Fluoro
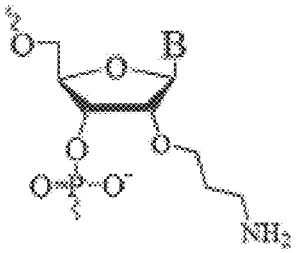
2'-AP
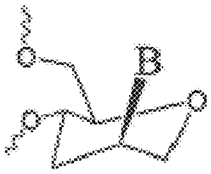
HNA
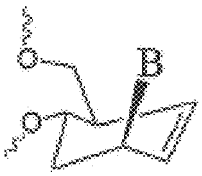
CeNA
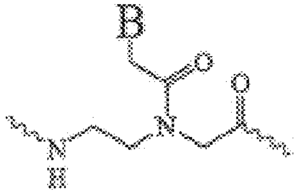
PNA
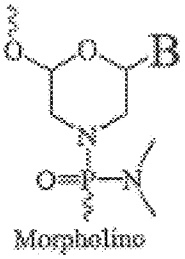
Morpholino
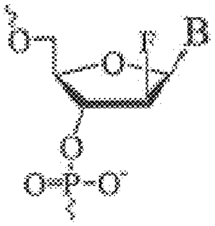
2'-F-ANA
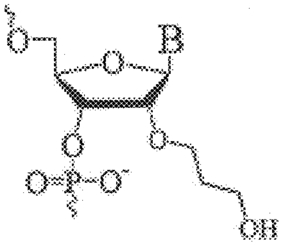
2'-(3-hydroxy)propyl
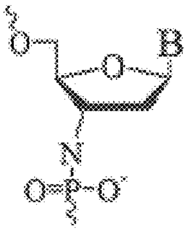
3'-Phosphoramidate
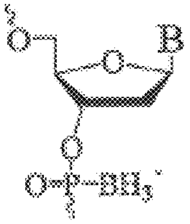
Boranophosphates

FIG. 2a: Nucleic acid sequence of human TGF-beta 2 (SEQ ID NO. 1)

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctggaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggcccctgcg gcacccgacc gagtaccgag
 661 cgccctgcga agcgcaccct cctccccgcg gtgcgctggg ctcgccccca gcgcgcgcac
 721 acgcacacac acacacacac acacacacgc acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgcccctccc gtcagttcgc cagctgccag ccccgggacc ttttcatctc ttccctttttg
 961 gccggaggag ccgagttcag atccgccact ccgcacccga gactgacaca ctgaactcca
1021 cttcctcctc ttaaatttat ttctacttaa tagccactcg tctctttttt tccccatctc
1081 attgctccaa gaattttttt cttcttactc gccaaagtca gggttccctc tgcccgtccc
1141 gtattaatat ttccactttt ggaactactg gccttttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaacttttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtccccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttcccctcc gaaaatgcca tcccgcccac tttctacaga
1741 ccctacttca gaattgttcg atttgacgtc tcagcaatgg agaagaatgc ttccaatttg
1801 gtgaaagcag agttcagagt ctttcgtttg cagaacccaa aagccagagt gcctgaacaa
1861 cggattgagc tatatcagat tctcaagtcc aaagatttaa catctccaac ccagcgctac
1921 atcgacagca aagttgtgaa aacaagagca gaaggcgaat ggctctcctt cgatgtaact
1981 gatgctgttc atgaatggct tcaccataaa gacaggaacc tgggatttaa aataagctta
2041 cactgtccct gctgcacttt tgtaccatct aataattaca tcatcccaaa taaaagtgaa
2101 gaactagaag caagatttgc aggtattgat ggcacctcca catataccag tggtgatcag
2161 aaaactataa agtccactag gaaaaaaaac agtgggaaga ccccacatct cctgctaatg
2221 ttattgccct cctacagact tgagtcacaa cagaccaacc ggcggaagaa gcgtgctttg
2281 gatgcggcct attgctttag aaatgtgcag gataattgct gcctacgtcc actttacatt
2341 gatttcaaga gggatctagg gtggaaatgg atacacgaac ccaaagggta caatgccaac
2401 ttctgtgctg gagcatgccc gtatttatgg agttcagaca ctcagcacag cagggtcctg
2461 agcttatata ataccataaa tccagaagca tctgcttctc cttgctgcgt gtcccaagat
2521 ttagaacctc taaccattct ctactacatt ggcaaaacac ccaagattga acagctttct
2581 aatatgattg taaagtcttg caaatgcagc taaaattctt ggaaaagtgg caagaccaaa
2641 atgacaatga tgatgataat gatgatgacg acgacaacga tgatgcttgt aacaagaaaa
2701 cataagagag ccttggttca tcagtgttaa aaaatttttg aaaaggcggt actagttcag
2761 acactttgga agtttgtgtt ctgtttgtta aaactggcat ctgacacaaa aaaagttgaa
2821 ggccttattc tacatttcac ctactttgta agtgagagag acaagaagca aatttttttt
2881 aaagaaaaaa ataaacactg gaagaattta ttagtgttaa ttatgtgaac aacgacaaca
2941 acaacaacaa caacaaacag gaaaatccca ttaagtggag ttgctgtacg taccgttcct
3001 atcccgcgcc tcacttgatt tttctgtatt gctatgcaat aggcaccctt cccattctta
3061 ctcttagagt taacagtgag ttatttattg tgtgttacta tataatgaac gtttcattgc
3121 ccttggaaaa taaaacaggt gtataaagtg gagaccaaat actttgccag aaactcatgg
3181 atggcttaag gaacttgaac tcaaacgagc cagaaaaaaa gaggtcatat taatgggatg
3241 aaaacccaag tgagttatta tatgaccgag aaagtctgca ttaagataaa gaccctgaaa
3301 acacatgtta tgtatcagct gcctaaggaa gcttcttgta aggtccaaaa actaaaaaga
```

FIG. 2b

```
3361 ctgttaataa aagaaacttt cagtcagaat aagtctgtaa gttttttttt ttctttttaa
3421 ttgtaaatgg ttctttgtca gtttagtaaa ccagtgaaat gttgaaatgt tttgacatgt
3481 actggtcaaa cttcagacct taaaatattg ctgtatagct atgctatagg tttttttcctt
3541 tgttttggta tatgtaacca tacctatatt attaaaatag atggatatag aagccagcat
3601 aattgaaaac acatctgcag atctcttttg caaactatta aatcaaaaca ttaactactt
3661 tatgtgtaat gtgtaaattt ttaccatatt ttttatattc tgtaataatg tcaactatga
3721 tttagattga cttaaatttg ggctcttttt aatgatcact cacaaatgta tgtttctttt
3781 agctggccag tacttttgag taaagcccct atagtttgac ttgcactaca aatgcatttt
3841 tttttttaata acatttgccc tacttgtgct ttgtgtttct ttcattatta tgacataagc
3901 tacctgggtc cacttgtctt ttcttttttt tgtttcacag aaaagatggg ttcgagttca
3961 gtggtcttca tcttccaagc atcattacta accaagtcag acgttaacaa atttttatgt
4021 taggaaaagg aggaatgtta tagatacata gaaaattgaa gtaaaatgtt ttcattttag
4081 caaggattta gggttctaac taaaactcag aatctttatt gagttaagaa aagtttctct
4141 accttggttt aatcaatatt tttgtaaaat cctattgtta ttacaaagag gacacttcat
4201 aggaaacatc tttttcttta gtcaggtttt taatattcag gggaaattg aaagatatat
4261 attttagtcg atttttcaaa aggggaaaaa agtccaggtc agcataagtc attttgtgta
4321 tttcactgaa gttataaggt ttttataaat gttctttgaa ggggaaaagg cacaagccaa
4381 tttttcctat gatcaaaaaa ttctttcttt cctctgagtg agagttatct atatctgagg
4441 ctaaagttta ccttgcttta ataaataatt tgccacatca ttgcagaaga ggtatcctca
4501 tgctggggtt aatagaatat gtcagtttat cacttgtcgc ttatttagct ttaaaataaa
4561 aattaatagg caaagcaatg gaatatttgc agtttcacct aaagagcagc ataaggaggc
4621 gggaatccaa agtgaagttg tttgatatgg tctacttctt ttttggaatt tcctgaccat
4681 taattaaaga attggatttg caagtttgaa aactggaaaa gcaagagatg ggatgccata
4741 atagtaaaca gcccttgtgt tggatgtaac ccaatcccag atttgagtgt gtgttgatta
4801 tttttttgtc ttccactttt ctattatgtg taaatcactt ttatttctgc agacattttc
4861 ctctcagata ggatgacatt ttgttttgta ttattttgtc tttcctcatg aatgcactga
4921 taatatttta aatgctctat tttaagatct cttgaatctg tttttttttt ttttaatttg
4981 ggggttctgt aaggtcttta tttcccataa gtaaatattg ccatgggagg ggggtggagg
5041 tggcaaggaa ggggtgaagt gctagtatgc aagtgggcag caattatttt tgtgttaatc
5101 agcagtacaa tttgatcgtt ggcatggtta aaaaatggaa tataagatta gctgttttgt
5161 attttgatga ccaattacgc tgtattttaa cacgatgtat gtctgttttt gtggtgctct
5221 agtggtaaat aaattatttc gatgatatgt ggatgtcttt ttcctatcag taccatcatc
5281 gagtctagaa aacacctgtg atgcaataag actatctcaa gctggaaaag tcataccacc
5341 tttccgattg ccctctgtgc tttctccctt aaggacagtc acttcagaag tcatgcttta
5401 aagcacaaga gtcaggccat atccatcaag gatagaagaa atccctgtgc cgtcttttta
5461 ttcccttatt tattgctatt tggtaattgt ttgagattta gtttccatcc agcttgactg
5521 ccgaccagaa aaaatgcaga gagatgtttg caccatgctt tggctttctg gttctatgtt
5581 ctgccaacgc cagggccaaa agaactggtc tagacagtat cccctgtagc cccataactt
5641 ggatagttgc tgagccagcc agatataaca agagccacgt gctttctggg gttggttgtt
5701 tgggatcagc tacttgcctg tcagtttcac tggtaccact gcaccacaaa caaaaaaacc
5761 caccctattt cctccaattt ttttggctgc tacctacaag accagactcc tcaaacgagt
5821 tgccaatctc ttaataaata ggattaataa aaaaagtaat tgtgactcaa aaaaaaaaaa
5881 aa
```

FIG. 3a(ii)
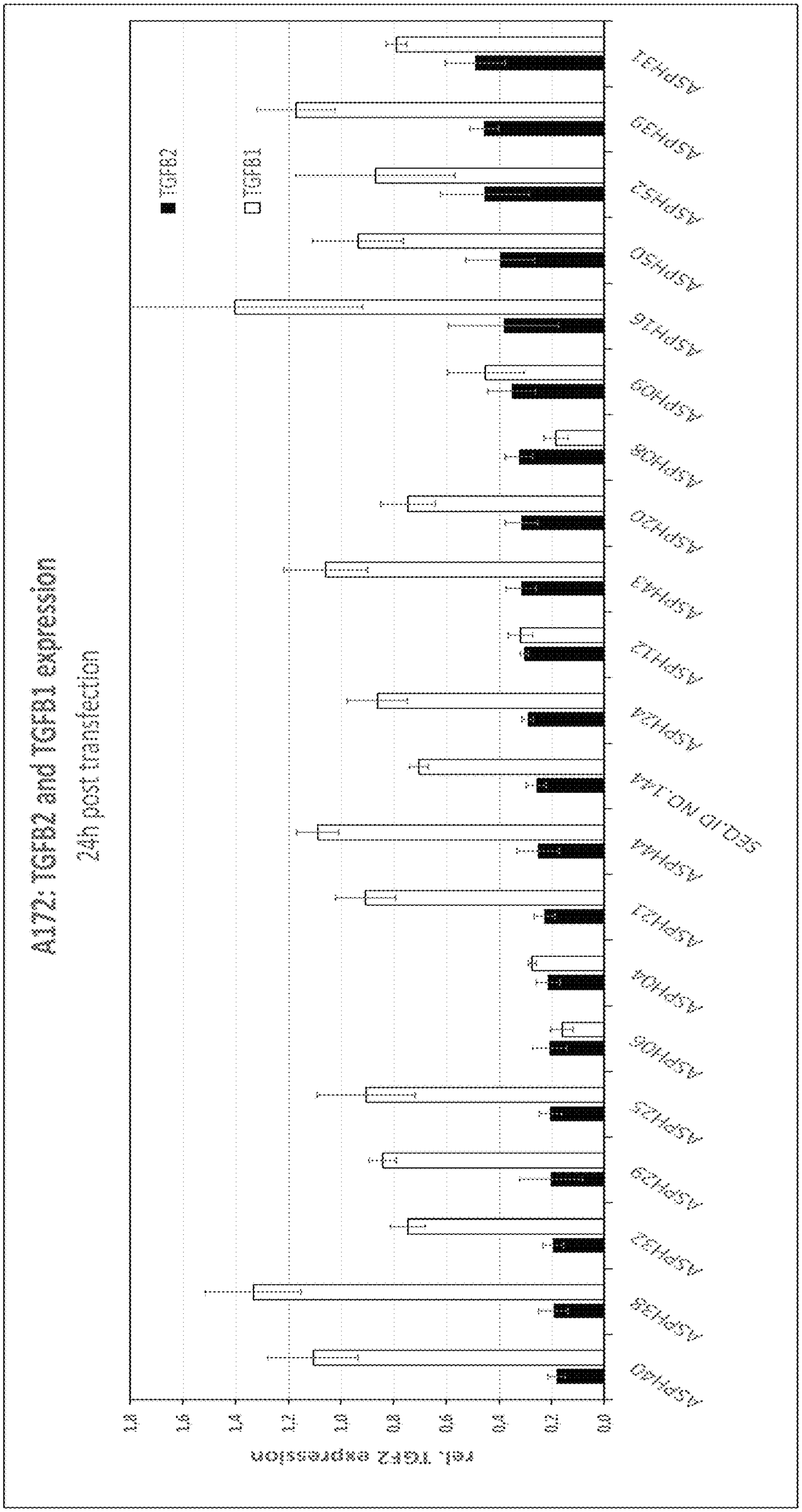

FIG. 3a(iii)
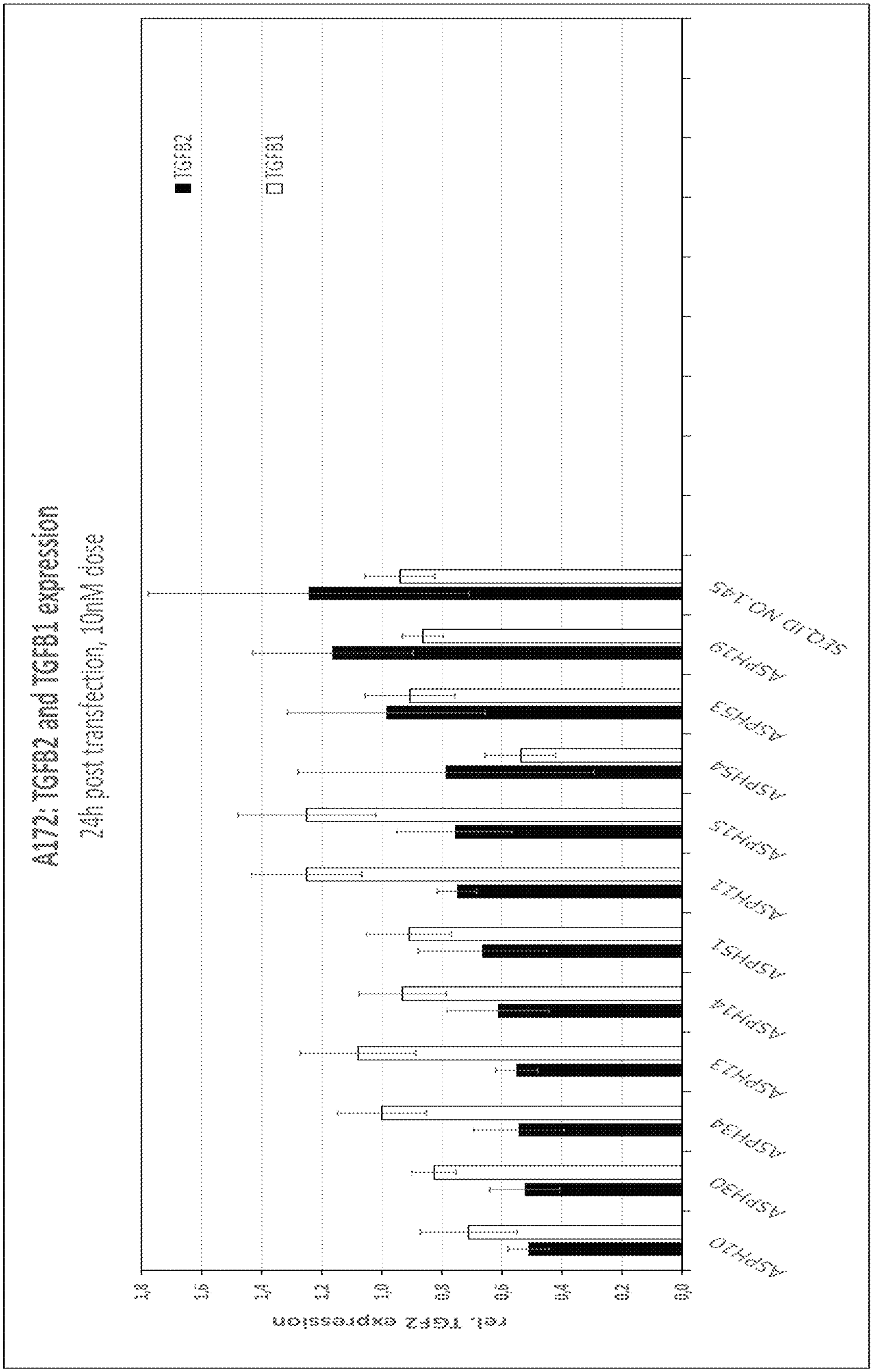

FIG. 3b(ii)
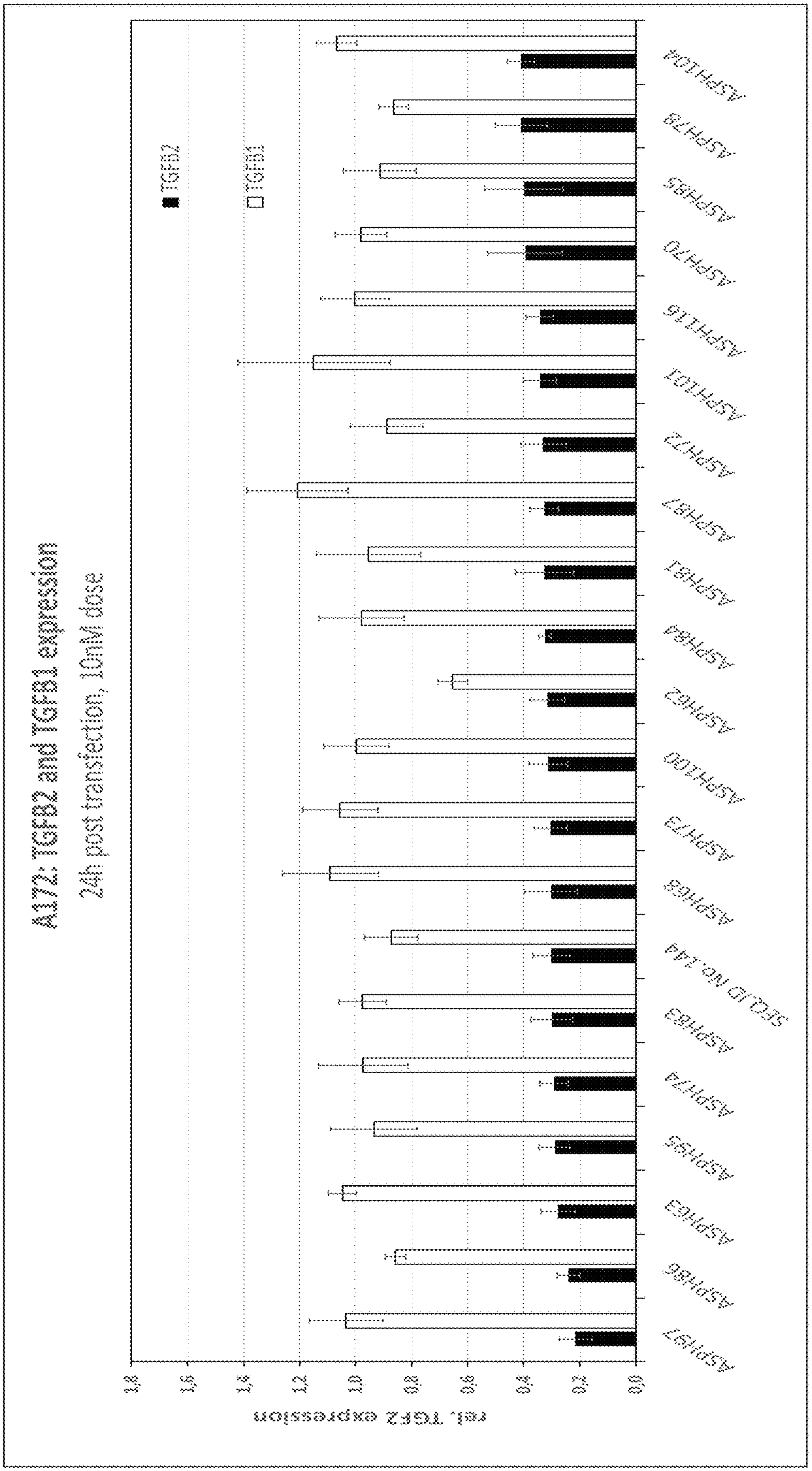

FIG. 3b(iii)
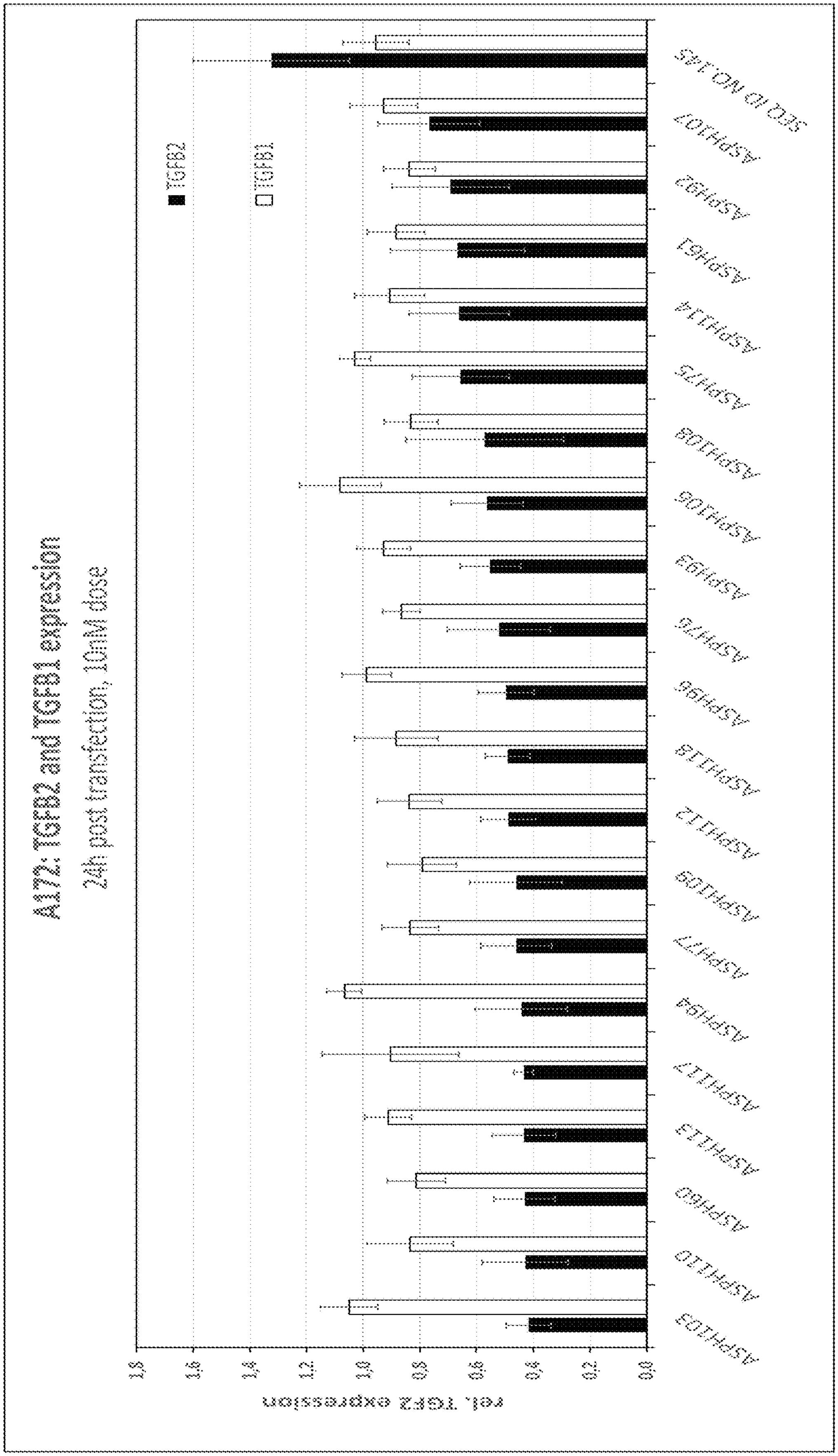

FIG. 3c(ii)
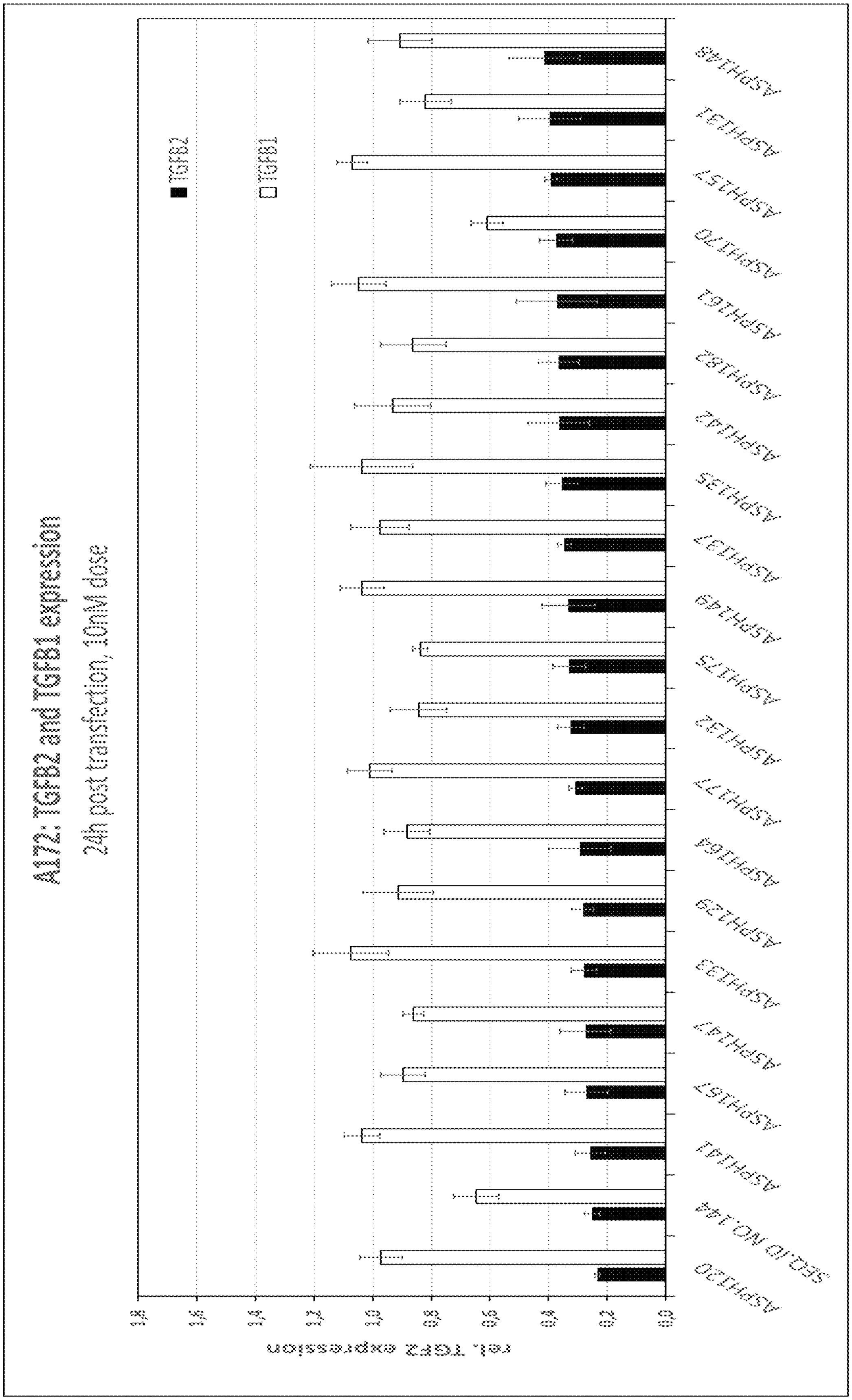

FIG. 3c(iii)
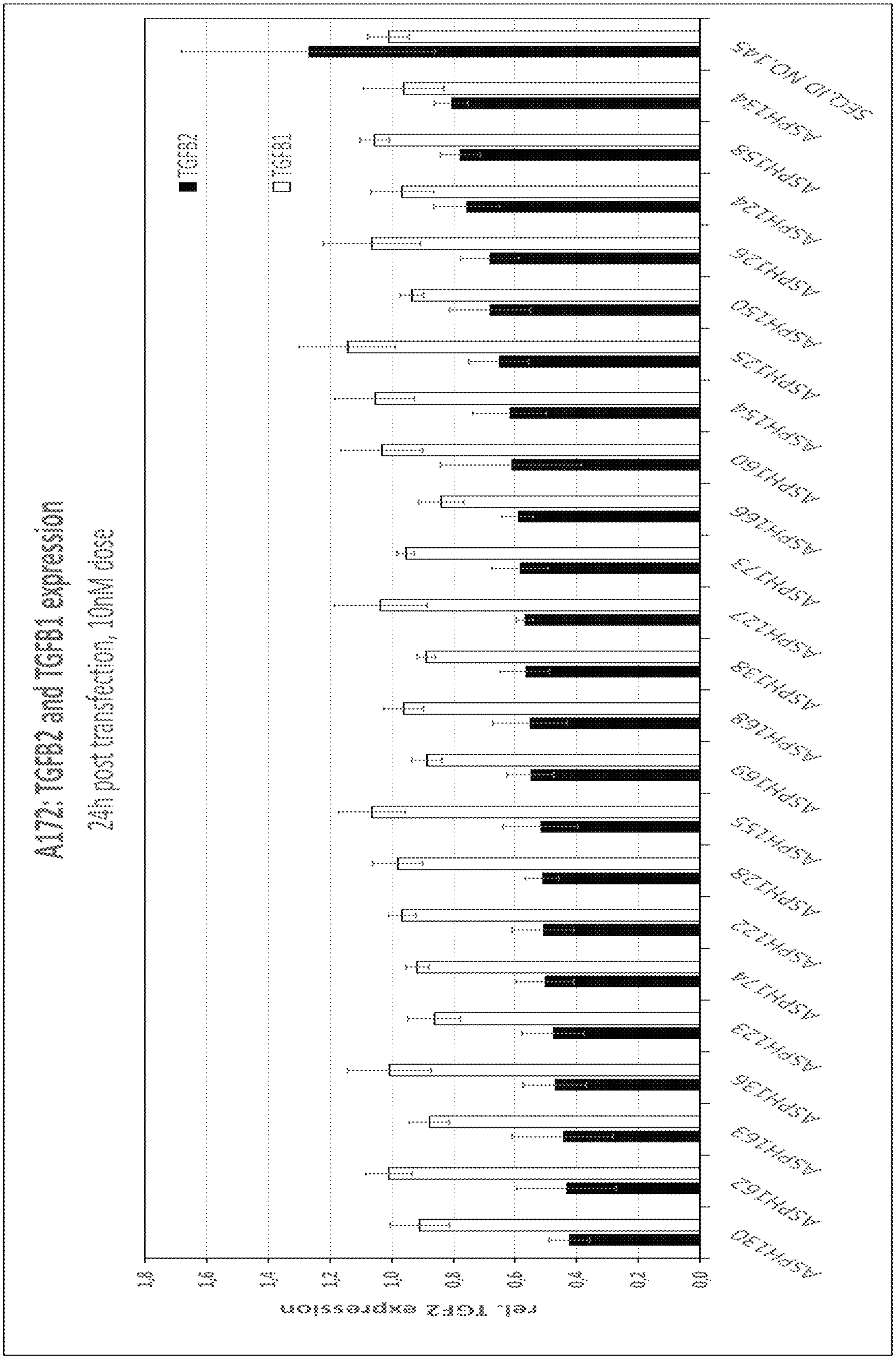

FIG. 4a(ii)
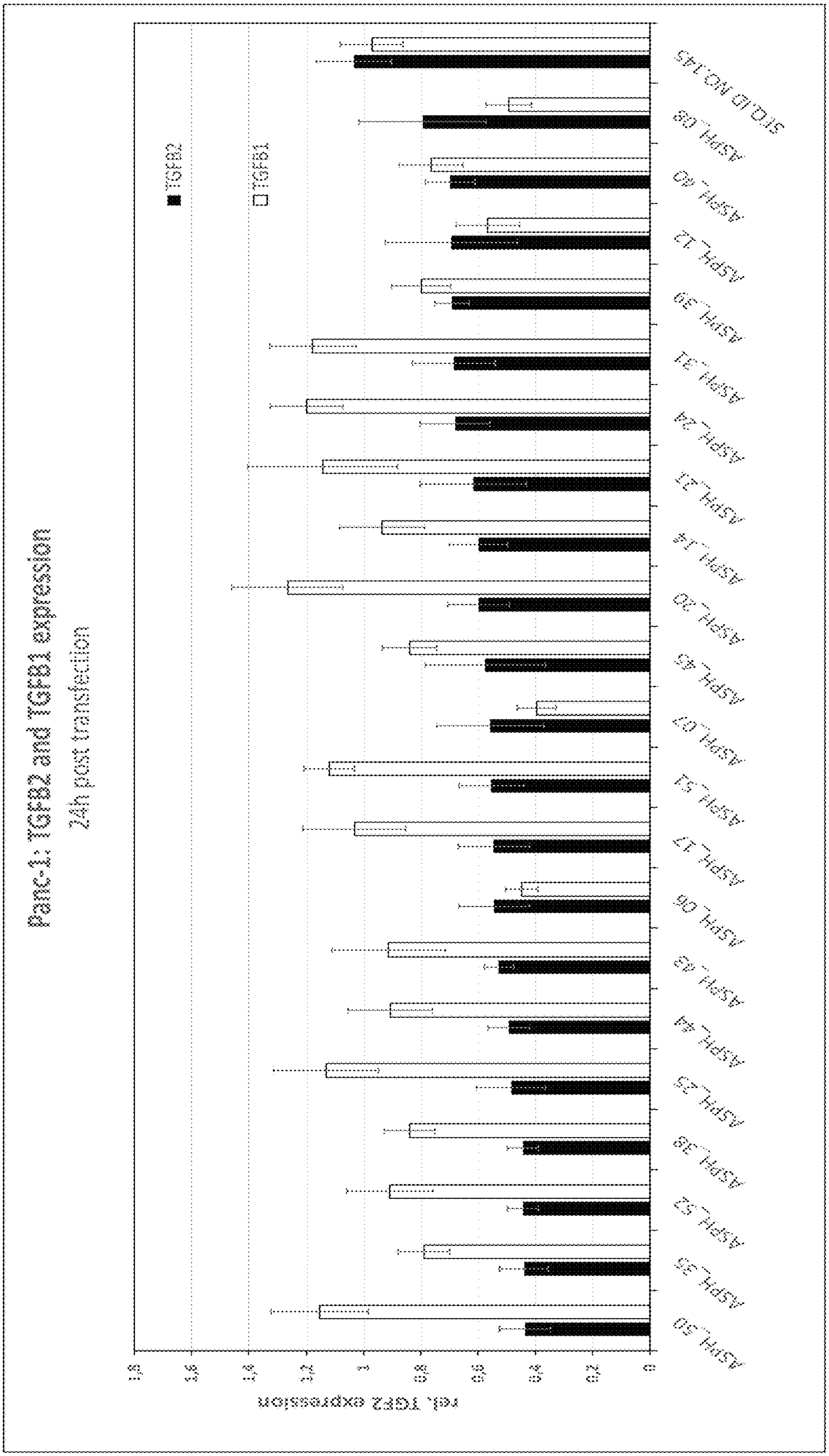

FIG. 4b(ii)
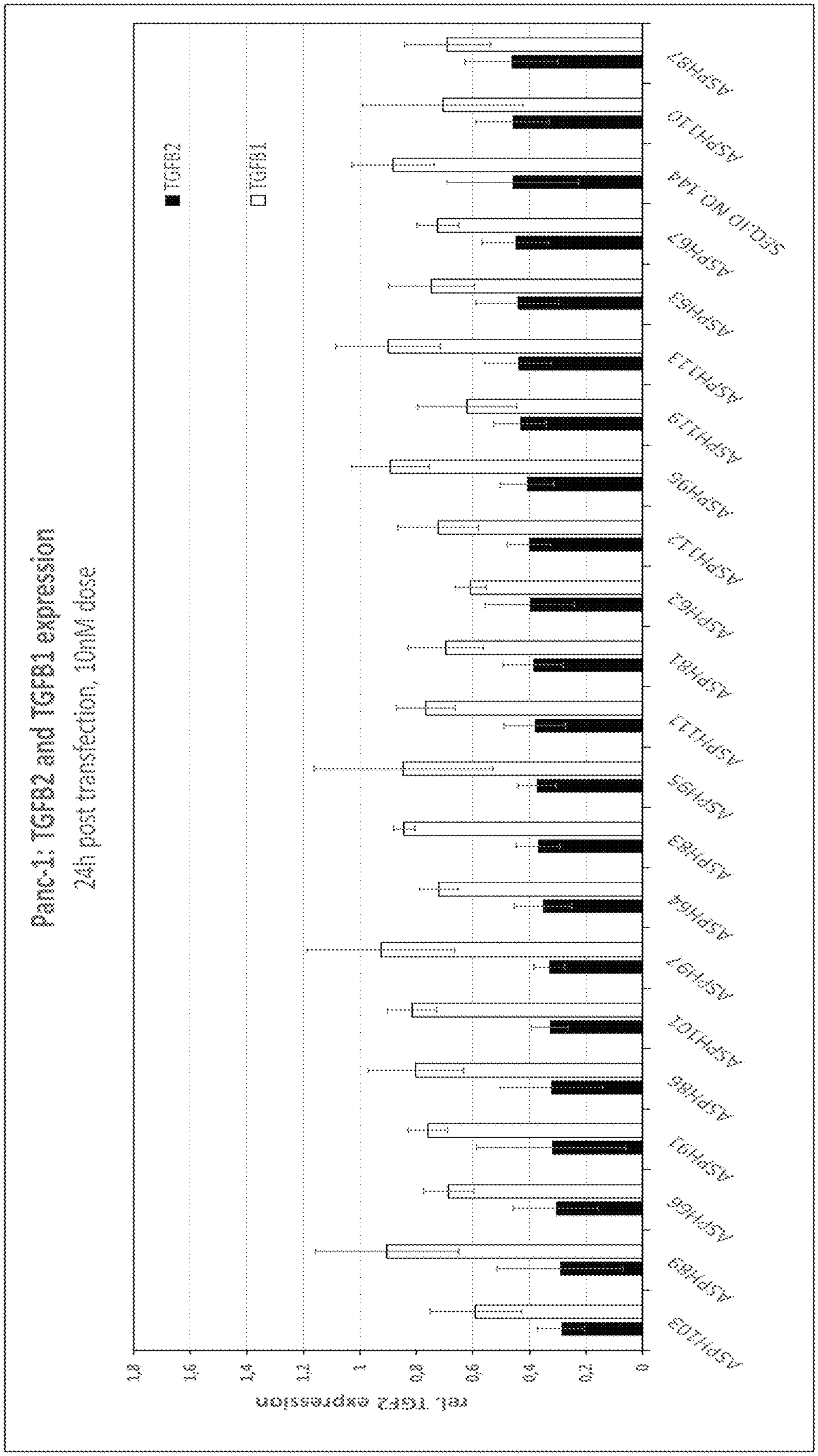

FIG. 4b(iii)
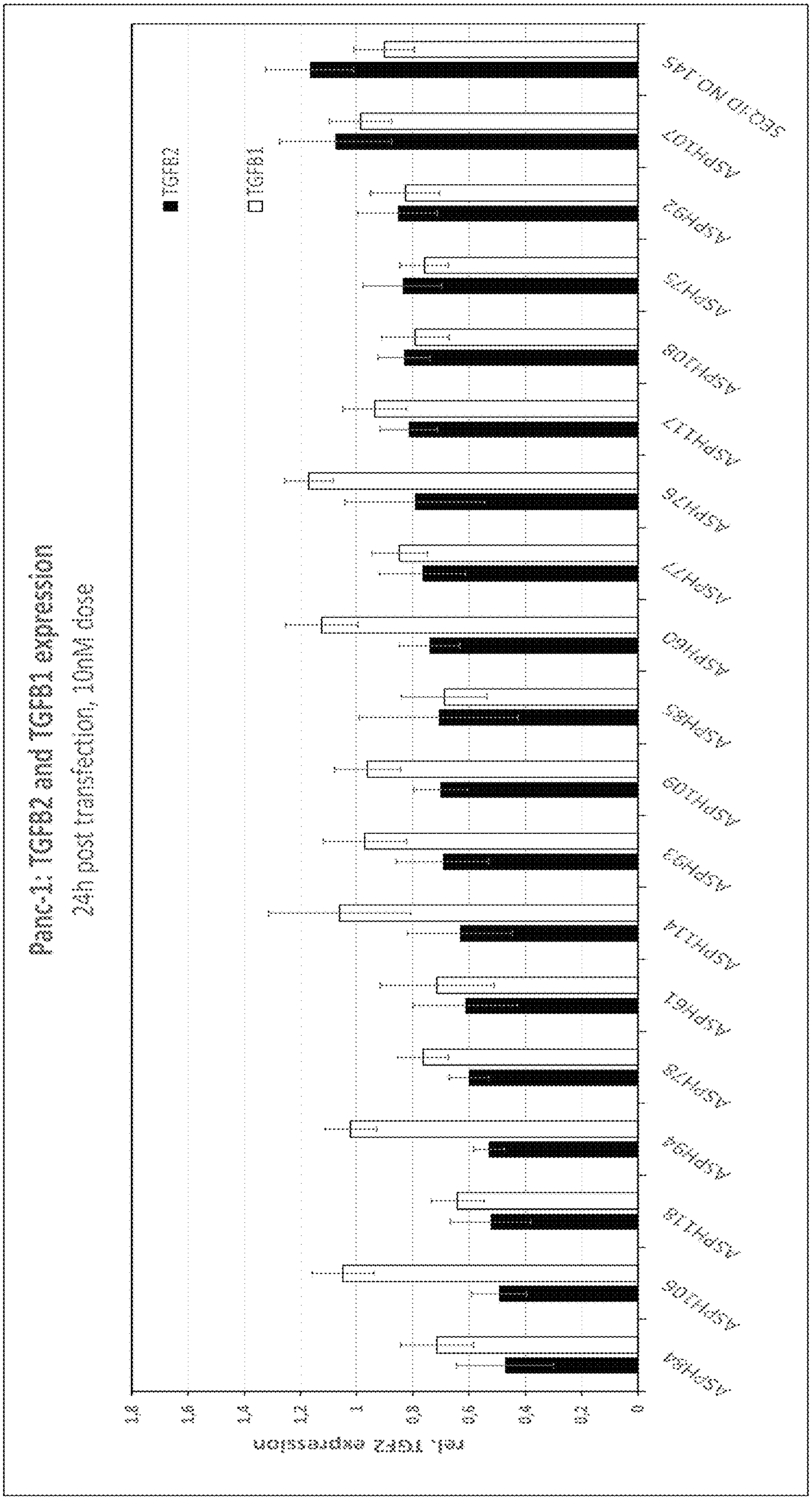

FIG. 4c(ii)
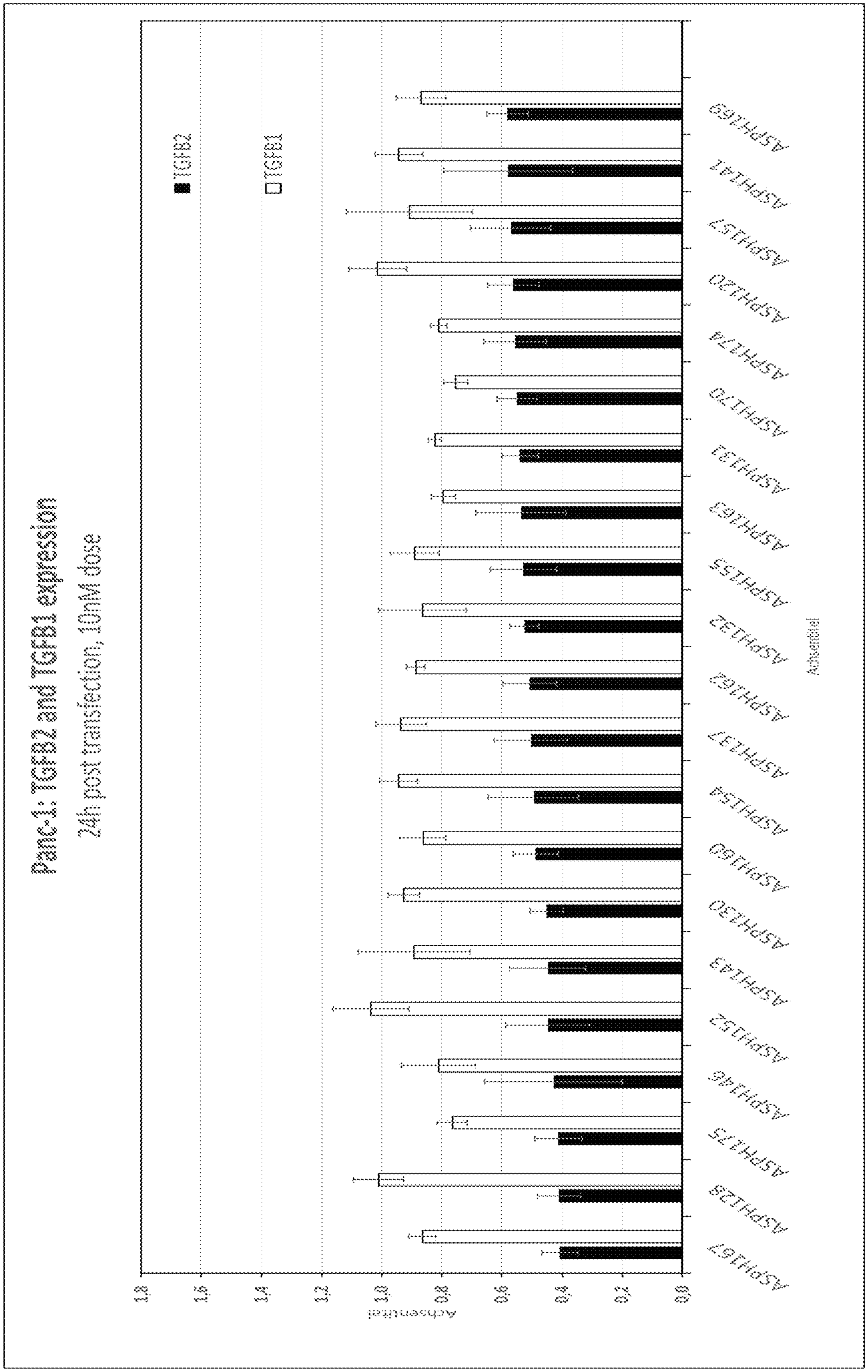

FIG. 4c(iii)
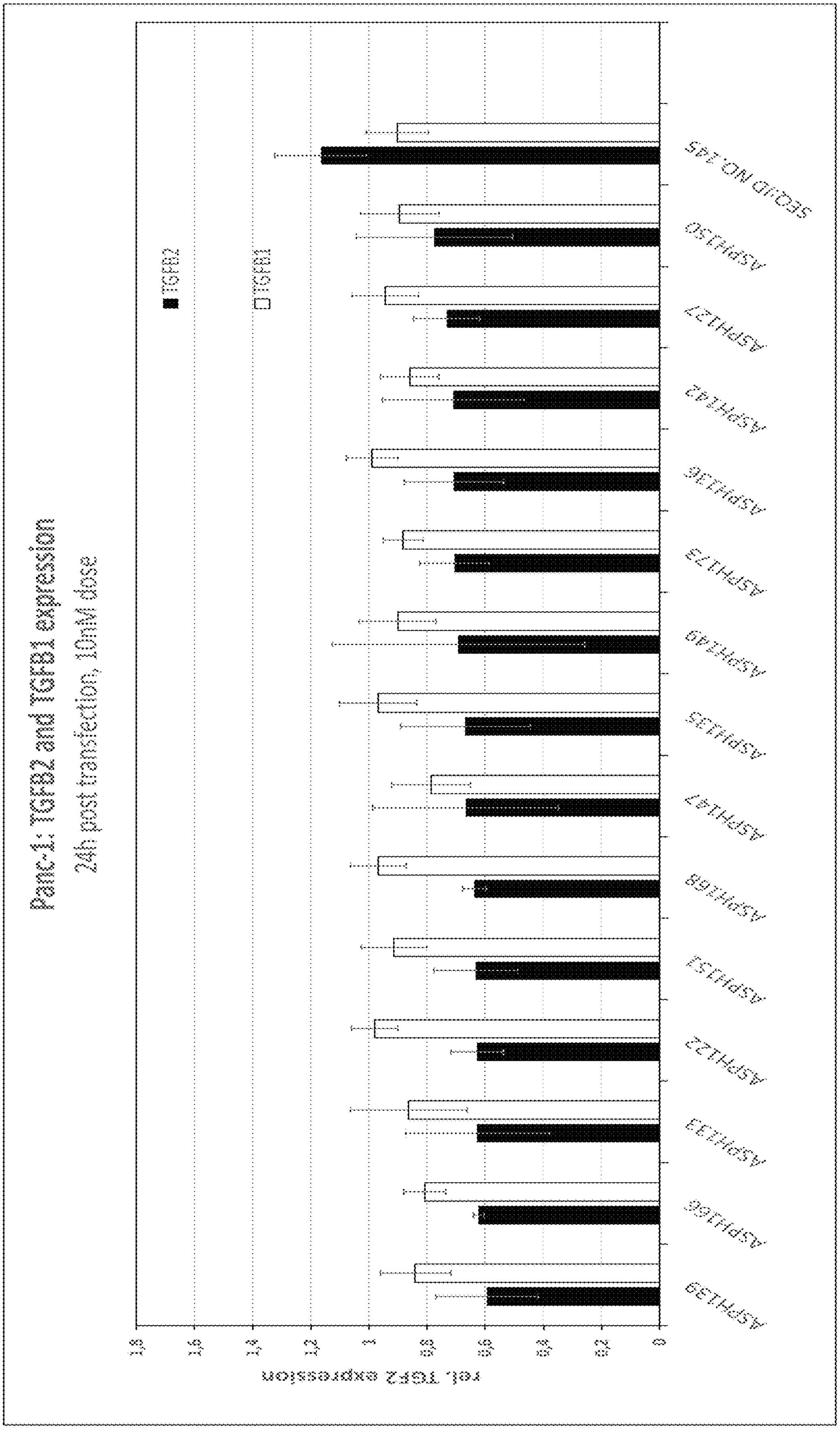

TGF-β2 and TGF-β1 mRNA expression in SMA-560 mouse cells
24h after transfection

FIG. 12: Nucleic acid sequence of human TGF-beta1 (SEQ ID No. 149)
Human TGF-beta 1 mRNA (NCBI Reference Sequence: NM_000660.4)
ORIGIN

```
   1 ccccgccgcc gccgcccttc gcgccctggg ccatctccct cccacctccc tccgcggagc
  61 agccagacag cgagggcccc ggccgggggc agggggggacg ccccgtccgg ggcacccccc
 121 cggctctgag ccgcccgcgg ggccggcctc ggcccggagc ggaggaagga gtcgccgagg
 181 agcagcctga ggccccagag tctgagacga gccgccgccg cccccgccac tgcggggagg
 241 aggggggagga ggagcgggag gagggacgag ctggtcggga gaagaggaaa aaaacttttg
 301 agacttttcc gttgccgctg ggagccggag gcgcggggac ctcttggcgc gacgctgccc
 361 cgcgaggagg caggacttgg ggaccccaga ccgcctccct ttgccgccgg ggacgcttgc
 421 tccctccctg cccccctacac ggcgtccctc aggcgccccc attccggacc agccctcggg
 481 agtcgccgac ccggcctccc gcaaagactt ttccccagac ctcgggcgca ccccctgcac
 541 gccgccttca tccccggcct gtctcctgag cccccgcgca tcctagaccc tttctcctcc
 601 aggagacgga tctctctccg acctgccaca gatcccctat tcaagaccac ccaccttctg
 661 gtaccagatc gcgcccatct aggttatttc cgtgggatac tgagacaccc ccggtccaag
 721 cctcccctcc accactgcgc ccttctccct gaggacctca gctttccctc gaggccctcc
 781 taccttttgc cgggagaccc ccagcccctg caggggcggg gcctccccac cacaccagcc
 841 ctgttcgcgc tctcggcagt gccgggggggc gccgcctccc ccatgccgcc ctccgggctg
 901 cggctgctgc cgctgctgct accgctgctg tggctactgg tgctgacgcc tggccggccg
 961 gccgcgggac tatccacctg caagactatc gacatggagc tggtgaagcg gaagcgcatc
1021 gaggccatcc gcggccagat cctgtccaag ctgcggctcg ccagcccccc gagccagggg
1081 gaggtgccgc ccggcccgct gccgcgaggcc gtgctcgccc tgtacaacag cacccgcgac
1141 cgggtggccg gggagagtgc agaaccggag cccgagcctg aggccgacta ctacgccaag
1201 gaggtcaccc gcgtgctaat ggtggaaacc cacaacgaaa tctatgacaa gttcaagcag
1261 agtacacaca gcatatatat gttcttcaac acatcagagc tccgagaagc ggtacctgaa
1321 cccgtgttgc tctcccgggc agagctgcgt ctgctgaggc tcaagttaaa agtggagcag
1381 cacgtggagc tgtaccagaa atacagcaac aattcctggc gatacctcag caaccggctg
1441 ctggcaccca gcgactcgcc agagtggtta tcttttgatg tcaccggagt tgtgcggcag
1501 tggttgagcc gtggaggggga aattgagggc tttcgcctta gcgcccactg ctcctgtgac
1561 agcagggata acacactgca agtggacatc aacgggttca ctaccggccg ccgaggtgac
1621 ctggccacca ttcatggcat gaaccggcct ttcctgcttc tcatggccac ccccgctggag
1681 agggcccagc atctgcaaag ctcccggcac cgccgagccc tggacaccaa ctattgcttc
1741 agctccacgg agaagaactg ctgcgtgcgg cagctgtaca ttgacttccg caaggacctc
1801 ggctggaagt ggatccacga gcccaagggc taccatgcca acttctgcct cgggccctgc
1861 ccctacattt ggagcctgga cacgcagtac agcaaggtcc tggccctgta caaccagcat
1921 aacccgggcg cctcggcggc gccgtgctgc gtgccgcagg cgctggagcc gctgcccatc
1981 gtgtactacg tgggccgcaa gcccaaggtg gagcagctgt ccaacatgat cgtgcgctcc
2041 tgcaagtgca gctgaggtcc cgccccgccc cgccccgccc cggcaggccc ggccccaccc
2101 cgccccgccc ccgctgcctt gcccatgggg gctgtattta aggacacccg tgccccaagc
2161 ccacctgggg ccccattaaa gatggagaga ggactgcgga aaaaaaaaaa aaaaaaa
//
```

FIG. 18a(ii)
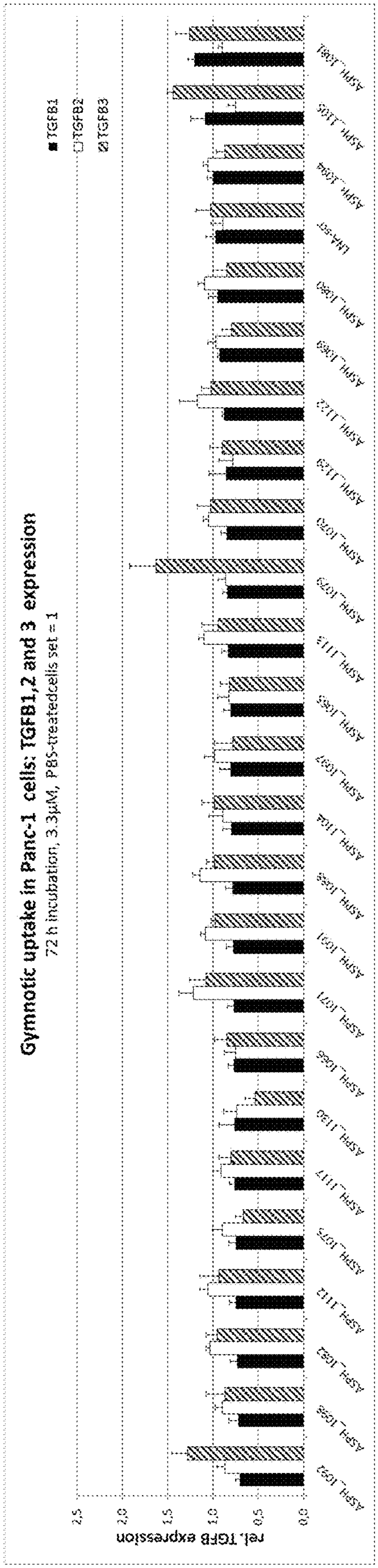

Gymnotic uptake in RenCa cells: TGFB1,2 and 3 expression
72 h incubation, 3.3µM, PBS-treatedcells set = 1

FIG. 19: Homology of ASPH_1024 and ASPH_1096 with human mRNAs

ASPH_1024 and ASPH_1096: 100% homology to human TGF-beta1 a) Position of ASPH_0009, ASPH_10024, and ASPH_1096 on human TGF-beta 2 mRNA

```
2361  GTGGAAATGGATACACGAACCCAAAGGGTACAATGCCAACTTCTGTGCTGGAGCATGCCC
```

(1024: bolt+underligned, 1096: yellow shadow)

```
Alignment of ASPH_1096 and ASPH_1024 with human TGF-beta2 mRNA

5' AGAAGTTGGCATGGT 3' ASPH_1096
3' TCTTCAACCGTAACA 5' human TGF-beta2


5' ATGGTAGCCCTTGG 3' ASPH_1024
3' TAACATGGGAAACC 5' human TGF-beta2
```

b) Position of ASPH_0009, ASPH_10024, and ASPH_1096 on human TGF-beta 3 mRNA

```
1851  GGGTCCATGAACCTAAGGGCTACTATGCCAACTTCTGCTCAGGCCCTTGCCCATACCTCCGC
```

(1024: bolt+underligned, 1096: yellow shadow)

```
Alignment of ASPH_1096 and ASPH_1024 with human TGF-beta3 mRNA

5' AGAAGTTGGCATGGT 3' ASPH_1096
3' TCTTCAACCGTATCA 5' human TGF-beta3

5' ATGGTAGCCCTTGG 3' ASPH_1024
3' TATCATCGGGAATC 3' human TGF-beta3
```

FIG. 20
Homology of ASPH_1131 and ASPH_1132 with human mRNAs

100% homology with human TGF-beta1 (1123-1136) and TGF-beta3 (1073-1086)

Position on human TGF-beta2 mRNA

```
1561 CCGGAGGTGA TTTCCATCTA CAACAGCACC AGGGACTTGC TCCAGGAGAA GGCGAGCCGG
```

alignment with human TGF-beta 2

```
5' CGGGTGCTGTTGTA 3' ASPH_1132
3' GACCACGACAACAT 5' human TGF-beta2

5' CGGGTGCTGTTGTA 3' ASPH_1131
3' GACCACGACAACAT 5' human TGF-beta2
```

FIG. 21

Homology of ASPH_1131 and ASPH_1132 with murine mRNAs

Position on mouse TGF-beta1 mRNA

1081 CCGCTGCCCG AGGCGGTGCT CGCTTTGTAC AACAGCACCC GCGACCGGGT GGCAGGCGAG alignment with mouse TGF-beta1 mRNA

5' CGGGTGCTGTTGTA 3' ASPH_1132

3' GCCCACGACAACAT 3' mouse TGF-beta 1

5' CGGGTGCTGTTGTA 3' ASPH_1131

3' GCCCACGACAACAT 3' mouse TGF-beta1

➔ 100% homology with mouse TGF-beta 1

Position on mouse TGF-beta2 mRNA 1401 tgaggtcccc ccggaggtga tttccatcta caacagtacc aggg Alignment with mouse TGF-beta2

5' CGGGTGCTGTTGTA 3' ASPH_1132

3' GACCATGACAACAT 5' mouse TGF-beta2

5' CGGGTGCTGTTGTA 3' ASPH_1131

3' GACCATGACAACAT 5' mouse TGF-beta2

Position on mouse TGF-beta3 mRNA 1321 cactttacaa cagcaccegg gagttgctgg aagagatgca cggggagagg gaggaaggct Alignment with mouse TGF-beta3

5' CGGGTGCTGTTGTA 3' ASPH_1132

3' GCCCACGACAACAT 5' mouse TGF-beta3

TGF-beta down-regulation in kidney

TGF-beta down-regulation in human pancreatic carcinoma Panc-1 tumors

TGF-beta2 down-regulation in subcutaneous human renal cell carcinoma 786-O tumors

FIG. 25: Nucleic acid sequence of human TGF-beta3 (SEQ ID NO. 336) – human TGF-beta3 mRNA (NCBI Reference Sequence NM_003239.2)

1 gacagaagca atggccgagg cagaagacaa gccgaggtgc tggtgaccct gggcgtctga
61 gtggatgatt ggggctgctg cgctcagagg cctgcctccc tgccttccaa tgcatataac
121 cccacacccc agccaatgaa gacgagaggc agcgtgaaca aagtcattta gaaagccccc
181 gaggaagtgt aaacaaaaga gaaagcatga atggagtgcc tgagagacaa gtgtgtcctg
241 tactgccccc acctttagct gggccagcaa ctgcccggcc ctgcttctcc ccacctactc
301 actggtgatc tttttttttt tacttttttt tccctttttct tttccattct cttttcttat
361 tttctttcaa ggcaaggcaa ggattttgat tttgggaccc agccatggtc cttctgcttc
421 ttctttaaaa tacccacttt ctccccatcg ccaagcggcg tttggcaata tcagatatcc
481 actctattta tttttaccta aggaaaaact ccagctccct tcccactccc agctgccttg
541 ccacccctcc cagccctctg cttgccctcc acctggcctg ctgggagtca gagcccagca
601 aaacctgttt agacacatgg acaagaatcc cagcgctaca aggcacacag tccgcttctt
661 cgtcctcagg gttgccagcg cttcctggaa gtcctgaagc tctcgcagtg cagtgagttc
721 atgcaccttc ttgccaagcc tcagtctttg ggatctgggg aggccgcctg gttttcctcc
781 ctccttctgc acgtctgctg ggtctcttc ctctccaggc cttgccgtcc ccctggcctc
841 tcttcccagc tcacacatga agatgcactt gcaaagggct ctggtggtcc tggccctgct
901 gaactttgcc acggtcagcc tctctctgtc cacttgcacc accttggact tcggccacat
961 caagaagaag agggtggaag ccattagggg acagatcttg agcaagctca ggctcaccag
1021 ccccccctgag ccaacggtga tgacccacgt ccccctatcag gtcctggccc tttacaacag
1081 cacccgggag ctgctggagg agatgcatgg ggagagggag gaaggctgca cccaggaaaa
1141 caccgagtcg gaatactatg ccaaagaaat ccataaattc gacatgatcc aggggctggc
1201 ggagcacaac gaactggctg tctgccctaa aggaattacc tccaaggttt tccgcttcaa
1261 tgtgtcctca gtggagaaaa atagaaccaa cctattccga gcagaattcc gggtcttgcg
1321 ggtgcccaac cccagctcta agcggaatga gcagaggatc gagctcttcc agatccttcg
1381 gccagatgag cacattgcca aacagcgcta tatcggtggc aagaatctgc ccacacgggg
1441 cactgccgag tggctgtcct ttgatgtcac tgacactgtg cgtgagtggc tgttgagaag
1501 agagtccaac ttaggtctag aaatcagcat tcactgtcca tgtcacacct ttcagcccaa
1561 tggagatatc ctggaaaaca ttcacgaggt gatggaaatc aaattcaaag gcgtggacaa
1621 tgaggatgac catggccgtg gagatctggg gcgcctcaag aagcagaagg atcaccacaa
1681 ccctcatcta atcctcatga tgattccccc acaccggctc gacaacccgg gccagggggg
1741 tcagaggaag aagcgggctt tggacaccaa ttactgcttc cgcaacttgg aggagaactg
1801 ctgtgtgcgc cccctctaca ttgacttccg acaggatctg ggctggaagt gggtccatga
1861 acctaagggc tactatgcca acttctgctc aggcccttgc ccatacctcc gcagtgcaga
1921 cacaacccac agcacggtgc tgggactgta caacactctg aaccctgaag catctgcctc
1981 gccttgctgc gtgccccagg acctggagcc cctgaccatc ctgtactatg ttgggaggac
2041 ccccaaagtg gagcagctct ccaacatggt ggtgaagtct tgtaaatgta gctgagaccc
2101 cacgtgcgac agagagaggg gagagagaac caccactgcc tgactgcccg ctcctcggga
2161 aacacacaag caacaaacct cactgagagg cctggagccc acaaccttcg gctccgggca
2221 aatggctgag atggaggttt ccttttggaa catttctttc ttgctggctc tgagaatcac
2281 ggtggtaaag aaagtgtggg tttggttaga ggaaggctga actcttcaga acacacagac
2341 tttctgtgac gcagacagag gggatgggga tagaggaaag ggatggtaag ttgagatgtt
2401 gtgtggcaat gggatttggg ctaccctaaa gggagaagga agggcagaga atggctgggt
2461 cagggccaga ctggaagaca cttcagatct gaggttggat ttgctcattg ctgtaccaca
2521 tctgctctag ggaatctgga ttatgttata caaggcaagc attttttttt tttttttaaa
2581 gacaggttac gaagacaaag tcccagaatt gtatctcata ctgtctggga ttaagggcaa
2641 atctattact tttgcaaact gtcctctaca tcaattaaca tcgtgggtca ctacagggag
2701 aaaatccagg tcatgcagtt cctggcccat caactgtatt gggccttttg gatatgctga
2761 acgcagaaga aagggtggaa atcaaccctc tcctgtctgc cctctgggtc cctcctctca
2821 cctctccctc gatcatattt ccccttggac acttggttag acgccttcca ggtcaggatg
2881 cacatttctg gattgtggtt ccatgcagcc ttggggcatt atgggttctt cccccacttc
2941 ccctccaaga ccctgtgttc atttggtgtt cctggaagca ggtgctacaa catgtgaggc
3001 attcggggaa gctgcacatg tgccacacag tgacttggcc ccagacgcat agactgaggt
3061 ataaagacaa gtatgaatat tactctcaaa atctttgtat aaataaatat ttttggggca
3121 tcctggatga tttcatcttc tggaatattg tttctagaac agtaaaagcc ttattctaag
3181 gtg Effect on protein level by use of ASPH47

Effect on protein level by use of ASPH1047

Effect on protein level by use of ASPH1106

Effect on protein level by use of multispecific ASPH1132

Effect on protein level by use of a combination of ASPH47 and ASPH1047

Negative control - scrLNA

Gymnotic uptake in Panc-1 cells: TGFB1,2 and 3 expression
72 h incubation, 3.3μM, PBS-treated cells set = 1

Gymnotic uptake in RenCa cells: TGFB1,2 and 3 expression
72 h incubation, 3.3µM, PBS-treated cells set = 1

Transfection of A172cells: TGFB1, -2 and -3 expression
24 h post transfection, 10 nM, mock-treatedcells set = 1

Tissue Distribution of ASPH0047

TGF-beta2 downregulation by ASP00047 in the kidney

TGF-β2 mRNA downregulation in established subcutaneous tumors (A-D) or kidney (E-F)

Effect of systemic treatment of Balb/c mice with ASPH_0047 on lung metastasis in orthotopic and intravenous Renca models Effect of systemic treatment of Nalb/c mice with ASPH_0047 on lung metastasis in orthotopic mouse mammary carcinoma 4T1 model

MODIFIED TGF-BETA OLIGONUCLEOTIDES

CROSS REFERENCE TO RELATED APPLICATIONS

The invention is a divisional and claims priority to U.S. application Ser. No. 14/780,043, filed on Sep. 25, 2015, which is a national phase of PCT/EP2014/056221, filed on Mar. 27, 2014, which claims the benefit of priority to European Patent Application No. 13199826.2, filed Dec. 30, 2013, European Patent Application No. 13173078.0, filed Jun. 20, 2013, and European Patent Application No. 13161474.5, filed Mar. 27, 2013, the entire contents of each of which are hereby incorporated in total by reference.

SEQUENCE LISTING

This application incorporates by reference the Sequence Listing contained in an ASCII text file named "362346_00046 SeqList.txt" submitted via EFS-Web. The text file was created on Jan. 29, 2018, and is 90 kb in size.

BACKGROUND OF THE INVENTION

This invention is directed to oligonucleotides consisting of 10 to 20 nucleotides of elected regions of the TGF-beta2 nucleic acid sequence, alternatively elected of the TGF-beta1 or TGF-beta3 nucleic acid sequence, which comprise modified nucleotides such as LNA, ENA, polyalkylene oxide-, 2'-fluoro, 2'-O-methoxy and/or 2'-O-methyl modified nucleotides.

Transforming growth factor beta (TGF-beta) is a protein that controls proliferation, cellular differentiation, and other functions in most cells. It is a type of cytokine which plays amongst others a role in immunity, cancer, heart disease, diabetes, Marfan syndrome, Loeys-Dietz syndrome, Parkinson's disease, and AIDS.

TGF-beta is a secreted protein that exists in at least three isoforms (TGF-beta1, TGF-beta2 and TGF-beta3) encoded by different genes but sharing strong sequence and structure homologies. TGF-beta acts as an antiproliferative factor in normal epithelial cells and at early stages of oncogenesis. However, later in tumor development TGF-beta can become tumor promoting through mechanisms including the induction of epithelial-to-mesenchymal transition (EMT), a process that is thought to contribute to tumor progression, invasion and metastasis (see "Glycoproteomic analysis of two mouse mammary cell lines during transforming growth factor (TGF)-beta induced epithelial to mesenchymal transition" $7^{th}$ space.com.2009-01-08. Retrieved: 2009 Jan. 29).

In normal (epithelial) cells, TGF-beta stops the cell cycle at the G1 stage (and stops cell proliferation), induce differentiation, or promote apoptosis. When a cell is transformed into a cancer cell, TGF-beta no longer suppresses cell proliferation, which is often the result of mutations in the signaling pathway, and cancer cells proliferate. Proliferation of stromal fibroblasts is also induced by TGF-beta. Both cells increase their production of TGF-beta. This TGF-beta acts on the surrounding stromal cells, immune cells, endothelial, smooth-muscle cells, and tumor microenvironment (see Pickup et al., "The roles of TGFβ in the tumour microenvironment", Nature Reviews Cancer (2013), 13: 788-799). Thereby, it promotes angiogenesis, and by suppressing proliferation and activation of immune cells it causes immunosuppression.

TGF-beta1-deficient mice die from cardiac, pulmonary, and gastric inflammation, suggesting that TGF-beta has a vital role in suppressing the activation and proliferation of inflammatory cells. Smad3 is one of the key elements in TGF-beta dependent downstream signaling pathways. Smad3-deficient mice develop chronic mucosal infections due to impairment of T-cell activation and mucosal immunity, suggesting a key role for TGF-beta in these processes. With respect to cancer, the production and secretion of TGF-beta by certain cancer cells suppress the activities of infiltrating immune cells, thereby helping the tumor to escape host immunosurveillance. This immunosuppressive effect may be another important mechanism by which TGF-beta stimulates the growth of late-stage tumors (see Blobe G C et al., May 2000, "Role of transforming growth factor beta in human disease", N. Engl. J. Med. 342 (18), 1350-1358). TGF-beta also converts effector T-cells, which normally attack cancer with an inflammatory (immune) reaction, into regulatory (suppressor) T-cells, which turn off the inflammatory reaction.

Further, TGF-beta is one of the most potent regulators of the production and deposition of extracellular matrix. It stimulates the production and affects the adhesive properties of the extracellular matrix by two major mechanisms. First, TGF-beta stimulates fibroblasts and other cells to produce extracellular-matrix proteins and cell-adhesion proteins, including collagen, fibronectin, and integrins. Second, TGF-beta decreases the production of enzymes that degrade the extracellular matrix, including collagenase, heparinase, and stromelysin, and increases the production of proteins that inhibit enzymes that degrade the extracellular matrix, including plasminogen-activator inhibitor type 1 and tissue inhibitor of metalloprotease. The net effect of these changes is to increase the production of extracellular-matrix proteins and either to increase or to decrease the adhesive properties of cells in a cell-specific manner. In many cancer cells the production of TGF-beta is increased, which increases the invasiveness of the cells by increasing their proteolytic activity and promoting their binding to cell-adhesion molecules (see Blobe G C et al., May 2000, "Role of transforming growth factor beta in human disease", N. Engl. J. Med. 342 (18), 1350-1358).

Thus, therapeutic agents which are able to influence TGF-beta expression and activity, respectively, are essential in particular for use in preventing and/or treating TGF-beta linked diseases. EP 1008649 and EP 0695354, for example, disclose oligonucleotides hybridizing with the mRNA of TGF-beta1 and/or TGF-beta2, and which are suitable to be used for manufacturing pharmaceutical compositions for example for preventing and/or treating cancer. None of these oligonucleotides comprises modifications such as LNA, ENA etc.

WO 2003/85110, WO 2005/061710, and WO 2008/138904 for example refer to oligonucleotides comprising modifications of the nucleotides, which are directed to the inhibition of HIF-1A, Bcl-2 and HER3, respectively, usable in the treatment of cancer.

Criteria for the selection of oligonucleotides are mainly the length of the oligonucleotide, the GC-percentage, the tendency for hairpin formation, dimerization and the melting temperature (Tm). In general, high Tm (melting temperature) is preferred. Furthermore, the oligonucleotides must be specific for the target mRNA and shall not hybridize to non-target mRNAs in order to decrease potential off-target effects.

Hence, there is a high scientific and medical need for therapeutic agents, which reduce or inhibit TGF-beta expression and/or activity. Particularly, there is a long-standing need for oligonucleotides such as antisense oligonucleotides, which specifically interact and thus, reduce or inhibit the expression of TGF-beta1, TGF-beta2, and/or TGF-beta3, as well as oligonucleotides, which specifically inhibit TGF-beta1 and TGF-beta2, or TGF-beta1 and TGF-beta3, or TGF-beta2 and TGF-beta3, without causing any (severe) side effects.

SUMMARY OF THE INVENTION

The present invention refers to oligonucleotides consisting of 10 to 20, preferably 12 to 18 nucleotides of the TGF-beta2 nucleic acid sequence of SEQ ID NO. 1 (see FIG. 2*a* and FIG. 2*b*), or of the TGF-beta1 nucleic acid sequence of SEQ ID NO. 335 (see FIG. 12), or of the TGF-beta3 nucleic acid sequence of SEQ ID NO. 336 (see FIG. 25), wherein one or more nucleotide(s) of the oligonucleotide is/are modified. Some of the oligonucleotides of the present invention correspond to TGF-beta1, TGF-beta2, and TGF-beta3, or to TGF-beta1 and TGF-beta2, or TGF-beta1 and TGF-beta3, or TGF-beta2 and TGF-beta3. Preferred oligonucleotides comprise or consist of one of SEQ ID NO. 2 to 149 (TGF-beta2), of one of SEQ ID No. 150-334 (TGF-beta1), or of one of SEQ ID No. 337-402 (TGF-beta3), which are presented in Table 1.

In particular, oligonucleotides of the present invention comprise or consist of 10 to 20, more preferred of 12 to 18 nucleotides of the region of nucleic acid no. 1380 to 1510 of SEQ ID NO. 1, wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 2 (e.g., ASPH36: GACCAGATGCAGGA), SEQ ID NO. 3 (e.g., ASPH80: GCGACCGTGACCAGAT), SEQ ID NO. 4 (e.g., ASPH98: GCGCGACCGTGACC), SEQ ID NO. 5 (e.g., ASPH111: AGCGCGACCGTGA), or SEQ ID NO. 6 (e.g., ASPH121 or ASPH153: GACCGTGACCAGAT), SEQ ID NO. 7 (e.g., ASPH15: CTGCCCGCGGAT), SEQ ID NO. 8 (e.g., ASPH17: TCTGCCCGCGGAT), SEQ ID NO. 9 (e.g., ASPH26 or ASPH27: GGATCTGCCCGCGGA), SEQ ID NO. 10 (e.g., ASPH37: CTTGCTCAGGATCTGCC), SEQ ID NO. 11 (e.g., ASPH52 or 53: GCTCAGGATCTGCCCGCGGA), SEQ ID NO. 12 (e.g., ASPH112: GGATCGCCTCGAT), SEQ ID NO. 13 (e.g., ASPH119: CCGCGGATCGCC), or SEQ ID NO. 31 (e.g., ASPH30: CGATCCTCTTGCGCAT).

In another embodiment the invention refers to an oligonucleotide, comprising or consisting of 10 to 20, more preferred of 12 to 18 nucleotides of the region of nucleic acid no. 2740 to 2810 of the TGF-beta2 nucleic acid sequence of SEQ ID NO. 1, wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 57 (e.g., ASPH65: TCTGAACTAGTACCGCC), SEQ ID NO. 73 (e.g., ASPH82: AACTAGTACCGCCTTT), or SEQ ID NO. 103 (e.g., ASPH115: CTAGTACCGCCTT).

In a further embodiment the invention refers to an oligonucleotide, comprising or consisting of 10 to 20, more preferred of 12 to 18 nucleotides of the region of nucleic acid no. 1660 to 1680 of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1 and/or TGF-beta2 expression and activity, respectively. A preferred oligonucleotide comprises or consists of SEQ ID NO. 14 (e.g., ASHP01 or ASPH02: ACCTCCTTGGCGTAGTA), SEQ ID NO. 15 (e.g., ASPH03 or ASPH04: CCTCCTTGGCGTAGTA), SEQ ID NO. 16 (e.g., ASPH05, ASPH06, or ASPH07: CTCCTTGGCGTAGTA), or SEQ ID NO.17 (e.g., ASPH08: TCCTTGGCGTAGTA).

In another embodiment the invention relates to an oligonucleotide, comprising or consisting of 10 to 20, more preferred of 12 to 18 nucleotides, most preferably 13 nucleotides of the region of nucleic acid no. 2390 to 2410 of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1, TGF-beta2, and/or TGF-beta3 expression and activity, respectively. A preferred oligonucleotide comprises or consists of SEQ ID NO. 18 (e.g., ASPH9 or ASPH10: CAGAAGTTGGCAT).

In another embodiment the invention relates to an oligonucleotide, comprising or consisting of 10 to 20, more preferred of 12 to 18 nucleotides of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1, TGF-beta2, and/or TGF-beta3, most preferably of TGF-beta2 expression and activity, respectively. A preferred oligonucleotide comprises or consists of one of SEQ ID NO. 19 to 56, 58 to 72, 74 to 102, 104 to 138 (e.g., ASHP11-ASPH14, ASPH16, ASPH18-ASPH25, ASPH28-ASPH35, ASPH38-ASPH51, ASPH60-64, ASPH66-ASPH79, ASPH81, ASPH83-ASPH97, ASPH99-ASPH110, ASPH113, ASPH114, ASPH116-118, ASPH120, ASPH122-ASPH152, ASPH154-ASPH183, or T-LNA (SEQ ID NO: 144)).

Preferred oligonucleotides of the present invention are ASPH01, ASPH03, ASPH05, ASPH17, ASPH22, ASPH26, ASPH27, ASPH35, ASPH36, ASPH37, ASPH45, ASPH47, ASPH48, ASPH65, ASPH69, ASPH71, ASPH80, ASPH82, ASPH98, ASPH105, ASPH115, ASPH190, ASPH191, ASPH192, and ASPH193, respectively.

Further preferred oligonucleotides of the present invention are ASPH1000 to ASPH1132 as shown in Table 1, which preferably inhibit the expression and/or activity of TGFbeta1 mRNA. Preferred oligonucleotides this group are for example ASPH1047, ASPH1051, ASPH1059, ASPH1106, ASPH1139, ASPH1150, ASPH1162, ASPH1163, ASPH1175, ASPH1178, and ASPH1181, respectively.

In an alternative embodiment oligonucleotides are preferably inhibiting the expression and/or activity of TGF-beta3 mRNA. Such oligonucleotides are for example ASPH2000, ASPH2001, ASPH2002, ASPH2003, ASPH2004, ASPH2005, ASPH2006, ASPH2007, ASPH2008, ASPH2009, ASPH2010, ASPH2011, ASPH2012, ASPH2013, ASPH2014, ASPH2015, ASPH2016, ASPH2017, ASPH2018, ASPH2019, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2046, ASPH2047, ASPH2048, ASPH2049, ASPH2050, ASPH2051, ASPH2052, ASPH2053, ASPH2054, ASPH2055, ASPH2056, ASPH2057, ASPH2058, ASPH2059, ASPH2060, ASPH2061, ASPH2062, ASPH2063, ASPH2064, ASPH2065, and ASPH2066, respectively.

Oligonucleotides of the present invention show an unexpected strong and specific inhibition of TGF-beta1, TGF-beta2, or TGF-beta3, or TGF-beta1 and TGF-beta2. Alternatively, oligonucleotides of the present invention show strong and specific inhibition of TGF-beta1 and TGF-beta3, or TGF-beta1 and TGF-beta2, or TGF-beta2 and TGF-beta3, and in a further alternative TGF-beta1, TGF-beta2 and TGF-beta3.

Modifications of one or more nucleotides of the oligonucleotides of the present invention are selected from the group consisting of LNA, ENA, polyalkylene oxide such as triethylene glycol (TEG), 2'-fluoro, 2'-O-methoxy and 2'-O-methyl. The modifications are preferably located at the 5'- and/or 3'-end of the oligonucleotide. An oligonucleotide comprising such modified nucleotide is a modified oligonucleotide.

Modified nucleotides are for example arranged in a row, one directly next to the other, or in different patterns, where one or more unmodified nucleotides follow a modified nucleotide. For example an oligonucleotide starts with one or more modified nucleotides followed by one or more, e.g., one, two, three or four, unmodified or unlocked nucleotides followed again by one or more modified nucleotides. In one embodiment both ends of the oligonucleotide comprise an identical pattern of modified and unmodified or unlocked nucleotides. In another embodiment, the pattern of modifications at the 3'- and 5'-end differ including that one end does not comprise a modified nucleotide. Preferably the modified oligonucleotides comprise a series of 8 or 9 unlocked nucleotides.

Alternatively, a nucleotide at any other position in the oligonucleotide is modified, or at least one nucleotide at the 5'- and/or 3'-end of the oligonucleotide and at any other position in the oligonucleotide. For example ASPH1071, ASPH1100, ASPH1109, ASPH 1110, ASPH1111, ASPH1115, ASPH1126, ASPH1127 and ASPH1128 belong to a group of TGF-beta oligonucleotides, for example TGF-beta1 oligonucleotides, which comprises modified nucleosides such as LNA, ENA etc. in different patterns, e.g., separated from each other by an unlocked nucleotide. The oligonucleotides comprise either one type of modification, or one or more different modifications. Optionally, at least one phosphate linkage between two consecutive nucleotides (modified or unmodified) of the oligonucleotide is a phosphorothioate or a methylphosphonate. In a preferred embodiment, the oligonucleotides of the present invention are phosphorothioates.

Moreover, the present invention refers to TGF-beta antisense oligonucleotides, which interact and inhibit the expression of more than one TGF-beta isoform, even if the oligonucleotide is not 100% complementary to the TGF-beta1, TGF-beta2 and/or TGF-beta3 sequence. Such antisense oligonucleotides are for example ASPH1024, ASPH1096, ASPH1131 and ASPH1132, respectively. These oligonucleotides preferably interact with TGF-beta sequences of different species such as human and mouse as for example ASPH1131 and ASPH1132, respectively.

All the oligonucleotides of the different embodiments are for use in a method of the prevention and/or treatment of a malignant or a benign tumor, an immunologic disease, fibrosis (e.g., idiopathic pulmonary fibrosis, renal fibrosis, kidney fibrosis), cirrhosis (e.g., liver cirrhosis), scleroderma or related dermatologic diseases, an eye disease such as glaucoma or posterior capsular opacification (PCO), a CNS disease, hair loss etc.

BRIEF DESCRIPTION OF THE DRAWINGS

FIG. 1 presents examples of nucleotide modifications.

FIG. 2*a* and FIG. 2*b* show the nucleic acid sequence of human TGF-beta2 mRNA (NM_003238.3).

FIG. 3*a*(*i*), FIG. 3*a*(*ii*), FIG. 3*a*(*iii*)) refers to the results for the modified oligonucleotides ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54.

FIG. 4*a*(*i*), and FIG. 4*a*(*ii*), refer to the results for the modified oligonucleotides ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52.

FIG. 5a and FIG. 5b present the results for the modified oligonucleotides ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183. Experiments are described in Example 4.

FIG. 6a) and FIG. 6b) show the results for the modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48 on mRNA (FIG. 7a) and protein (FIG. 7b) level. Experiments are described in Example 5.

FIG. 12 presents the nucleic acid sequence of human TGF-beta1 mRNA (NM_000660.4).

FIG. 13a and FIG. 13b refer to the results for the modified oligonucleotides ASPH05, ASPH09, ASPH1000, ASPH1001, ASPH1002, ASPH1003, ASPH1004, ASPH1005, ASPH1006, ASPH 1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH 1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, and ASPH1061. Experiments are described in Example 12.

FIG. 14 refers to the results for the modified oligonucleotides ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH 1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 13.

FIG. 15*a*, FIG. 15*b*, and FIG. 15*c* refer to the results for the modified oligonucleotides ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, and ASPH1062. Experiments are described in Example 14.

FIG. 16*a*, FIG. 16*b*, and FIG. 16*c* refer to the results for the modified oligonucleotides ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 15.

FIG. 17 refers to the results for the modified oligonucleotides ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132. Experiments are described in Example 16.

FIG. 18*a*(*i*), and FIG. 18*a*(*ii*) refer to the results for the modified oligonucleotides ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132.

FIG. 19 presents a sequence alignment of ASPH1024 and ASPH1096 with the human sequence of TGF-beta1, TGF-beta2 and TGF-beta3 mRNAs. Both oligonucleotides are 100% homologous to the human sequence of TGF-beta1. ASPH1024 has three mismatches with the human sequence of TGF-beta2 and two mismatches with human sequence of TGF-beta3. ASPH1096 has one mismatch with the human sequence of TGF-beta2, and one mismatch with the human sequence of TGF-beta3. Both oligonucleotides show inhibition of different human TGF-beta isoforms (TGF-beta1, TGF-beta2, and TGF-beta3). For example ASPH1024 inhibits the expression and activity of TGF-beta1 and TGF-beta2 (see FIG. 16*a*, FIG. 16*b*, and FIG. 16*c*) and ASPH1096 inhibits the expression and activity of TGF-beta1, TGF-beta2 and TGF-beta3 as depicted in FIG. 17 for example. ASPH009, which is 100% homologous to the human sequence of TGF-beta1, TGF-beta2, and TGF-beta3 was used as a control.

FIG. 20 shows an alignment of ASPH1131 and ASPH1132 with the human sequences of TGF-beta1, TGF-beta2 and TGF-beta3 mRNAs. Both oligonucleotides are 100% homologous to the human sequences of TGF-beta1 and TGF-beta3. Each of ASPH1131 and ASPH1132 has one mismatch with the human sequence of TGF-beta2. Both oligonucleotides strongly inhibit the expression of all three human isoforms as depicted in FIG. 17 for example.

FIG. 21 depicts an alignment of ASPH1131 and ASPH1132 with the murine sequences of TGF-beta1, TGF-beta2 and TGF-beta3 mRNAs. Both oligonucleotides are 100% homologous to the murine sequences of TGF-beta1 and TGF-beta3. Each of ASPH1131 and ASPH1132 has two mismatches with the murine sequence of TGF-beta2. While ASPH1131 potently inhibits murine TGF-beta2 and TGF-beta3, ASPH1132 very potently suppresses all murine TGF-beta isoforms as depicted in FIG. 18*b* for example.

FIG. 25 shows the nucleic acid sequence of human TGF-beta3 mRNA (NM_003239.2).

DETAILED DESCRIPTION OF THE INVENTION

Figure 3A:
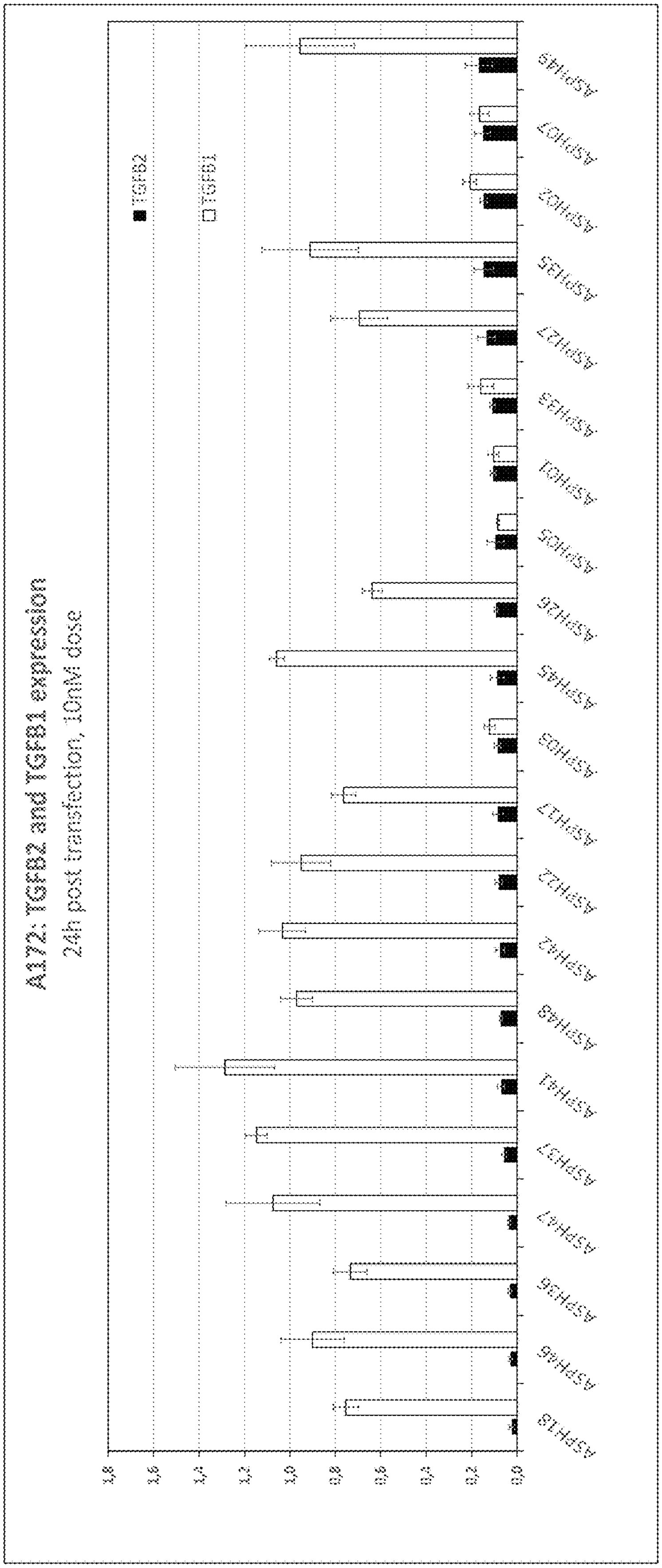
FIG. 3*a*(*i*), FIG. 3*a*(*ii*), FIG. 3*a*(*iii*), FIG. 3*b*(*i*), FIG. 3*b*(*ii*), FIG. 3*b*(*iii*), FIG. 3*c*)*i*, FIG. 3*c*(*ii*), and FIG. c(iii) depict the inhibition of the expression of TGF-beta1 and TGF-beta2 mRNA in human A172 glioma cells. A172 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection.

The present invention is directed to oligonucleotides, in particular antisense oligonucleotides, which comprise at least one modified nucleotide and are suitable to interact with TGF-beta mRNA. The oligonucleotides comprise or consist of 10 to 20, more preferred 12 to 18 nucleotides of the TGF-beta2 nucleic acid according to SEQ ID NO. 1 or of the TGF-beta1 nucleic acid according to SEQ ID NO. 335, or of the nucleic acid sequence of TGF-beta3 nucleic acid according to SEQ ID NO. 336. Most preferred the oligonucleotide comprises or consists of 12, 13, 14, 15, 16, 17, or 18 nucleotides. The oligonucleotides are preferably selected from the region of nucleic acid no. 1380 to 1510 (preferably no. 1380 to 1450 and/or no. 1480 to 1510), 1660 to 1680, or 2390 to 2410 of SEQ ID NO. 1. The oligonucleotide is a single or double stranded RNA or DNA, including siRNA, microRNA, aptamer or spiegelmer. Preferably, the oligonucleotide is an antisense oligonucleotide.

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altorse, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. The latter are for example locked nucleic acid (LNA), a 2'-O,4'-C-ethylene-bridged nucleic acid (ENA), polyalkylene oxide—(such as triethylene glycol (TEG)), 2'-fluoro, 2'-O-methoxy and 2'-O-methyl modified nucleotides as described for example by Freier & Altmann (Nucl. Acid Res., 1997, 25, 4429-4443) and Uhlmann (Curr. Opinion in Drug & Development (2000, 3 (2): 293-213), which are shown in FIG. 1.

A LNA is a modified RNA nucleotide, wherein the ribose moiety is modified with an extra bridge connecting the 2'oxygen and 4'carbon (2'-4'ribonucleoside). The bridge "locks" the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and are mixable and combinable, respectively, with DNA or RNA residues in the oligonucleotide.

The oligonucleotides of the present invention, i.e., modified oligonucleotides, comprise at least one modified nucleotide, preferably LNA and/or ENA, at the 5'- and/or 3'-end of the oligonucleotide. In a preferred embodiment, the oligonucleotide comprises 1, 2, 3, or 4 LNAs or ENAs at the 5'-end, and 1, 2, 3, or 4 LNAs or ENAs at the 3'-end. In another preferred embodiment, the oligonucleotide comprises 1, 2, 3, or 4 LNAs or ENAs at the 5'-end or 3'-end, and a polyalkylene oxide such as TEG at the 3'- or 5'-end. The modified oligonucleotides show a significantly increased inhibition on TGF-beta expression and activity, respectively, which results in an improved prevention and/or treatment of a malignant or benign tumor, fibrosis (e.g., idiopathic pulmonary fibrosis, renal fibrosis, kidney fibrosis), cirrhosis (e.g., liver cirrhosis), scleroderma or related dermatologic diseases, an eye disease such as glaucoma or posterior capsular opacification (PCO), a CNS disease, hair loss etc. The oligonucleotides of the present invention target TGF-beta linked diseases either by hybridization with TGF-beta mRNA, preferably TGF-beta1, TGF-beta2, or TGF-beta3, alternatively, TGF-beta1, TGF-beta2, and/or TGF-beta3 mRNAs, i.e., TGF-beta1 and TGF-beta2, or TGF-beta1 and TGF-beta3, or TGF-beta2 and TGF-beta3, or TGF-beta1, TGF-beta2 and TGF-beta3 mRNAs, or any other direct or indirect effect on the TGF-beta system.

Preferably two or more oligonucelotides are combined, wherein at least one oligonucleotide specifically inhibits TGF-beta1 and at least one oligonucleotide specifically inhibits TGF-beta2, or wherein at least one oligonucleotide specifically inhibits TGF-beta1 and at least one oligonucleotide specifically inhibits TGF-beta3, or wherein at least one oligonucleotide specifically inhibits TGF-beta2 and at least one oligonucleotide specifically inhibits TGF-beta3, or wherein at least one oligonucleotide specifically inhibits TGF-beta1, at least one oligonucleotide specifically inhibits TGF-beta2, and at least one oligonucleotide specifically inhibits TGF-beta3.

In another embodiment, one oligonucleotide inhibits two TGF-beta isoforms such as TGF-beta1 and TGF-beta2, TGF-beta2 and TGF-beta3, or TGF-beta1 and TGF-beta3. An oligonucleotide inhibiting the expression of all three isoforms—TGF-beta1, TGF-beta2, and TGF-beta3—is defined as pan-specific oligonucleotide.

In a further embodiment three or more oligonucleotides are combined, wherein at least one oligonucleotide specifically inhibits TGF-beta1, another oligonucleotide specifically inhibits TGF-beta2, and a further oligonucleotide specifically inhibits TGF-beta3, and optionally one or more additional oligonucleotides inhibiting TGF-beta1, TGF-beta2 or TGF-beta3.

The oligonucleotides of the present invention have for example an $IC_{50}$ in the range of 0.1 to 20 μM, preferably in the range of 0.2 to 15 μM, more preferably in the range of 0.4 to 10 μM, and even more preferred in the range of 0.5 to 5 μM.

The present invention further refers to a pharmaceutical composition comprising an oligonucleotide according to the invention as active ingredient. The pharmaceutical composition comprises at least one oligonucleotide of the present invention and optionally further an antisense compound, an antibody, a chemotherapeutic compound, an anti-inflammatory compound, an antiviral compound and/or an immunomodulating compound. Pharmaceutically acceptable binding agents and adjuvants or carrier optionally comprise part of the pharmaceutical composition.

In one embodiment, the oligonucleotide and the pharmaceutical composition, respectively, is formulated as dosage unit in form of capsules, tablets and pills etc., respectively, which contain for example the following compounds: microcrystalline cellulose, gum or gelatin as binders; starch or lactose as excipients; stearates as lubricants, various sweetening or flavouring agents. For capsules the dosage unit may contain a liquid carrier like fatty oils. Likewise coatings of sugar or enteric agents may be part of the dosage unit.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intrathecal, intracameral, intraperitoneal, intraprostatic, intrapulmonary, intraspinal, intratracheal, intratumoral, intravenous, intravesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal administration.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and/or other suitable additive such as penetration enhancer, carrier compound and/or other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

Beside being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

The oligonucleotide or the pharmaceutical composition according to the invention is used in a method for the prevention and/or treatment of many different diseases, preferably benign or malignant tumors, immunologic diseases, bronchial asthma, heart disease, fibrosis (e.g., liver fibrosis, idiopathic pulmonary fibrosis, liver cirrhosis, kidney cirrhosis, scleroderma), diabetes, wound healing, disorders of the connective tissue (e.g., in heart, blood vessel, bone, joint, eye such as the Marfan or Loeys-Dietz syndrome), psoriasis, eye diseases (e.g., glaucoma, posterior capsular opacification (PCO) also known as secondary cataract), CNS disease (e.g., Alzheimer's disease, Parkinson's disease), coronary atherosclerosis (coronary intervention or coronary artery bypass graft (CABG) surgery or hair loss. A tumor is for example selected from the group of solid tumors, blood born tumors, leukemias, tumor metastasis, hemangiomas, acoustic neuromas, neurofibromas, trachomas, pyogenic granulomas, astrocytoma such as anaplastic astrocytoma, acoustic neuroma, blastoma, Ewing's tumor, craniopharyngloma, ependymoma, medulloblastoma, glioma, glioblastoma, hemangloblastoma, Hodgkins-lymphoma, medullablastoma, leukaemia, melanoma such as primary and/or metastatic melanoma, mesothelioma, myeloma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma (RCC, e.g., clear cell RCC, papillary RCC, chromophobe RCC), oncocytoma kidney cancer, transitional cell kidney cancer, retinoblastoma, skin cancer, small-cell bronchogenic/lung carcinoma, squamous cell carcinoma, sebaceous gland carcinoma, testicular carcinoma, and uterine cancer. The oligonucleotide or the pharmaceutical composition of the present invention is not only used in a method for the prevention and/or treatment of a tumor, but likewise on a metastasis.

The antisense oligonucleotides of the present invention are characterized in that they show an unexpected low toxicity (see for example Table 5) and thus, are well tolerated by different organisms. They oligonucleotides show a reasonable distribution in the organism, wherein highest concentrations are measured in the kidney, liver, skin and spleen.

The present invention provides numerous oligonucleotides, which are highly efficient in the reduction and inhibition, respectively, of TGF-beta, in particular TGF-beta1, TGF-beta2 and/or TGF-beta3 expression due to the specific selection of the sequence of the oligonucleotide and the modification of the nucleotide. The following Table 1 shows numerous preferred modified oligonucleotides according to the present invention (bold letters indicate the modified nucleoside). Each oligonucleotides is defined as ASPH and a number, which is defined by a specific sequence and modification of the nucleosides:

| SEQ ID NO. | Sequence (5'->3') | Modification | ASPH |
|---|---|---|---|
| 2 | **GAC**CAGATGCA**GGA** | LNA 3 + 3 | 36 |
| 3 | **GCG**ACCGTGACCA**GAT** | LNA 3 + 3 | 80 |
| 4 | **GCG**CGACCGTG**ACC** | LNA 3 + 3 | 98 |
| 5 | **AG**CGCGACCG**TGA** | LNA 2 + 3 | 111 |
| 6 | **GA**CCGTGACCAG**AT** | LNA 2 + 2 | 121 |
| 6 | **GAC**CGTGACCAGA**T** | LNA 3 + TEG | 153 |
| 7 | **CT**GCCCGCGG**AT** | LNA 2 + 2 | 15 |
| 8 | **TCT**GCCCGCGG**AT** | LNA 3 + 2 | 17 |
| 9 | **GGAT**CTGCCCGC**GGA** | LNA 4 + 3 | 26 |
| 9 | **GGA**TCTGCCCG**CGGA** | LNA 3 + 4 | 27 |
| 10 | **CTTG**CTCAGGATC**TGCC** | LNA 4 + 4 | 37 |
| 11 | GCTCAGGATCTGCCCG**CGGA** | 2' O-meth 4 + 4 | 52 |
| 11 | **GCTC**AGGATCTGCCCG**CGGA** | 2' fluoro 4 + 4 | 53 |

-continued

| SEQ ID NO. | Sequence (5'->3') | Modification | ASPH |
|---|---|---|---|
| 12 | **GGA**TCGCCTCG**AT** | LNA 3 + 2 | 112 |
| 13 | **CC**GCGGATCG**CC** | LNA 2 + 2 | 119 |
| 14 | **ACC**TCCTTGGCGTA**GTA** | LNA 3 + 3 | 01 |
| 14 | **ACCT**CCTTGGCGT**AGTA** | LNA 4 + 4 | 02 |
| 15 | **CCT**CCTTGGCGTA**GTA** | LNA 3 + 3 | 03 |
| 15 | **CCTC**CTTGGCGT**AGTA** | LNA 4 + 4 | 04 |
| 16 | **CTC**CTTGGCGTA**GTA** | LNA 3 + 3 | 05 |
| 16 | **CTCC**TTGGCGTA**GTA** | LNA 4 + 3 | 06 |
| 16 | **CTC**CTTGGCGT**AGTA** | LNA 3 + 4 | 07 |
| 17 | **TCC**TTGGCGTA**GTA** | LNA 3 + 3 | 08 |
| 18 | **CAG**AAGTTGGC**AT** | LNA 3 + 2 | 09 |
| 18 | **CA**GAAGTTGG**CAT** | LNA 2 + 3 | 10 |
| 19 | AAGTGGGCGGGAT | — | 11 |
| 19 | **AAGT**GGGCG**GGAT** | LNA 4 + 4 | 12 |
| 19 | **AAGT**GGGCG**GGAT** | 2' O-meth 4 + 4 | 13 |
| 19 | **AAGT**GGGCG**GGAT** | 2' fluoro 4 + 4 | 14 |
| 20 | **GC**GGGATGGC**AT** | LNA 2 + 2 | 16 |
| 21 | **GA**AATCACCT**CCG** | LNA 2 + 3 | 18 |
| 22 | **AA**GTGGGCGG**GAT** | LNA 2 + 3 | 19 |
| 23 | **TG**TAGCGCTG**GGT** | LNA 2 + 3 | 20 |
| 24 | **CGA**AGGAGAGC**CA** | LNA 3 + 2 | 21 |
| 25 | **TCG**CGCTCGCA**GGC** | LNA 3 + 3 | 22 |
| 26 | **AAG**TGGGCGGG**ATG** | LNA 3 + 3 | 23 |
| 27 | **ATG**TAGCGCTG**GGT** | LNA 3 + 3 | 24 |
| 28 | **CGA**AGGAGAGC**CAT** | LNA 3 + 3 | 25 |
| 29 | **GAAA**GTGGGCGG**GAT** | LNA 4 + 3 | 28 |
| 30 | **CGAA**GGAGAGCC**ATT** | LNA 4 + 3 | 29 |
| 31 | **CGAT**CCTCTTGC**GCAT** | LNA 4 + 4 | 30 |
| 32 | **AAGT**GGGCGGGA**TGGC** | LNA 4 + 4 | 31 |
| 33 | **GATG**GAAATCACC**TCCG** | LNA 4 + 4 | 32 |
| 34 | **AAAC**CTCCTTGGC**GTAG** | LNA 4 + 4 | 33 |
| 35 | **TAGA**AAGTGGGCG**GGAT** | LNA 4 + 4 | 34 |
| 36 | **GG**CGGGATGG**CAT** | LNA 2 + 3 | 35 |
| 37 | **GGGT**CTGTAGAA**AGTG** | LNA 4 + 4 | 38 |
| 38 | **GAA**GGAGAGCC**ATTC** | LNA 3 + 4 | 39 |
| 39 | **CCA**GGTTCCTG**TCTT** | LNA 3 + 4 | 40 |
| 40 | **TCT**GATCACCA**CTGG** | LNA 3 + 4 | 41 |
| 41 | **TTTC**TGATCACCA**CTGG** | LNA 4 + 4 | 42 |

-continued

| SEQ ID NO. | Sequence (5'->3') | Modification | ASPH |
|---|---|---|---|
| 42 | **GTCT**GTAGGAGG**GCA** | LNA 4 + 3 | 43 |
| 43 | **AGTC**TGTAGGAG**GGCA** | LNA 4 + 4 | 44 |
| 44 | **TC**TGTAGGAG**GGC** | LNA 2 + 3 | 45 |
| 45 | **CAGA**TGCCAGTTT**TAAC** | LNA 4 + 4 | 46 |
| 46 | **CAAA**GTATTTGGT**CTCC** | LNA 4 + 4 | 47 |
| 47 | **CCTT**AAGCCATCC**ATGA** | LNA 4 + 4 | 48 |
| 48 | **GTAC**TGGCCAGC**TAA** | LNA 4 + 3 | 49 |
| 49 | **GCCT**CGATCCTCTTGC**GCAT** | 2' O-meth 4 + 4 | 50 |
| 49 | **GCCT**CGATCCTCTTGC**GCAT** | 2' fluoro 4 + 4 | 51 |
| 50 | **AAAC**CTCCTTGGCGTA**GTAC** | 2' O-meth 4 + 4 | 54 |
| 50 | **AAAC**CTCCTTGGCGTA**GTAC** | 2' fluoro 4 + 4 | 55 |
| 51 | **GAAA**GTGGGCGGGATG**GCAT** | 2' O-meth 4 + 4 | 56 |
| 51 | **GAAA**GTGGGCGGGATG**GCAT** | 2' fluoro 4 + 4 | 57 |
| 52 | **GAA**TTGCTCGCTTA**GGG** | LNA 3 + 3 | 60 |
| 53 | **CGT**CGCGGTTGCGT**TCA** | LNA 3 + 3 | 61 |
| 54 | **CGT**GGCCTACACCC**TGG** | LNA 3 + 3 | 62 |
| 55 | **TTC**TAAAGCAATAG**GCC** | LNA 3 + 3 | 63 |
| 56 | **AGA**ATGGTTAGAGG**TTC** | LNA 3 + 3 | 64 |
| 57 | **TCT**GAACTAGTACC**GCC** | LNA 3 + 3 | 65 |
| 58 | **CCC**ATTAATATGAC**CTC** | LNA 3 + 3 | 66 |
| 59 | **TTT**AGTTAGAACCC**TAA** | LNA 3 + 3 | 67 |
| 60 | **CCT**CAGATATAGAT**AAC** | LNA 3 + 3 | 68 |
| 61 | **TAC**TATTATGGCAT**CCC** | LNA 3 + 3 | 69 |
| 62 | **TGC**CCACTTGCATA**CTA** | LNA 3 + 3 | 70 |
| 63 | **AGC**GTAATTGGTCA**TCA** | LNA 3 + 3 | 71 |
| 64 | **CGT**TGGCAGAACAT**AGA** | LNA 3 + 3 | 72 |
| 65 | **GGG**ATACTGTCTAG**ACC** | LNA 3 + 3 | 73 |
| 66 | **ATT**GGCAACTCGTT**TGA** | LNA 3 + 3 | 74 |
| 67 | **CGT**CAGGCTAATA**TTC** | LNA 3 + 3 | 75 |
| 68 | **GGA**TGACTCCCTA**GAC** | LNA 3 + 3 | 76 |
| 69 | **GTC**GCGGTTGCGT**TCA** | LNA 3 + 3 | 77 |
| 70 | **CTC**GGTACTCGGT**CGG** | LNA 3 + 3 | 78 |
| 71 | **GGT**TCGGTCCTGC**CTT** | LNA 3 + 3 | 79 |
| 72 | **AAT**AGGCCGCATC**CAA** | LNA 3 + 3 | 81 |
| 73 | **AAC**TAGTACCGCC**TTT** | LNA 3 + 3 | 82 |
| 74 | **TCG**GTCATATAAT**AAC** | LNA 3 + 3 | 83 |
| 75 | **AGA**CCGTCAGGC**TAA** | LNA 3 + 3 | 84 |

-continued

| SEQ ID NO. | Sequence (5'->3') | Modification | ASPH |
|---|---|---|---|
| 76 | **GTC**GCGGTTGCG**TTC** | LNA 3 + 3 | 85 |
| 77 | **TTC**CACTGCGGC**GCT** | LNA 3 + 3 | 86 |
| 78 | **AAG**GAGCGGTTC**GGT** | LNA 3 + 3 | 87 |
| 79 | **CTC**GGGTGCGGA**GTG** | LNA 3 + 3 | 88 |
| 80 | **CTG**ACTTTGGCG**AGT** | LNA 3 + 3 | 89 |
| 81 | **GAT**AGGAACGGT**ACG** | LNA 3 + 3 | 90 |
| 82 | **CAC**TTTGGATTC**CCG** | LNA 3 + 3 | 91 |
| 83 | **GTC**GCGGTTGC**GTT** | LNA 3 + 3 | 92 |
| 84 | **TAC**ACCCTGGC**GGG** | LNA 3 + 3 | 93 |
| 85 | **CTC**GGTACTCG**GTC** | LNA 3 + 3 | 94 |
| 86 | **AGG**AGCGGTTC**GGT** | LNA 3 + 3 | 95 |
| 87 | **GTC**TCGGGTGC**GGA** | LNA 3 + 3 | 96 |
| 88 | **TAC**GGGACGGG**CAG** | LNA 3 + 3 | 97 |
| 89 | **CGT**CGCTCCTC**TCG** | LNA 3 + 3 | 99 |
| 90 | **TAG**CGCTGGGT**TGG** | LNA 3 + 3 | 100 |
| 91 | **AAG**CAATAGGC**CGC** | LNA 3 + 3 | 101 |
| 92 | **TAC**GGGCATGC**TCC** | LNA 3 + 3 | 102 |
| 93 | **AGG**CGCGGGAT**AGG** | LNA 3 + 3 | 103 |
| 94 | **TTT**GGATTCCC**GCC** | LNA 3 + 3 | 104 |
| 95 | **ACC**ACTAGAGC**ACC** | LNA 3 + 3 | 105 |
| 96 | **GCG**TTGGCAGA**ACA** | LNA 3 + 3 | 106 |
| 97 | **TT**GCTCGCTT**AGG** | LNA 2 + 3 | 107 |
| 98 | **GTC**GCGGTTGC**GT** | LNA 3 + 2 | 108 |
| 99 | **GG**CGCTCGGT**ACT** | LNA 2 + 3 | 109 |
| 100 | **ATC**TGAACTCG**GC** | LNA 3 + 2 | 110 |
| 101 | **CG**GTTGGTCT**GTT** | LNA 2 + 3 | 113 |
| 102 | **TC**CACCCTAG**ATC** | LNA 2 + 3 | 114 |
| 103 | **CT**AGTACCGC**CTT** | LNA 2 + 3 | 115 |
| 104 | **GGT**CGGCAGTC**AA** | LNA 3 + 2 | 116 |
| 105 | **CT**TGCGACAC**CC** | LNA 2 + 2 | 117 |
| 106 | **GA**GCGGTTCG**GT** | LNA 2 + 2 | 118 |
| 107 | **AC**ACAGTAGTGC**AT** | LNA 2 + 2 | 120 |
| 108 | **GG**GTCTGTAGAA**AG** | LNA 2 + 2 | 122 |
| 108 | **GGG**TCTGTAGAAAG | LNA 3 + TEG | 154 |
| 109 | **GG**TTGGAGATGT**TA** | LNA 2 + 2 | 123 |
| 109 | **GGT**TGGAGATGTTA | LNA 3 + TEG | 155 |
| 110 | **TG**GGTTGGAGAT**GT** | LNA 2 + 2 | 124 |
| 110 | **TGG**GTTGGAGATGT | LNA 3 + TEG | 156 |

-continued

| SEQ ID NO. | Sequence (5'->3') | Modification | ASPH |
|---|---|---|---|
| 111 | **GC**TGGGTTGGAG**AT** | LNA 2 + 2 | 125 |
| 111 | **GCT**GGGTTGGAGAT | LNA 3 + TEG | 157 |
| 112 | **GC**GCTGGGTTGG**AG** | LNA 2 + 2 | 126 |
| 112 | **GCG**CTGGGTTGGAG | LNA 3 + TEG | 158 |
| 113 | **AG**CGCTGGGTTG**GA** | LNA 2 + 2 | 127 |
| 113 | **AGC**GCTGGGTTGGA | LNA 3 + TEG | 159 |
| 114 | **TA**GCGCTGGGTT**GG** | LNA 2 + 2 | 128 |
| 114 | **TAG**CGCTGGGTTGG | LNA 3 + TEG | 160 |
| 115 | **GT**AGCGCTGGGT**TG** | LNA 2 + 2 | 129 |
| 115 | **GTA**GCGCTGGGTTG | LNA 3 + TEG | 161 |
| 116 | **GA**TGTAGCGCTG**GG** | LNA 2 + 2 | 130 |
| 116 | **GAT**GTAGCGCTGGG | LNA 3 + TEG | 162 |
| 117 | **CC**ATTCGCCTTC**TG** | LNA 2 + 2 | 131 |
| 117 | **CCA**TTCGCCTTCTG | LNA 3 + TEG | 163 |
| 118 | **GA**GAGCCATTCG**CC** | LNA 2 + 2 | 132 |
| 118 | **GAG**AGCCATTCGCC | LNA 3 + TEG | 164 |
| 119 | **AG**CAGGGACAGT**GT** | LNA 2 + 2 | 133 |
| 119 | **AGC**AGGGACAGTGT | LNA 3 + TEG | 165 |
| 120 | **GC**AGGAGATGTG**GG** | LNA 2 + 2 | 134 |
| 120 | **GCA**GGAGATGTGGG | LNA 3 + TEG | 166 |
| 121 | **CG**GTTGGTCTGT**TG** | LNA 2 + 2 | 135 |
| 121 | **CGG**TTGGTCTGTTG | LNA 3 + TEG | 167 |
| 122 | **CC**GGTTGGTCTG**TT** | LNA 2 + 2 | 136 |
| 122 | **CCG**GTTGGTCTGTT | LNA 3 + TEG | 168 |
| 123 | **GC**CGGTTGGTCT**GT** | LNA 2 + 2 | 137 |
| 123 | **GCC**GGTTGGTCTGT | LNA 3 + TEG | 169 |
| 124 | **AG**TTGGCATTGT**AC** | LNA 2 + 2 | 138 |
| 124 | **AGT**TGGCATTGTAC | LNA 3 + TEG | 170 |
| 125 | **GG**TTAGAGGTTC**TA** | LNA 2 + 2 | 139 |
| 125 | **GGT**TAGAGGTTCTA | LNA 3 + TEG | 171 |
| 126 | **AT**GGTTAGAGGT**TC** | LNA 2 + 2 | 140 |
| 126 | **ATG**GTTAGAGGTTC | LNA 3 + TEG | 172 |
| 127 | **AG**AATGGTTAGA**GG** | LNA 2 + 2 | 141 |
| 127 | **AGA**ATGGTTAGAGG | LNA 3 + TEG | 173 |
| 128 | **AG**AGAATGGTTA**GA** | LNA 2 + 2 | 142 |
| 128 | **AGA**GAATGGTTAGA | LNA 3 + TEG | 174 |
| 129 | **CG**TTGTCGTCGT**CA** | LNA 2 + 2 | 143 |

-continued

| SEQ ID NO. | Sequence (5'->3') | Modification | ASPH |
|---|---|---|---|
| 129 | **CGT**TGTCGTCGTC**A** | LNA 3 + TEG | 175 |
| 130 | **AC**CAAGGCTCTC**TT** | LNA 2 + 2 | 144 |
| 130 | **ACC**AAGGCTCTCT**T** | LNA 3 + TEG | 176 |
| 131 | **GC**TTCTTGTCTC**TC** | LNA 2 + 2 | 145 |
| 131 | **GCT**TCTTGTCTCT**C** | LNA 3 + TEG | 177 |
| 132 | **GG**AACGGTACGT**AC** | LNA 2 + 2 | 146 |
| 132 | **GGA**ACGGTACGTA**C** | LNA 3 + TEG | 178 |
| 133 | **TA**GGAACGGTAC**GT** | LNA 2 + 2 | 147 |
| 133 | **TAG**GAACGGTACG**T** | LNA 3 + TEG | 179 |
| 134 | **GG**GATAGGAACG**GT** | LNA 2 + 2 | 148 |
| 134 | **GGGA**TAGGAACGG**T** | LNA 3 + TEG | 180 |
| 135 | **CG**CGGGATAGGA**AC** | LNA 2 + 2 | 149 |
| 135 | **CGC**GGGATAGGAA**C** | LNA 3 + TEG | 181 |
| 136 | **AG**GCGCGGGATA**GG** | LNA 2 + 2 | 150 |
| 136 | **AGG**CGCGGGATAGG | LNA 3 + TEG | 182 |
| 137 | **GT**CAAGCTGGAT**GG** | LNA 2 + 2 | 151 |
| 137 | **GTC**AAGCTGGATG**G** | LNA 3 + TEG | 183 |
| 138 | **TC**TGTAGGAG**GGC** | ENA 2 + 3 | 184 |
| 139 | **GAC**CAGATGCA**GGA** | ENA 3 + 3 | 185 |
| 140 | **CTC**CTTGGCGTA**GTA** | ENA 3 + 3 | 186 |
| 141 | **CCT**CCTTGGCGTA**GTA** | ENA 3 + 3 | 187 |
| 142 | **CAGA**TGCCAGTTTT**AAC** | ENA 4 + 4 | 188 |
| 143 | **AGC**GTAATTGGTCA**TCA** | ENA 3 + 3 | 189 |
| 146 | **AGT**ATTTGGTC**TCC** | LNA 3 + 3 | 190 |
| 147 | **AAG**TATTTGGT**CTC** | LNA 3 + 3 | 191 |
| 148 | **AAG**TATTTGGTC**TCC** | LNA 3 + 3 | 192 |
| 149 | **CAA**AGTATTTGGTC**TCC** | LNA 3 + 3 | 193 |
| 150 | **AGC**TCGTCCCTCCT**CCC** | LNA 3 + 3 | 1000 |
| 151 | **GAG**GGCTGGTCCGG**AAT** | LNA 3 + 3 | 1001 |
| 152 | **CGA**GGGCTGGTCCG**GAA** | LNA 3 + 3 | 1002 |
| 153 | **GAG**GGCGGCATGGG**GGA** | LNA 3 + 3 | 1003 |
| 154 | **GCG**GGTGCTGTTGT**ACA** | LNA 3 + 3 | 1004 |
| 155 | **CGC**GGGTGCTGTTG**TAC** | LNA 3 + 3 | 1005 |
| 156 | **GTC**GCGGGTGCTGT**TGT** | LNA 3 + 3 | 1006 |
| 157 | **GGT**CGCGGGTGCTG**TTG** | LNA 3 + 3 | 1007 |
| 158 | **CCG**GTCGCGGGTGC**TGT** | LNA 3 + 3 | 1008 |
| 159 | **CCC**GGTCGCGGGTG**CTG** | LNA 3 + 3 | 1009 |
| 160 | **AGC**ACGCGGGTGAC**CTC** | LNA 3 + 3 | 1010 |

-continued

| SEQ ID NO. | Sequence (5'->3') | Modification | ASPH |
|---|---|---|---|
| 161 | **TTA**GCACGCGGGTG**ACC** | LNA 3 + 3 | 1011 |
| 162 | **GGG**CTCGTGGATCC**ACT** | LNA 3 + 3 | 1012 |
| 163 | **CCT**TGGGCTCGTGG**ATC** | LNA 3 + 3 | 1013 |
| 164 | **TGG**CATGGTAGCCC**TTG** | LNA 3 + 3 | 1014 |
| 165 | **CGA**GGGCTGGTCC**GGA** | LNA 3 + 3 | 1015 |
| 166 | **GCG**GGTGCTGTTG**TAC** | LNA 3 + 3 | 1016 |
| 167 | **GCA**CGCGGGTGAC**CTC** | LNA 3 + 3 | 1017 |
| 168 | **CCT**TGGGCTCGTG**GAT** | LNA 3 + 3 | 1018 |
| 169 | **GGC**ATGGTAGCCC**TTG** | LNA 3 + 3 | 1019 |
| 170 | **GGG**TGCTGTTG**TAC** | LNA 3 + 3 | 1020 |
| 171 | **TCG**CGGGTGCT**GTT** | LNA 3 + 3 | 1021 |
| 172 | **GTC**GCGGGTGC**TGT** | LNA 3 + 3 | 1022 |
| 173 | **CTC**GTGGATCC**ACT** | LNA 3 + 3 | 1023 |
| 174 | **ATG**GTAGCCCT**TGG** | LNA 3 + 3 | 1024 |
| 175 | **TGG**CATGGTAG**CCC** | LNA 3 + 3 | 1025 |
| 176 | **GAA**GTTGGCAT**GGT** | LNA 3 + 3 | 1026 |
| 177 | **TC**GCGGGTGC**TGT** | LNA 2 + 3 | 1027 |
| 178 | **CA**CCCGGTCG**CGG** | LNA 2 + 3 | 1028 |
| 179 | **CC**ACCCGGTC**GCG** | LNA 2 + 3 | 1029 |
| 180 | **CG**CCAGGAAT**TGT** | LNA 3 + 2 | 1030 |
| 181 | **GG**CTCGTGGA**TCC** | LNA 2 + 3 | 1031 |
| 182 | **TG**GGCTCGTG**GAT** | LNA 2 + 3 | 1032 |
| 183 | **GC**ATGGTAGC**CCT** | LNA 2 + 3 | 1033 |
| 184 | **AG**TTGGCATG**GTA** | LNA 2 + 3 | 1034 |
| 185 | **TT**GCAGGAGC**GCA** | LNA 2 + 3 | 1035 |
| 186 | **ATT**AGCACGCGGGT**GAC** | LNA 3 + 3 | 1036 |
| 187 | **ACC**ATTAGCACGCG**GGT** | LNA 3 + 3 | 1037 |
| 188 | **CAC**CATTAGCACGC**GGG** | LNA 3 + 3 | 1038 |
| 189 | **CCA**CCATTAGCACG**CGG** | LNA 3 + 3 | 1039 |
| 190 | **TCC**ACCATTAGCAC**GCG** | LNA 3 + 3 | 1040 |
| 191 | **TCC**ACCTTGGGCTT**GCG** | LNA 3 + 3 | 1041 |
| 192 | **TTA**GCACGCGGGT**GAC** | LNA 3 + 3 | 1042 |
| 193 | **ACC**ATTAGCACGC**GGG** | LNA 3 + 3 | 1043 |
| 194 | **CAC**CATTAGCACG**CGG** | LNA 3 + 3 | 1044 |
| 195 | **CAC**CATTAGCAC**GCG** | LNA 3 + 3 | 1045 |
| 196 | **GCG**GCACGCAGC**ACG** | LNA 3 + 3 | 1046 |
| 197 | **TCG**ATGCGCTT**CCG** | LNA 3 + 3 | 1047 |

-continued

| SEQ ID NO. | Sequence (5'->3') | Modification | ASPH |
|---|---|---|---|
| 198 | **TAG**CACGCGGG**TGA** | LNA 3 + 3 | 1048 |
| 199 | **ATT**AGCACGCG**GGT** | LNA 3 + 3 | 1049 |
| 200 | **CAT**TAGCACGC**GGG** | LNA 3 + 3 | 1050 |
| 201 | **ACC**ATTAGCAC**GCG** | LNA 3 + 3 | 1051 |
| 202 | **CAC**CATTAGCA**CGC** | LNA 3 + 3 | 1052 |
| 203 | **CCA**CCATTAGC**ACG** | LNA 3 + 3 | 1053 |
| 204 | **TCC**ACCATTAG**CAC** | LNA 3 + 3 | 1054 |
| 205 | **GAC**CTTGCTGT**ACT** | LNA 3 + 3 | 1055 |
| 206 | **GGA**CCTTGCTG**TAC** | LNA 3 + 3 | 1056 |
| 207 | **AGG**ACCTTGCT**GTA** | LNA 3 + 3 | 1057 |
| 208 | **CGG**CACGCAGC**ACG** | LNA 3 + 3 | 1058 |
| 209 | **ACC**TTGGGCTT**GCG** | LNA 3 + 3 | 1059 |
| 210 | **TTA**GCACGCGG**GT** | LNA 3 + 2 | 1060 |
| 211 | **ACC**ATTAGCAC**GC** | LNA 3 + 2 | 1061 |
| 212 | **CGG**CACGCAGC**AC** | LNA 3 + 2 | 1062 |
| 213 | **CAC**CAGCTCCATGT**CGA** | LNA 3 + 3 | 1063 |
| 214 | **TCG**CGGGTGCTGTT**GTA** | LNA 3 + 3 | 1064 |
| 215 | **GTG**TCCAGGCTCCA**AAT** | LNA 3 + 3 | 1065 |
| 215 | **GTGT**CCAGGCTCCAA**AT** | LNA 4 + 2 | 1066 |
| 216 | **GCT**CGTCCCTCCT**CCC** | LNA 3 + 3 | 1067 |
| 217 | **ACC**AGCTCGTCCC**TCC** | LNA 3 + 3 | 1068 |
| 218 | **GGA**GGCCCCGCCC**CTG** | LNA 3 + 3 | 1069 |
| 219 | **CAT**GGGGGAGGCG**GCG** | LNA 3 + 3 | 1070 |
| 219 | **CAT**GGGGGAGGC**G**G**CG** | 3LNA + 9N + 1LNA + 1N + 2LNA | 1071 |
| 220 | **ACC**AGCTCCATGT**CGA** | LNA 3 + 3 | 1072 |
| 221 | **GGT**CGCGGGTGCT**GTT** | LNA 3 + 3 | 1073 |
| 222 | **GGA**CCTTGCTGTA**CTG** | LNA 3 + 3 | 1074 |
| 222 | **GGA**CCTTGCTGTAC**TG** | LNA 4 + 2 | 1075 |
| 223 | **TCC**ACCTTGGGCT**TGC** | LNA 3 + 3 | 1076 |
| 224 | **AGC**TCGTCCCTC**CTC** | LNA 3 + 3 | 1077 |
| 225 | **CCA**GCTCGTCCC**TCC** | LNA 3 + 3 | 1078 |
| 226 | **GAG**GGCTGGTCC**GGA** | LNA 3 + 3 | 1079 |
| 227 | **TCC**CGAGGGCTG**GTC** | LNA 3 + 3 | 1080 |
| 228 | **CG**GCATGGGGG**AGGC** | LNA 2 + 4 | 1081 |
| 229 | **CAG**CTCCATGTC**GAT** | LNA 3 + 3 | 1082 |
| 230 | **ACC**AGCTCCATG**TCG** | LNA 3 + 3 | 1083 |
| 231 | **TCG**CGGGTGCTG**TTG** | LNA 3 + 3 | 1084 |

-continued

| SEQ ID NO. | Sequence (5'->3') | Modification | ASPH |
|---|---|---|---|
| 232 | **GTC**GCGGGTGCT**GTT** | LNA 3 + 3 | 1085 |
| 233 | **GGT**CGCGGGTGC**TGT** | LNA 3 + 3 | 1086 |
| 234 | **AG**CACGCGGGTG**ACC** | LNA 3 + 3 | 1087 |
| 235 | **TAG**CACGCGGGT**GAC** | LNA 3 + 3 | 1088 |
| 236 | **CAT**TAGCACGCG**GGT** | LNA 3 + 3 | 1089 |
| 237 | **TCC**ACCATTAGC**ACG** | LNA 3 + 3 | 1090 |
| 238 | **CCAG**GAATTGTTG**CT** | LNA 4 + 2 | 1091 |
| 239 | **TTG**GGCTCGTGG**ATC** | LNA 3 + 3 | 1092 |
| 240 | **CTT**GGGCTCGTG**GAT** | LNA 3 + 3 | 1093 |
| 241 | **TTG**GCATGGTAG**CCC** | LNA 3 + 3 | 1094 |
| 242 | **GAA**GTTGGCATG**GTA** | LNA 3 + 3 | 1095 |
| 243 | **AGA**AGTTGGCAT**GGT** | LNA 3 + 3 | 1096 |
| 244 | **TGTC**CAGGCTCCA**AA** | LNA 4 + 2 | 1097 |
| 245 | **AGG**ACCTTGCTG**TAC** | LNA 3 + 3 | 1098 |
| 246 | **CACC**TTGGGCTTG**CG** | LNA 4 + 2 | 1099 |
| 246 | **C**A**CC**TTGGGCTT**G**C**G** | 1LNA + 1N + 2LNA + 8N + 1LNA + 1N + 1LNA | 1100 |
| 247 | **AGC**TCGTCCCT**CCT** | LNA 3 + 3 | 1101 |
| 248 | **CAG**CTCGTCCC**TCC** | LNA 3 + 3 | 1102 |
| 249 | **ACC**AGCTCGTC**CCT** | LNA 3 + 3 | 1103 |
| 250 | **CCC**GAGGGCTG**GTC** | LNA 3 + 3 | 1104 |
| 251 | **GC**GGCATGGG**GGAG** | LNA 2 + 4 | 1105 |
| 252 | **GTC**TTGCAGGT**GGA** | LNA 3 + 3 | 1106 |
| 253 | **TC**GATGCGCT**TC**CG | LNA 2 + 4 | 1107 |
| 253 | **TC**GATGCGCTT**CCG** | LNA 2 + 3 | 1108 |
| 253 | **TC**GATGCGCT**TC**C**G** | 2LNA + 8N + 2LNA + 1N + 1LNA | 1109 |
| 253 | **TC**GATGCGCTT**C**C**G** | 2LNA + 9N + 1LNA + 1N + 1LNA | 1110 |
| 253 | **TC**GATGCGCT**T**CC**G** | 2LNA + 8N + 1LNA + 2N + 1LNA | 1111 |
| 254 | **GGAC**AGGATCTG**GC** | LNA 4 + 2 | 1112 |
| 255 | **ACC**TCCCCCTG**GCT** | LNA 3 + 3 | 1113 |
| 256 | **ACC**ATTAGCACG**CG** | LNA 4 + 2 | 1114 |
| 256 | **ACC**ATTAGCAC**G**C**G** | 3LNA + 8N + 1LNA + 1N + 1LNA | 1115 |
| 257 | **CA**GCAGTTCT**TCTC** | LNA 2 + 4 | 1116 |
| 258 | **TAC**AGCTGCCG**CAC** | LNA 3 + 3 | 1117 |
| 259 | **AGT**TGGCATGG**TAG** | LNA 3 + 3 | 1118 |
| 259 | **AGTT**GGCATGGT**AG** | LNA 4 + 2 | 1119 |

-continued

| SEQ ID NO. | Sequence (5'->3') | Modification | ASPH |
|---|---|---|---|
| 260 | **AAG**TTGGCATG**GTA** | LNA 3 + 3 | 1120 |
| 261 | **GAAG**TTGGCATG**GT** | LNA 4 + 2 | 1121 |
| 262 | **TCC**AGGCTCCA**AAT** | LNA 3 + 3 | 1122 |
| 263 | **ACC**TTGCTGTA**CTG** | LNA 3 + 3 | 1123 |
| 263 | **ACCT**TGGGCTTG**CG** | LNA 4 + 2 | 1124 |
| 263 | **ACC**TTGGGCTTG**CG** | LNA 3 + 2 | 1125 |
| 263 | **ACC**TTGGGCTT**G**C**G** | 3LNA + 8N + 1LNA + 1N + 1LNA | 1126 |
| 263 | **AC**CTTGGGCTT**G**C**G** | 2LNA + 9N + 1LNA + 1N + 1LNA | 1127 |
| 263 | **AC**CTTGGGCT**TG**C**G** | 2LNA + 8N + 2LNA + 1N + 1LNA | 1128 |
| 264 | **TTG**CAGGAGCG**CAC** | LNA 3 + 3 | 1129 |
| 265 | **GCAG**AAGTTGGC**AT** | LNA 4 + 2 | 1130 |
| 266 | **CGG**GTGCTGTT**GTA** | LNA 3 + 3 | 1131 |
| 266 | **CG**GGTGCTGT**TGTA** | LNA 2 + 4 | 1132 |
| 267 | **CCC**AGCGGCAACGG**AAA** | LNA 3 + 3 | 1133 |
| 268 | **CAA**GAGGTCCCCGC**GCC** | LNA 3 + 3 | 1134 |
| 269 | **GCG**TCCCCGGCGGC**AAA** | LNA 3 + 3 | 1135 |
| 270 | **GGT**CGGCGACTCCC**GAG** | LNA 3 + 3 | 1136 |
| 271 | **TCG**GAGAGAGATCC**GTC** | LNA 3 + 3 | 1137 |
| 272 | **ATC**CCACGGAAATA**ACC** | LNA 3 + 3 | 1138 |
| 273 | **CTC**AGTATCCCACG**GAA** | LNA 3 + 3 | 1139 |
| 274 | **ACT**GCCGAGAGCGC**GAA** | LNA 3 + 3 | 1140 |
| 275 | **CTG**ATGTGTTGAAG**AAC** | LNA 3 + 3 | 1141 |
| 276 | **TGA**GGTATCGCCAG**GAA** | LNA 3 + 3 | 1142 |
| 277 | **ACT**GCCGCACAACT**CCG** | LNA 3 + 3 | 1143 |
| 278 | **CGG**CCCACGTAGTA**CAC** | LNA 3 + 3 | 1144 |
| 279 | **CCC**AGCGGCAACG**GAA** | LNA 3 + 3 | 1145 |
| 280 | **TCG**CGCCAAGAGG**TCC** | LNA 3 + 3 | 1146 |
| 281 | **GGT**CGGCGACTCC**CGA** | LNA 3 + 3 | 1147 |
| 282 | **GTC**GGAGAGAGAT**CCG** | LNA 3 + 3 | 1148 |
| 283 | **TCA**GTATCCCACG**GAA** | LNA 3 + 3 | 1149 |
| 284 | **CGA**GAGCGCGAAC**AGG** | LNA 3 + 3 | 1150 |
| 285 | **ACT**GCCGAGAGCG**CGA** | LNA 3 + 3 | 1151 |
| 286 | **GGC**GTCAGCACCA**GTA** | LNA 3 + 3 | 1152 |
| 287 | **GGT**TTCCACCATT**AGC** | LNA 3 + 3 | 1153 |
| 288 | **GAG**GTATCGCCAG**GAA** | LNA 3 + 3 | 1154 |
| 289 | **AAC**CACTGCCGCA**CAA** | LNA 3 + 3 | 1155 |
| 290 | **CGG**CCCACGTAGT**ACA** | LNA 3 + 3 | 1156 |
| 291 | **CGG**CGGCTCGTC**TCA** | LNA 3 + 3 | 1157 |
| 292 | **CCC**AGCGGCAAC**GGA** | LNA 3 + 3 | 1158 |
| 293 | **TCG**CGCCAAGAG**GTC** | LNA 3 + 3 | 1159 |
| 294 | **CGT**CGCGCCAAG**AGG** | LNA 3 + 3 | 1160 |
| 295 | **GGA**GCAAGCGTC**CCC** | LNA 3 + 3 | 1161 |
| 296 | **GTG**CGCCCGAGG**TCT** | LNA 3 + 3 | 1162 |
| 297 | **GTC**TAGGATGCG**CGG** | LNA 3 + 3 | 1163 |
| 298 | **CAG**TATCCCACG**GAA** | LNA 3 + 3 | 1164 |
| 299 | **CCG**AGAGCGCGA**ACA** | LNA 3 + 3 | 1165 |
| 300 | **GGC**GTCAGCACC**AGT** | LNA 3 + 3 | 1166 |
| 301 | **GTT**GCTGAGGTA**TCG** | LNA 3 + 3 | 1167 |
| 302 | **ACC**ACTGCCGCA**CAA** | LNA 3 + 3 | 1168 |
| 303 | **CGG**CCCACGTAG**TAC** | LNA 3 + 3 | 1169 |
| 304 | **CTC**GGCGACTC**CTT** | LNA 3 + 3 | 1170 |
| 305 | **AGC**GGCAACGG**AAA** | LNA 3 + 3 | 1171 |
| 306 | **TCG**CGCCAAGA**GGT** | LNA 3 + 3 | 1172 |
| 307 | **TCC**CCGGCGGC**AAA** | LNA 3 + 3 | 1173 |
| 308 | **TGC**GCCCGAGG**TCT** | LNA 3 + 3 | 1174 |
| 309 | **GTC**TAGGATGC**GCG** | LNA 3 + 3 | 1175 |
| 310 | **GGT**CGGAGAGA**GAT** | LNA 3 + 3 | 1176 |
| 311 | **CAC**GGAAATAA**CCT** | LNA 3 + 3 | 1177 |
| 312 | **AGA**GCGCGAAC**AGG** | LNA 3 + 3 | 1178 |
| 313 | **ATA**GTCCCGCG**GCC** | LNA 3 + 3 | 1179 |
| 314 | **TAG**TAGTCGGC**CTC** | LNA 3 + 3 | 1180 |
| 315 | **ATA**GATTTCGT**TGT** | LNA 3 + 3 | 1181 |
| 316 | **GAG**GTATCGCC**AGG** | LNA 3 + 3 | 1182 |
| 317 | **GCC**GCACAACT**CCG** | LNA 3 + 3 | 1183 |
| 318 | **TC**GCGCCAAG**AGG** | LNA 2 + 3 | 1184 |
| 319 | **AAG**CGTCCCCG**GC** | LNA 3 + 2 | 1185 |
| 320 | **GAC**GCCGTGTA**GG** | LNA 3 + 2 | 1186 |
| 321 | **GT**CGGCGACT**CCC** | LNA 2 + 3 | 1187 |
| 322 | **TGC**GCCCGAGG**TC** | LNA 3 + 2 | 1188 |
| 323 | **GTC**GGAGAGAG**AT** | LNA 3 + 2 | 1189 |
| 324 | **TCC**CACGGAAA**TA** | LNA 3 + 2 | 1190 |
| 325 | **TG**CCGAGAGC**GCG** | LNA 2 + 3 | 1191 |
| 326 | **TAG**TCCCGCGG**CC** | LNA 3 + 2 | 1192 |

| SEQ ID NO. | Sequence (5'->3') | Modification | ASPH |
|---|---|---|---|
| 327 | TAGTAGTCGGCCT | LNA 3 + 2 | 1193 |
| 328 | CATAGATTTCGTT | LNA 2 + 3 | 1194 |
| 329 | TTTAACTTGAGCC | LNA 3 + 2 | 1195 |
| 330 | GAGGTATCGCCAG | LNA 3 + 2 | 1196 |
| 331 | ACTCCGGTGACAT | LNA 2 + 3 | 1197 |
| 332 | GCCCACGTAGTAC | LNA 2 + 3 | 1198 |
| 333 | TCGGCGACTCCC | LNA 2 + 2 | 1199 |
| 334 | GTCGGCGACTCC | LNA 2 + 2 | 1200 |
| 337 | CAGGAAGCGCTGGCAAC | LNA 3 + 3 | 2000 |
| 338 | GGTGCATGAACTCACTG | LNA 3 + 3 | 2001 |
| 339 | GTCCCCTAATGGCTTCC | LNA 3 + 3 | 2002 |
| 340 | ATCTGTCCCCTAATGGC | LNA 3 + 3 | 2003 |
| 341 | CCGGGTGCTGTTGTAAA | LNA 3 + 3 | 2004 |
| 342 | CCTGGATCATGTCGAAT | LNA 3 + 3 | 2005 |
| 343 | CCCTGGATCATGTCGAA | LNA 3 + 3 | 2006 |
| 344 | GTAGCACCTGCTTCCAG | LNA 3 + 3 | 2007 |
| 345 | GGGCTTTCTAAATGAC | LNA 3 + 3 | 2008 |
| 346 | TGACTCCCAGCAGGCC | LNA 3 + 3 | 2009 |
| 347 | GTGCATGAACTCACTG | LNA 3 + 3 | 2010 |
| 348 | GGTGCATGAACTCACT | LNA 3 + 3 | 2011 |
| 349 | ATCTGTCCCCTAATGG | LNA 3 + 3 | 2012 |
| 350 | CGGGTGCTGTTGTAAA | LNA 3 + 3 | 2013 |
| 351 | CCGGGTGCTGTTGTAA | LNA 3 + 3 | 2014 |
| 352 | CCTGGATCATGTCGAA | LNA 3 + 3 | 2015 |
| 353 | CCCTGGATCATGTCGA | LNA 3 + 3 | 2016 |
| 354 | TTTGAATTTGATTTCC | LNA 3 + 3 | 2017 |
| 355 | GGGCCTGAGCAGAAGT | LNA 3 + 3 | 2018 |
| 356 | GGGGGCTTTCTAAAT | LNA 3 + 3 | 2019 |
| 357 | TTTGTTTACACTTCC | LNA 3 + 3 | 2020 |
| 358 | CCAGCTAAAGGTGGG | LNA 3 + 3 | 2021 |
| 359 | ATGGCTGGGTCCCAA | LNA 3 + 3 | 2022 |
| 360 | GAGTTTTTCCTTAGG | LNA 3 + 3 | 2023 |
| 361 | AGGGGTGGCAAGGCA | LNA 3 + 3 | 2024 |
| 362 | TGACTCCCAGCAGGC | LNA 3 + 3 | 2025 |
| 363 | GAAGCGCTGGCAACC | LNA 3 + 3 | 2026 |
| 364 | GTGCATGAACTCACT | LNA 3 + 3 | 2027 |
| 365 | GTGGTGCAAGTGGAC | LNA 3 + 3 | 2028 |
| 366 | CTAATGGCTTCCACC | LNA 3 + 3 | 2029 |
| 367 | CCCCTAATGGCTTCC | LNA 3 + 3 | 2030 |
| 368 | ATCTGTCCCCTAATG | LNA 3 + 3 | 2031 |
| 369 | GATCTGTCCCCTAAT | LNA 3 + 3 | 2032 |
| 370 | AGATCTGTCCCCTAA | LNA 3 + 3 | 2033 |
| 371 | GGTGCTGTTGTAAAG | LNA 3 + 3 | 2034 |
| 372 | CCGGGTGCTGTTGTA | LNA 3 + 3 | 2035 |
| 373 | GATCATGTCGAATTT | LNA 3 + 3 | 2036 |
| 374 | CCTGGATCATGTCGA | LNA 3 + 3 | 2037 |
| 375 | CCCTGGATCATGTCG | LNA 3 + 3 | 2038 |
| 376 | GATTTCCATCACCTC | LNA 3 + 3 | 2039 |
| 377 | TTGAATTTGATTTCC | LNA 3 + 3 | 2040 |
| 378 | AGCAGTTCTCCTCCA | LNA 3 + 3 | 2041 |
| 379 | GCCTGAGCAGAAGTT | LNA 3 + 3 | 2042 |
| 380 | GGGCAAGGGCCTGAG | LNA 3 + 3 | 2043 |
| 381 | CCCACACTTTCTTTA | LNA 3 + 3 | 2044 |
| 382 | TAGCACCTGCTTCCA | LNA 3 + 3 | 2045 |
| 383 | CGGGGGCTTTCTAA | LNA 3 + 3 | 2046 |
| 384 | CCATTCATGCTTTC | LNA 3 + 3 | 2047 |
| 385 | AAGCGCTGGCAACC | LNA 3 + 3 | 2048 |
| 386 | ACCAGAGCCCTTTG | LNA 3 + 3 | 2049 |
| 387 | CCCCTAATGGCTTC | LNA 3 + 3 | 2050 |
| 388 | GTCCCCTAATGGCT | LNA 3 + 3 | 2051 |
| 389 | ATCTGCCCCTAAT | LNA 3 + 3 | 2052 |
| 390 | AGATCTGTCCCCTA | LNA 3 + 3 | 2053 |
| 391 | CGGGTGCTGTTGTA | LNA 3 + 3 | 2054 |
| 392 | ATCATGTCGAATTT | LNA 3 + 3 | 2055 |
| 393 | CCCTGGATCATGTC | LNA 3 + 3 | 2056 |
| 394 | CCTTTGAATTTGAT | LNA 3 + 3 | 2057 |
| 395 | TTGCGGAAGCAGTA | LNA 3 + 3 | 2058 |
| 396 | GCCTGAGCAGAAGT | LNA 3 + 3 | 2059 |
| 397 | GGGGGCTTTCTAA | LNA 2 + 3 | 2060 |
| 398 | AGCGCTGGCAACC | LNA 2 + 3 | 2061 |
| 399 | CCCCTAATGGCTT | LNA 2 + 3 | 2062 |
| 399 | CCCCTAATGGCTT | LNA 3 + 2 | 2063 |
| 400 | TCCCCTAATGGCT | LNA 3 + 2 | 2064 |
| 401 | TCATGTCGAATTT | LNA 2 + 3 | 2065 |
| 402 | ATCATGTCGAATT | LNA 3 + 2 | 2066 |

Table 1 shows the nucleic acid sequences of selected oligonucleotides of the present invention as well as the modifications of the nucleotides, wherein LNA 4+4 means 4×LNAs at the 5'- and 3'-end of the oligonucleotide are modified, wherein LNA 4+3 means 4×LNAs at the 5'-end and 3×LNAs at the 3'-end of the oligonucleotide are modified, wherein LNA 3+4 means 3×LNAs at the 5'-end and 4×LNAs at the 3'-end of the oligonucleotide are modified, wherein LNA 3+3 means 3×LNAs at the 5'- and 3'-end of the oligonucleotide are modified, wherein LNA 3+2 means 3×LNAs at the 5'-end and 2×LNAs at the 3'-end of the oligonucleotide are modified, wherein LNA 2+3 means 2×LNAs at the 5'-end and 3×LNAs at the 3'-end of the oligonucleotide are modified, wherein LNA 2+2 means 2×LNAs at the 5'- and 3'-end of the oligonucleotide are modified. Alternatively, some oligonucleotides comprise ENA 4+4, i.e., 4×ENA at the 5'- and 3'-end of the oligonucleotide are modified, or ENA 3+3, i.e, 3×ENA at the 5'- and 3'-end of the oligonucleotide are modified. Further oligonucleotides comprise 2'O-meth 4+4, wherein the oligonucleotide comprises 4×2'O-methyl modified nucleotides at the 5'- and 3'-end of the oligonucleotide, or comprises 2' fluoro 4+4, wherein the oligonucleotide comprises 4×2'fluoro modified nucleotides at the 5'- and 3'-end. Oligonucleotides comprising LNA 3+TEG comprise 3×LNAs at the 5'-end and one triethylene glycol (TEG) at the 3'-end of the oligonucleotide. Some oligonucleotides comprise LNAs which are not arranged in a row but are separated by an unlocked nucleoside having for example the sequences 3LNA+9N+1LNA+1N+2LNA, 1LNA+1N+2LNA+8N+1LNA+1N+1LNA, 2LNA+8N+2LNA+1N+1LNA, 2LNA+9N+1LNA+1N+1LNA, 2LNA+8N+1LNA+2N+1LNA, 3 LNA+8N+1LNA+1N+1LNA, 3 LNA+8N+1LNA+1N+1LNA, 2LNA+9N+1LNA+1N+1LNA, or 2LNA+8N+2LNA+1N+1LNA, wherein "N" is a nucleoside without locked modification. "ASPH" in combination with a number refers to the different oligonucleotides and their different modifications as described in Table 1. These modified oligonucleotides were tested e.g. in experiments shown in the following examples. The antisense oligonucleotides of the present invention can be described differently, e.g., ASPH47, ASPH0047, ASPH_47 or ASPH_0047 referring to the same oligonucleotide.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

In the following examples, the effect of the oligonucleotides listed in Table 1 has been tested in view of the reduction and inhibition, respectively, of TGF-beta1 and/or TGF-beta2 expression. SEQ ID NO. 144 (T-LNA: CGGCATGTCTATTTTGTA, wherein 3× nucleotides at the 5'- and 3'-end are LNAs) and SEQ ID NO. 145 (scr-LNA: CGTTTAGGCTATGTACTT, wherein 3× nucleotides at the 5'- and 3'-end are LNAs) are used as control oligonucleotides, wherein SEQ ID NO. 145 (negative control) is the scrambled form of SEQ ID NO. 144 (positive control). The cells were either transfected in the presence of a transfecting agent (e.g., Lipofectamine), or in the absence of any transfecting agent (which is defined as gymnotic transfection or unassisted transfection or gymnotic delivery). In case of gymnotic delivery the entry of the oligonucleotide into the cell solely depends on the interaction of the oligonucleotide with the cell (no compound/agent supports the entry). Therefore, gymnotic transfection or gymnotic delivery is considered to reflect better conditions of the in vivo settings.

Example 1

Figure 3B:
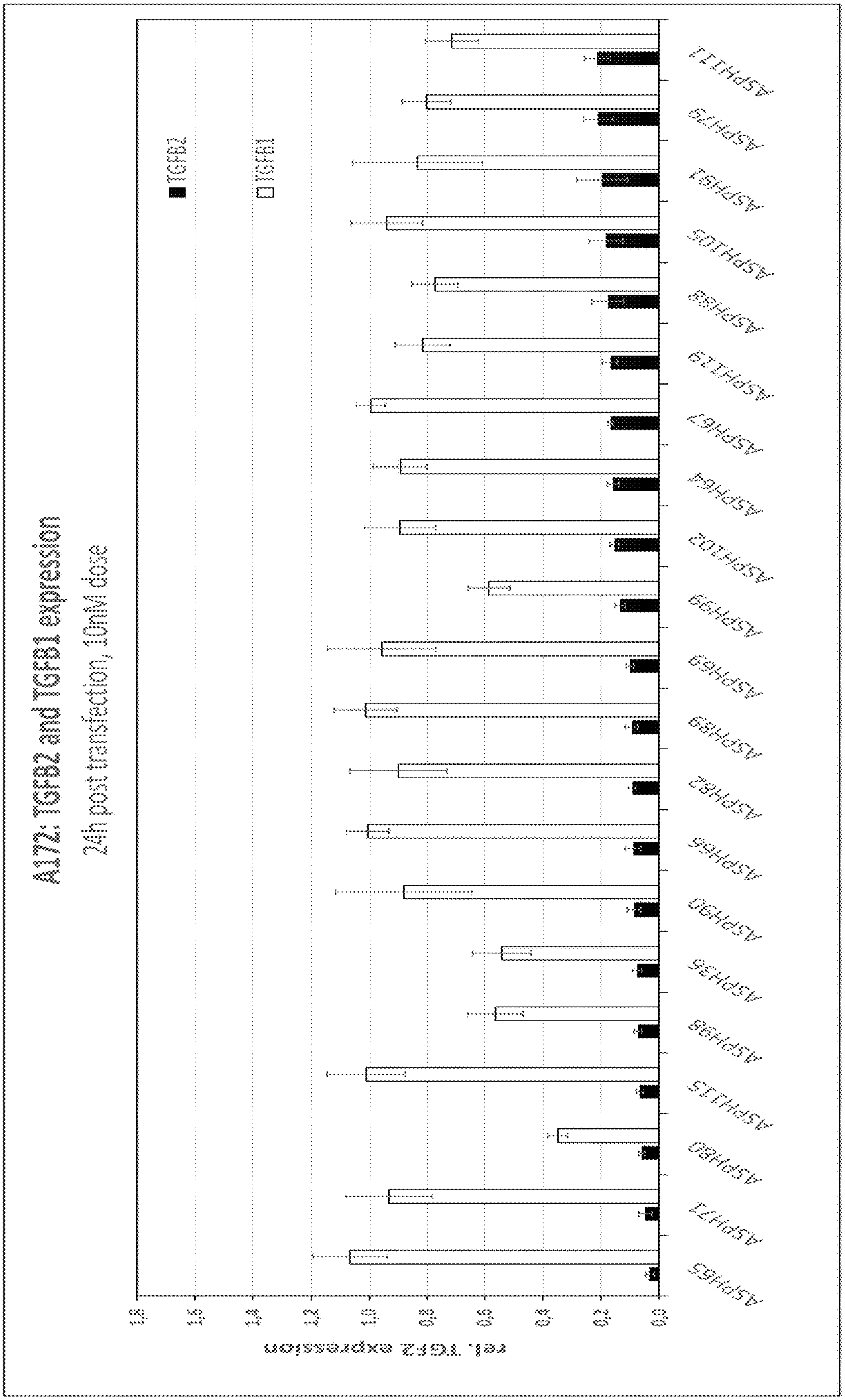
FIG. 3*b*(*i*), FIG. 3*b*(*ii*), FIG. 3*b*(*iii*)) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119.
Figure 3C:
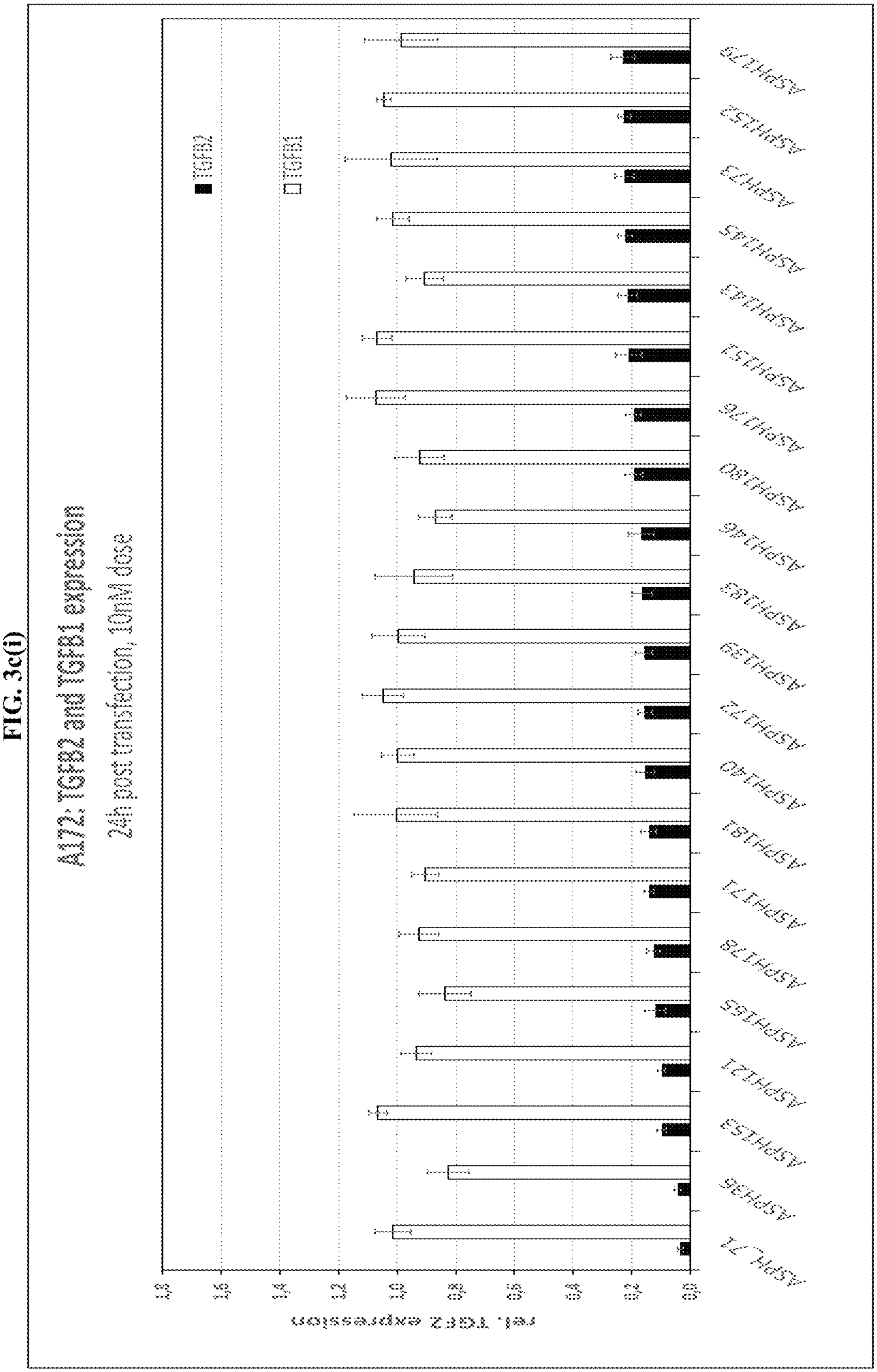
FIG. 3*c*(*i*), FIG. 3*c*(*ii*), FIG. 3*c*(*iii*)) to the results for the modified oligonucleotides ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 1.

Human A172 glioma cells were transfected with 10 nM of ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54 (see FIG. 3*a*(*i*), FIG. 3*a*(*ii*), FIG. 3*a*(*iii*)); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 3*b*(*i*), FIG. 3*b*(*ii*), FIG. 3*b*(*iii*)), or ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 3*c*(*i*), FIG. 3*c*(*ii*), FIG. 3*c*(*iii*)), and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in FIG. 3*a*(*i*), FIG. 3*a*(*ii*), FIG. 3*a*(*iii*), FIG. 3*b*(*i*), FIG. 3*b*(*ii*), FIG. 3*b*(*iii*), and FIG. 3*c*(*i*), FIG. 3*c*(*ii*), FIG. 3*c*(*iii*). The dual TGF-beta1 and TGF-beta2 reactive oligonucleotides ASPH01, ASPH02, ASPH03, ASPH04, ASPH05, ASPH06, ASPH07, ASPH08 and ASPH09 show a significant reduction of the expression of both TGF-beta1 and TGF-beta2 mRNA, while the selective TGF-beta2 oligonucleotides significantly inhibit TGF-beta2 mRNA expression.

Example 2

Figure 4A:
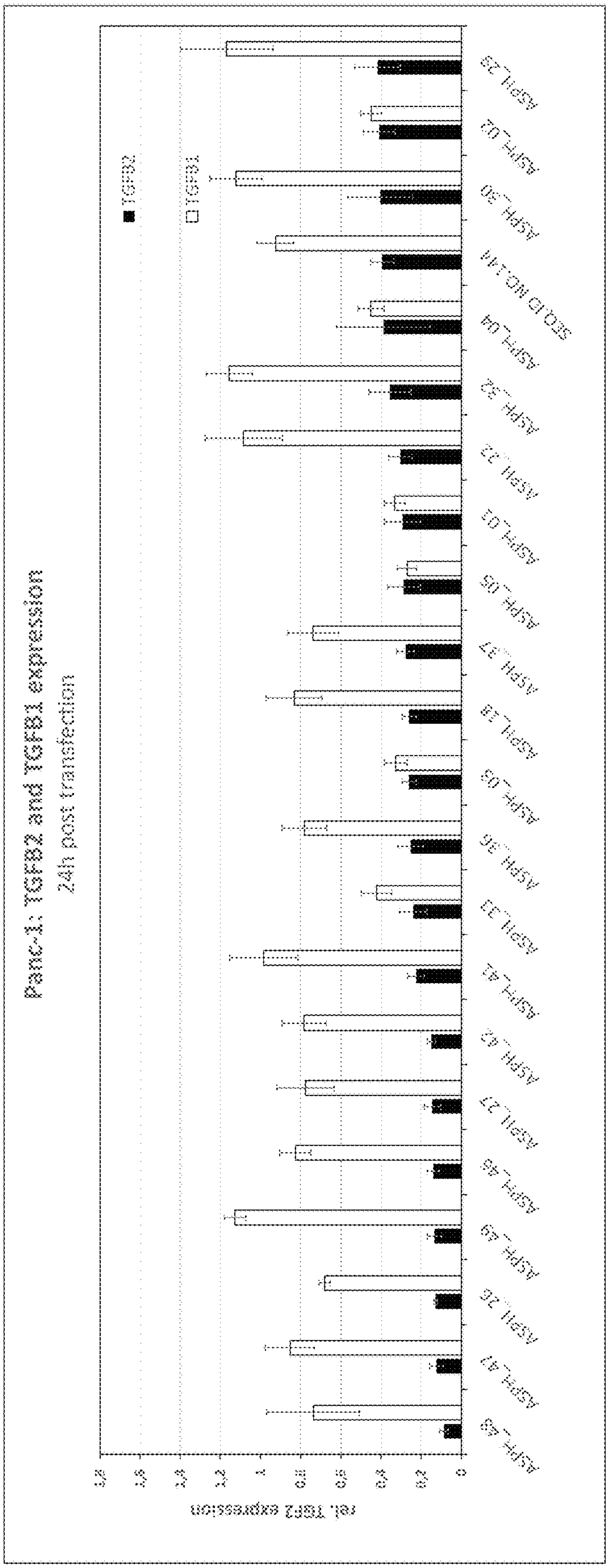
FIG. 4*a*(*i*), FIG. 4*a*(*ii*), FIG. 4*b*(*i*), FIG. 4*b*(*ii*), FIG. 4*b*(*iii*), and FIG. 4*c*(*i*), FIG. 4*c*(*ii*), and FIG. 4*c*(*iii*) depict the inhibition of the expression of TGF-beta1 and TGF-beta2 mRNA in human Panc-1 pancreatic cancer cells. Panc-1 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection.
Figure 4B:
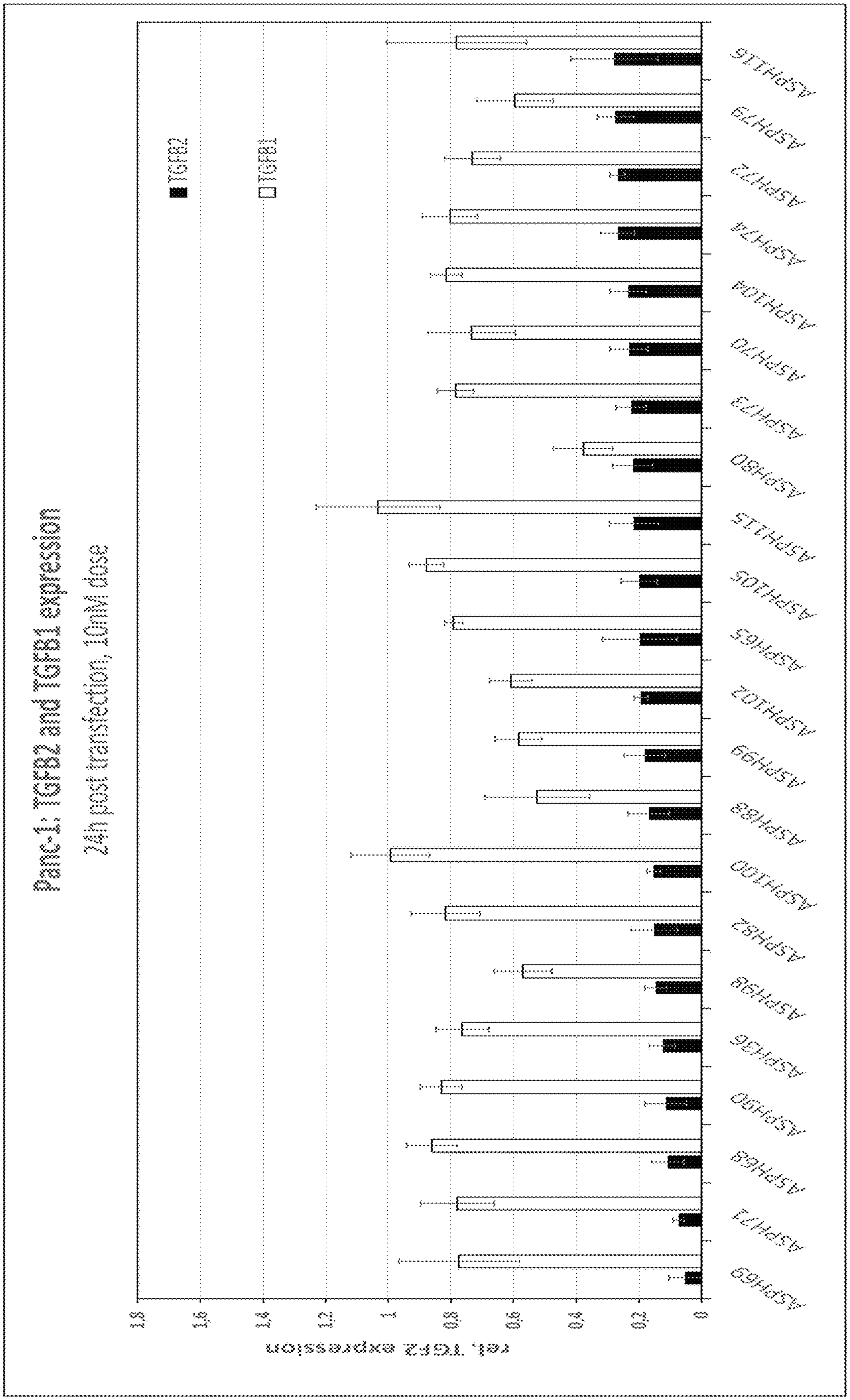
FIG. 4b(i), FIG. 4b(ii), and FIG. 4b(iii)) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119.
Figure 4C:
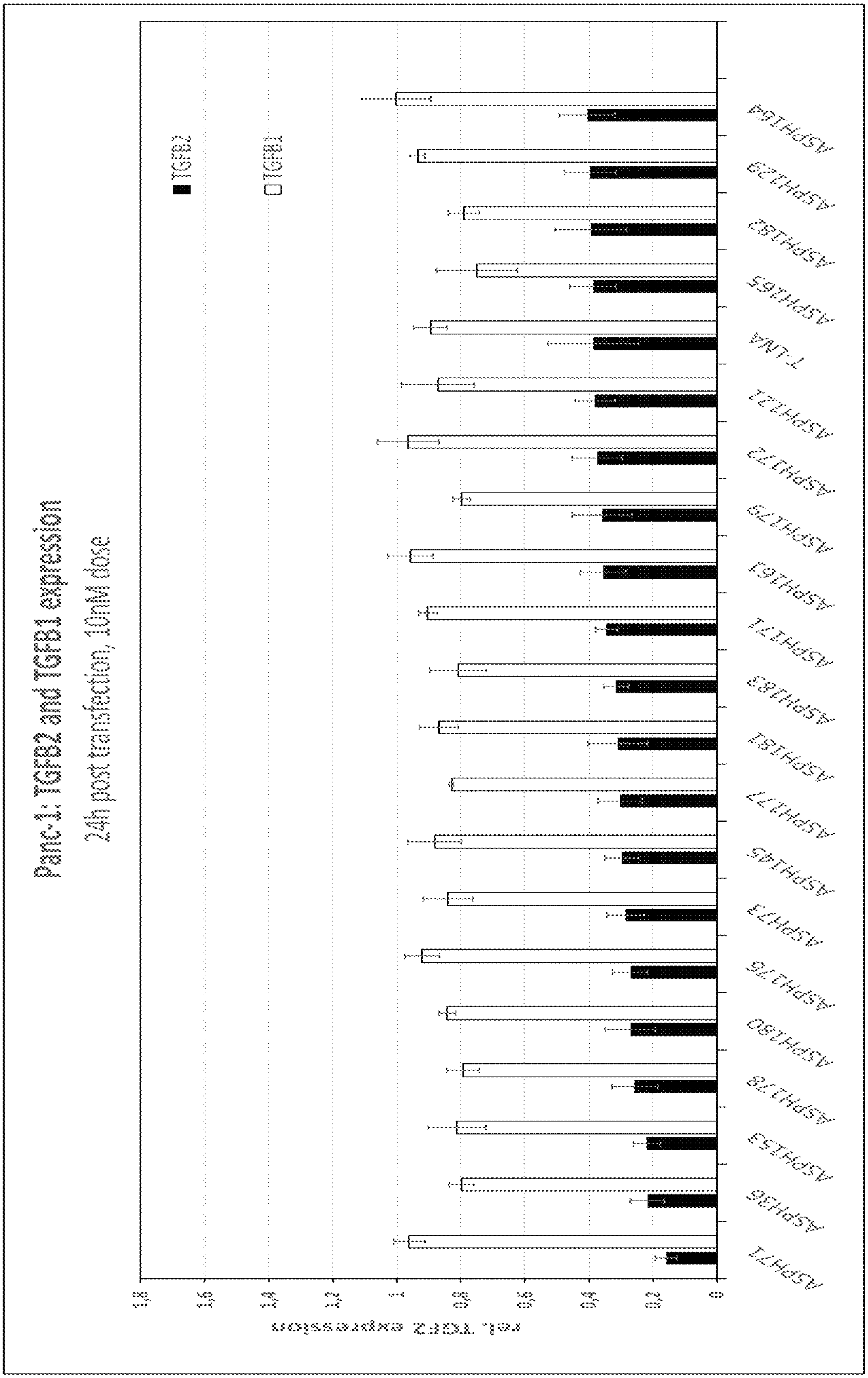
FIG. 4c(i), FIG. 4c(ii), and FIG. 4c(iii)) to the results for the modified oligonucleotides ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 2.

Human Panc-1 pancreatic cancer cells were transfected with 10 nM of ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52 (see FIG. 4*a*(*i*), and FIG. 4*a*(*ii*); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 4*b*(*i*), FIG. 4*b*(*ii*), and FIG. 4*b*(*iii*), or ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 4*c*(*i*), FIG. 4*c*(*ii*), and FIG. 4*c*(*iii*)) and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in 4*a*(*i*), FIG. 4*a*(*ii*), FIG. 4*b*(*i*), FIG. 4*b*(*ii*), FIG. 4*b*(*iii*), and FIG. 4*c*(*i*), FIG. 4*c*(*ii*), and FIG. 4*c*(*iii*). The dual TGF-beta1 and TGF-beta2 reactive oligonucleotides ASPH01, ASPH02, ASPH03, ASPH04, ASPH05, ASPH06, ASPH07, and ASPH08, respectively, show again a significant reduction of the expression of both TGF-beta1 and TGF-beta2 mRNA, while the selective TGF-beta2 oligonucleotides significantly inhibit TGF-beta2 mRNA expression.

Example 3

In further experiments the inhibitory effect of each of ASPH01, ASPH03, ASPH05, ASPH17, ASPH18, ASPH22, ASPH26, ASPH27, ASPH33, ASPH36, ASPH37, ASPH41, ASPH42, ASPH45, ASPH46, ASPH47, ASPH48, ASPH49, ASPH64, ASPH65, ASPH66, ASPH69, ASPH71, ASPH80, ASPH82, ASPH88, ASPH89, ASPH90, ASPH98, ASPH99, ASPH102, ASPH105, ASPH115, ASPH121, ASPH140, ASPH153, ASPH165, ASPH171, ASPH178, ASPH181, ASPH184, ASPH185, ASPH186, ASPH187, ASPH188, ASPH189, and of the controls of SEQ ID NO.144 and SEQ ID NO. 145 was tested in human A172 glioma cells. A172 cells were transfected with these modified oligonucleotides in doses of 20 nM, 4 nM, 0.8 nM, 0.16 nM, and 0.04 nM, respectively, in the presence of a transfecting agent. The remaining TGF-beta2 mRNA was measured 24 h after transfection. TGF-beta2 values were normalized to GAPDH and oligonucleotide concentrations resulting in 50% reduction of TGF-beta2 mRNA (=$IC_{50}$ values) were calculated. All $IC_{50}$ values were referenced to the $IC_{50}$ value of ASPH_036 (ASPH36) that was 0.33 nM and the results are shown as fold-difference of the $IC_{50}$ value of ASPH_036 Table 2:

| Oligonucleotide | Fold $IC_{50}$ referenced to ASPH_036 |
|---|---|
| ASPH_080 | 0.591 |
| ASPH_069 | 0.673 |
| ASPH_065 | 0.773 |
| ASPH_105 | 0.882 |
| ASPH_036 | 1.000 |
| ASPH_046 | 1.142 |
| ASPH_098 | 1.182 |
| ASPH_071 | 1.237 |
| ASPH_026 | 1.242 |
| ASPH_047 | 1.303 |
| ASPH_088 | 1.455 |
| ASPH_185 | 1.456 |
| ASPH_115 | 1.545 |
| ASPH_153 | 1.665 |
| ASPH_181 | 1.918 |
| ASPH_027 | 2.000 |
| ASPH_089 | 2.091 |
| ASPH_102 | 2.091 |
| ASPH_041 | 2.182 |
| ASPH_018 | 2.212 |
| ASPH_049 | 2.455 |
| ASPH_022 | 2.485 |
| ASPH_188 | 2.639 |
| ASPH_189 | 2.660 |
| ASPH_042 | 2.848 |
| ASPH_178 | 3.147 |
| ASPH_048 | 3.182 |
| ASPH_066 | 3.182 |
| ASPH_033 | 3.182 |
| ASPH_045 | 3.636 |
| ASPH_121 | 3.644 |
| ASPH_171 | 3.871 |
| ASPH_005 | 3.954 |
| ASPH_003 | 4.111 |
| ASPH_082 | 4.818 |
| ASPH_037 | 5.303 |
| ASPH_099 | 5.545 |
| ASPH_090 | 6.727 |
| ASPH_165 | 7.175 |
| ASPH_186 | 7.655 |
| ASPH_017 | 8.455 |
| ASPH_001 | 9.242 |
| ASPH_187 | 9.990 |
| ASPH_064 | 10.091 |
| ASPH_140 | 11.482 |
| ASPH_184 | 12.224 |
| SEQ ID NO 144 | 17.212 |
| SEQ ID NO 145 | n.a |

All the modified oligonucleotides show an $IC_{50}$ in a low nanomolar to picomolar range, which is markedly lower than $IC_{50}$ of the positive control oligonucleotide of SEQ ID NO. 144; the $IC_{50}$ of the negative control of SEQ ID NO. 145 was not calculable.

Example 4

Figure 5A:
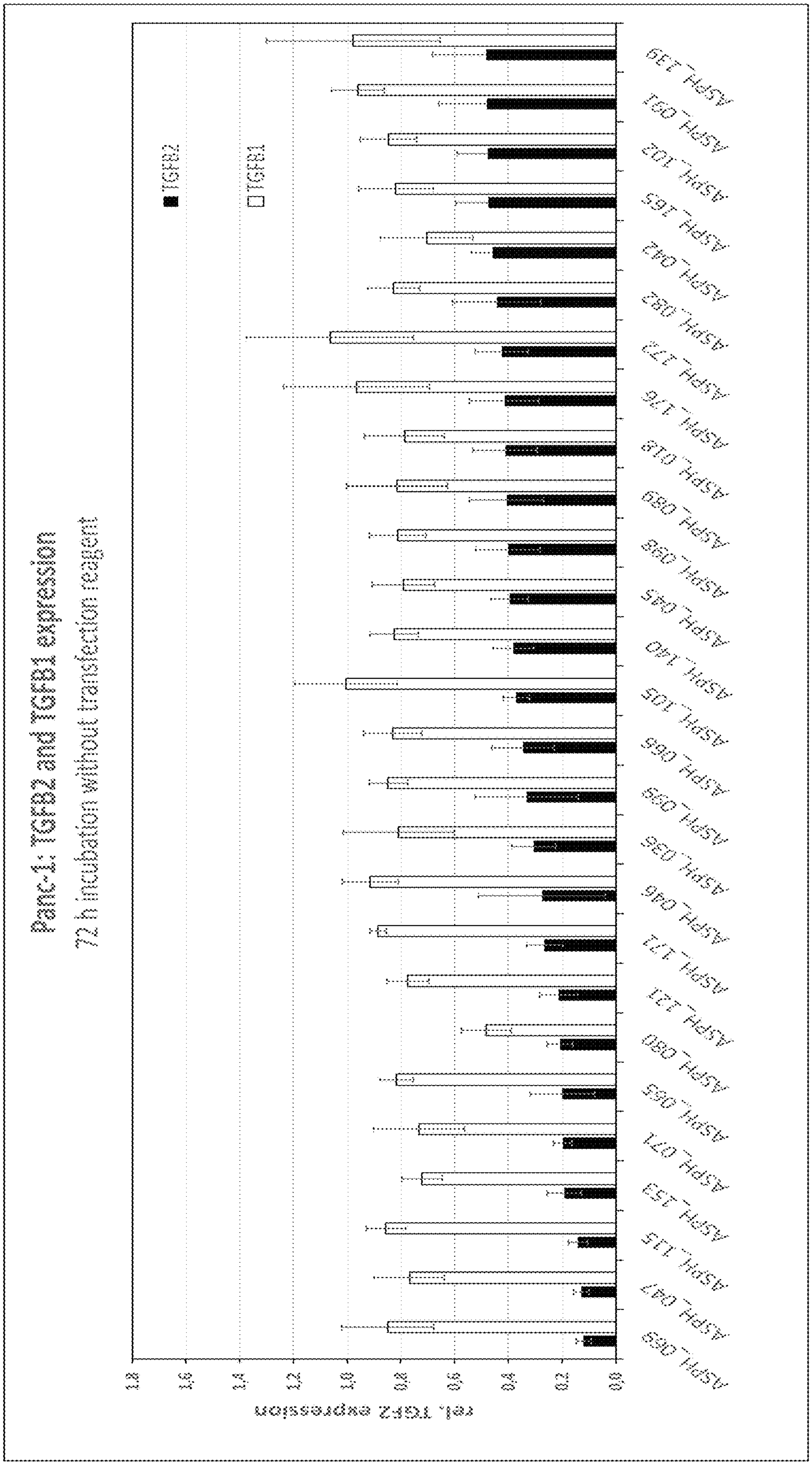
FIG. 5a and FIG. 5b show the inhibition of the expression of TGF-beta1 and TGF-beta2 mRNA in Panc-1 cells. Panc-1 cells were treated with different modified oligonucleotides in a dose of 3.3 μM in the absence of any transfection reagent (gymnotic transfection or unassisted transfection or gymnotic delivery), and the inhibition of the TGF-beta1 (white columns) and TGF-beta2 (black columns) mRNA expression was measured after 72 h.
Figure 5B:
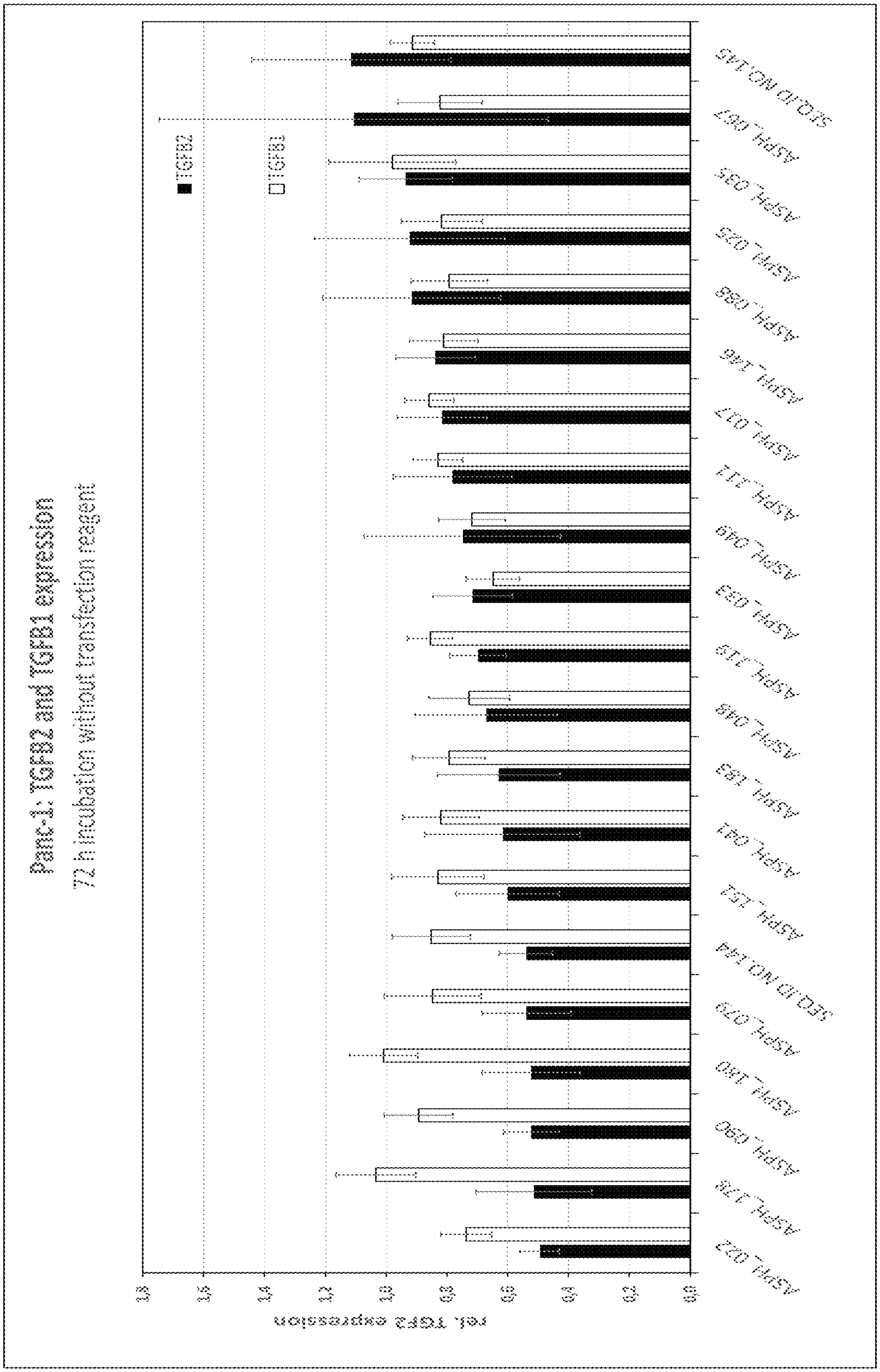

Human Panc-1 pancreatic cancer cells were treated with 3.3 μM of ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183, respectively, or the controls of SEQ ID NO. 144 and 145 in the absence of a transfecting agent (gymnotic transfection or gymnotic delivery). The inhibitory effect of the modified oligonucleotides on expression of TGF-beta1 and TGF-beta2 mRNA, respectively, was determined 72 h after treatment start. Under gymnotic delivery experimental conditions, the oligonucleotides enter the cells and strongly inhibit the expression of TGF-beta2 mRNA. The results of the experiments are shown in FIG. 5*a* and FIG. 5*b*.

Example 5

Figure 6A:
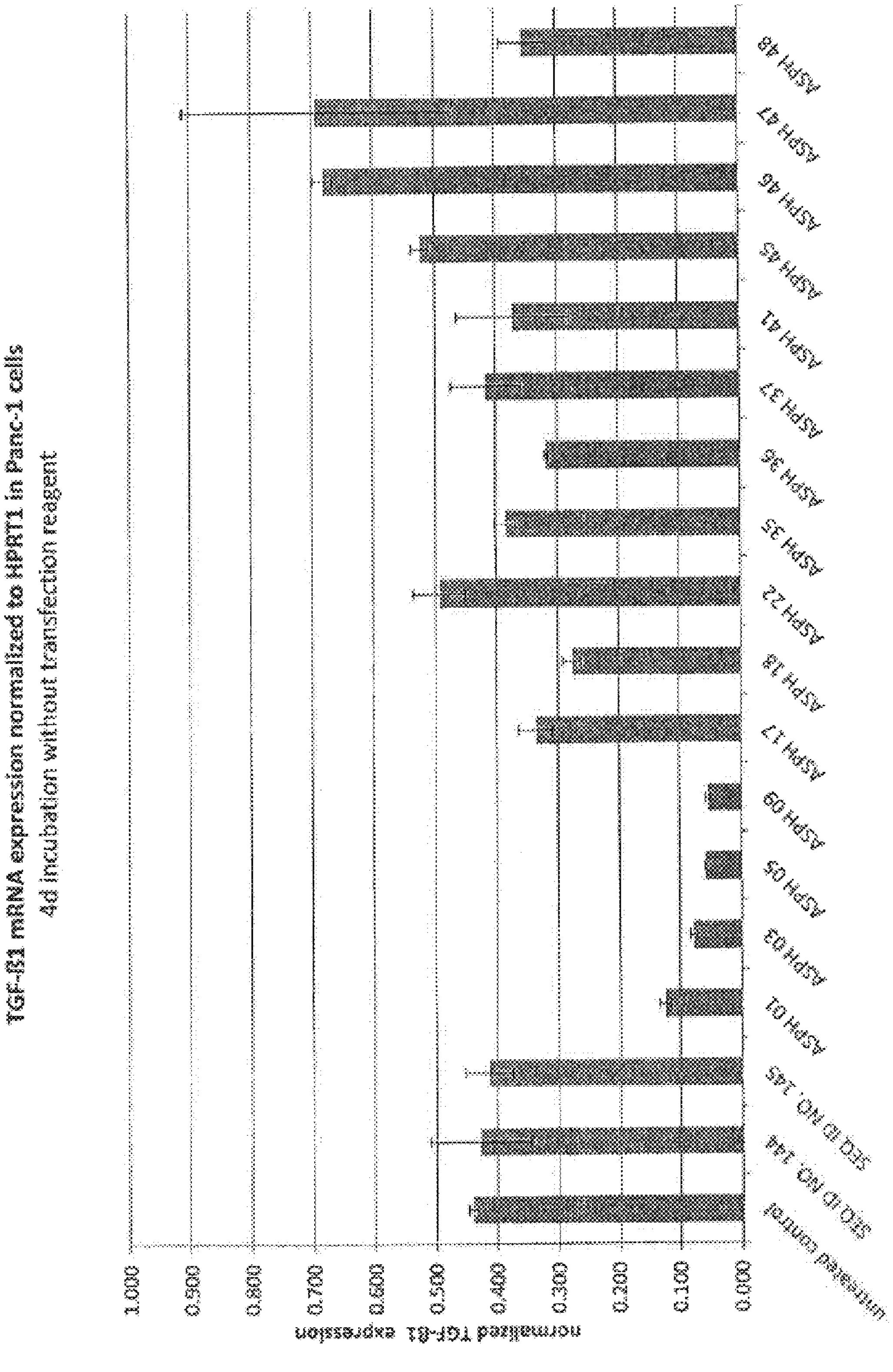
FIG. 6a presents the inhibition of the expression of TGF-beta1 mRNA and FIG. 6b presents the inhibition of the expression of TGF-beta2 mRNA.
Figure 6B:
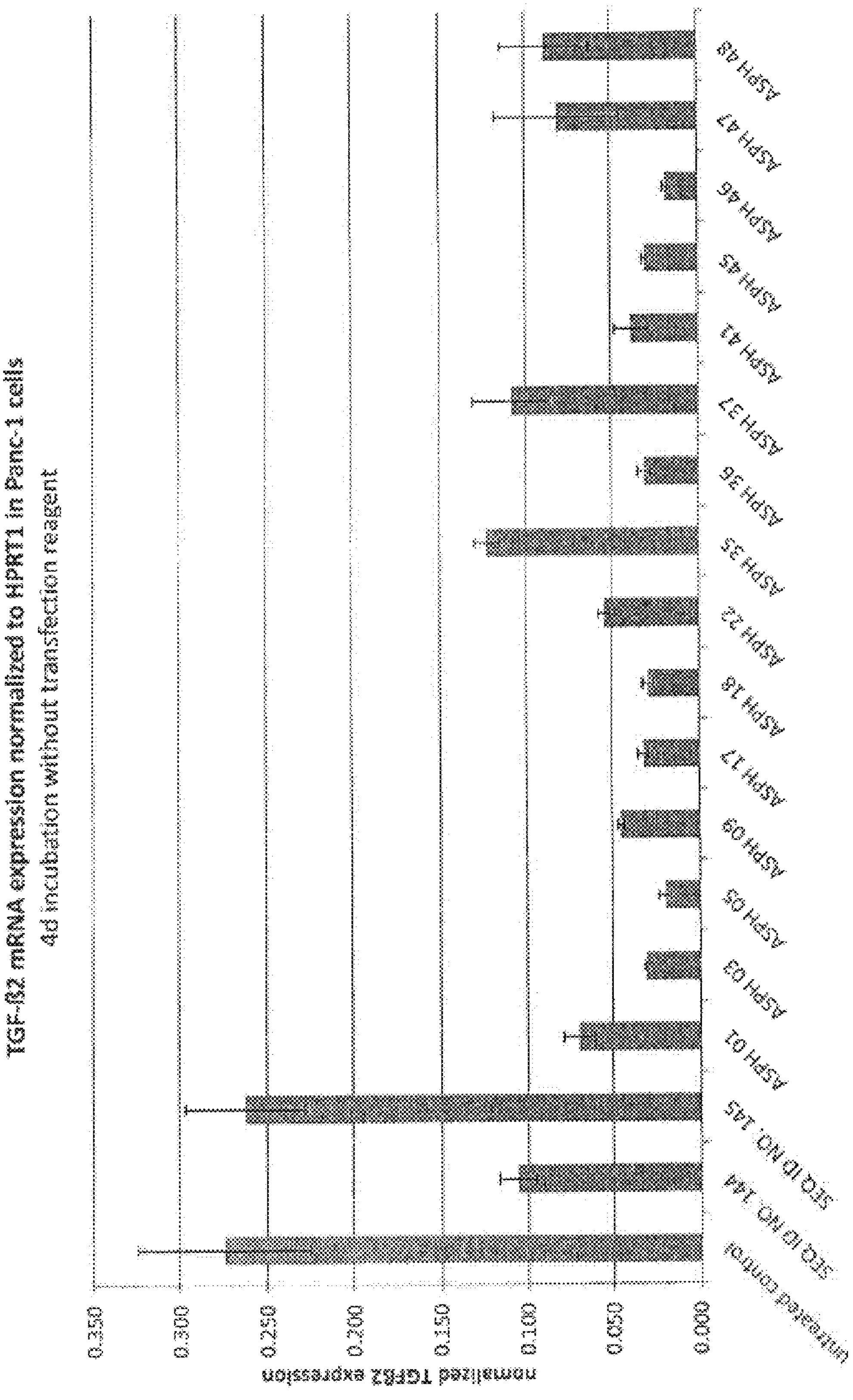
Figure 7A:
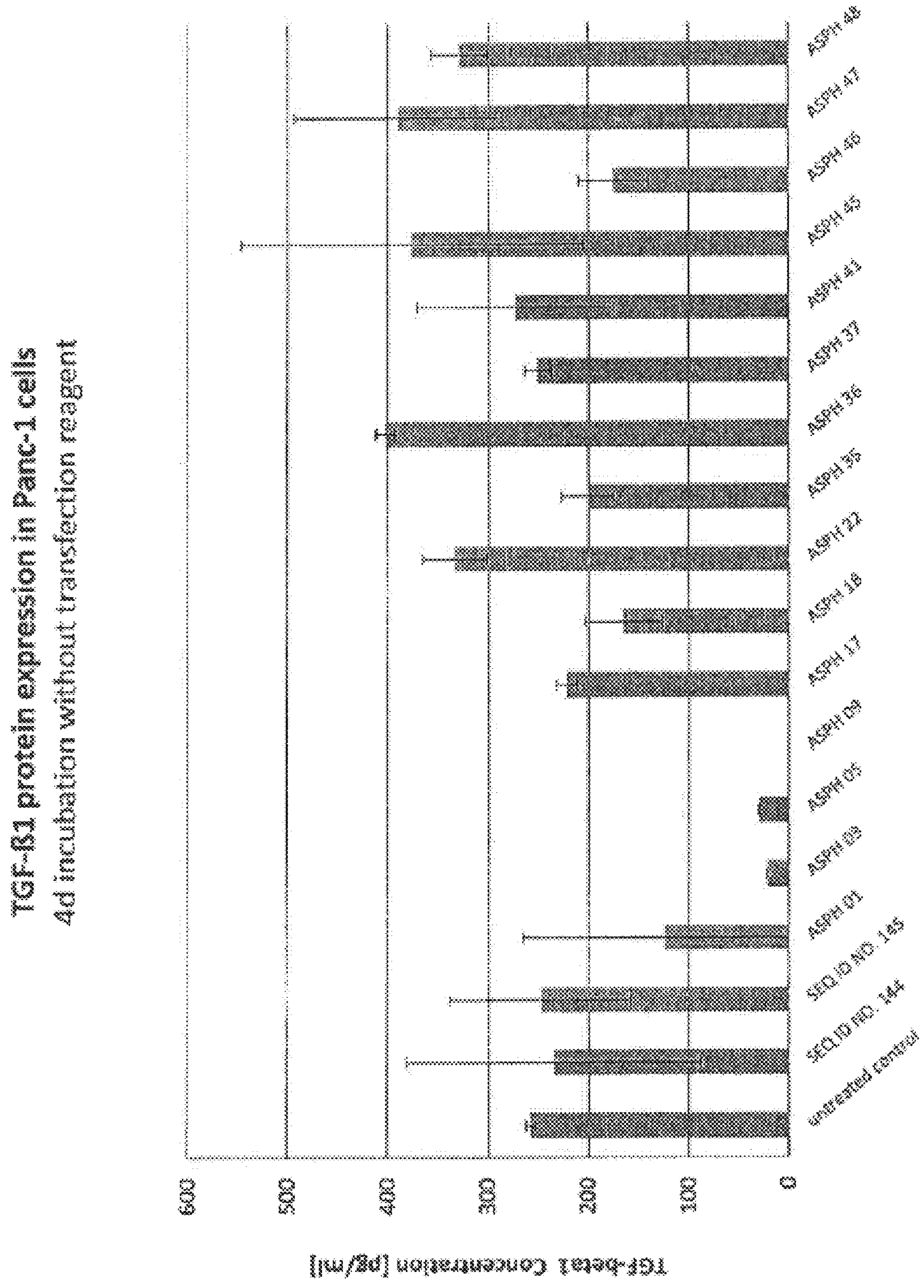
FIG. 7a presents the inhibition of TGF-beta1 protein in Panc-1 cells and FIG. 7b presents the inhibition of TGF-beta2 protein in Panc-1 cells. Panc-1 cells were treated with different modified oligonucleotides in a dose of 10 μM via gymnotic delivery, i.e., in the absence of any transfecting reagent, and the inhibition of the TGF-beta1 and TGF-beta2 mRNA expression and protein was measured 4 days after transfection.
Figure 7B:
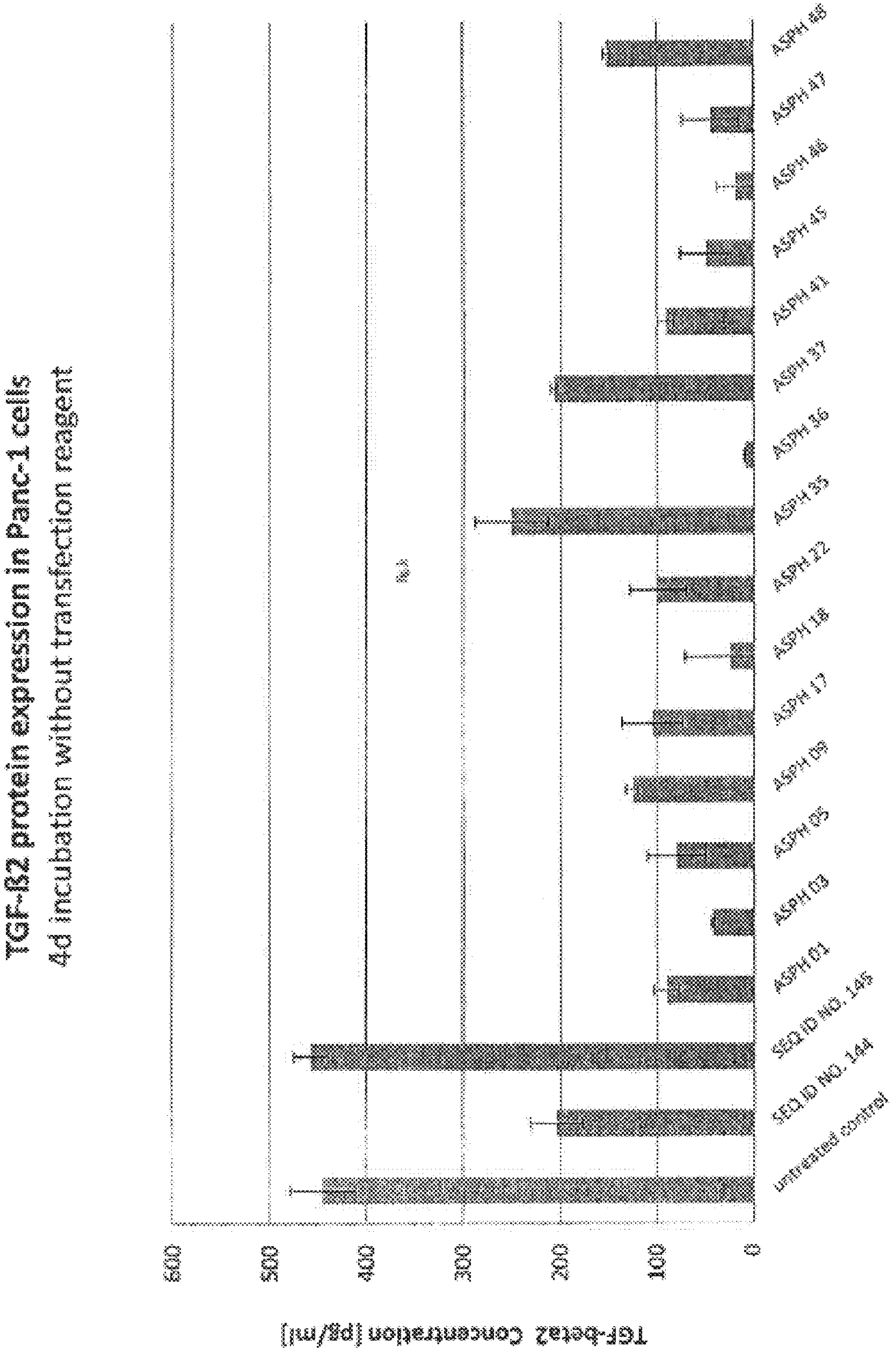

In further experiments human Panc-1 pancreatic cancer cells were transfected with 10 μM of modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48, respectively, or the controls of SEQ ID NO. 144 and 145 in the absence of a transfecting agent (gymnotic transfection or gymnotic delivery). The oligonucleotides were added to the cells for 2 days, after which medium was changed, and further incubation for 2 days was carried out in oligonucleotide-containing medium. Expression of TGF-beta1 mRNA (FIG. 6*a*) and TGF-beta2 mRNA (FIG. 6*b*) was then measured and normalized to HPRT1 (Hypoxanthin-Phosphoribosyl-Transferase1). Cell supernatants were analysed for TGF-beta1 (FIG. 7*a*) and TGF-beta2 (FIG. 7*b*) protein by ELISA. Under gymnotic delivery experimental conditions, dual TGF-beta1 and TGF-beta2 reactive oligonucleotide ASPH01, ASPH03, ASPH05, and pan-specific ASPH09 significantly inhibit the expression of TGF-beta1 and TGF-beta2 mRNA, and protein. All the other oligonucleotides significantly inhibit the expression of TGF-beta2 mRNA and protein.

Example 6

Figure 8A:
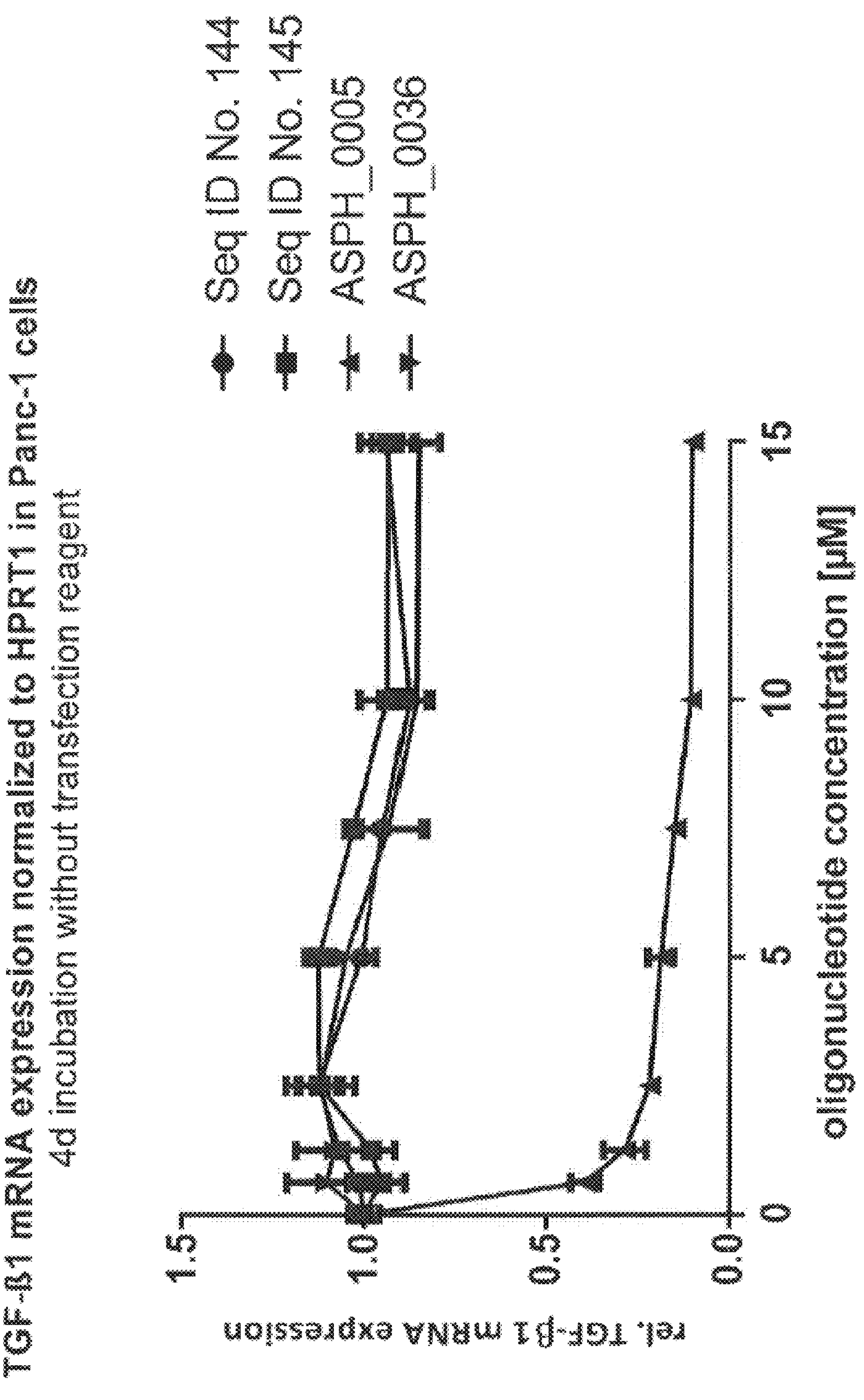
FIG. 8a and FIG. 8b depicts the dose-dependent effect of modified oligonucleotides ASPH05 and ASPH36 on TGF-beta1 and TGF-beta2 mRNA expression. Panc-1 cells were treated for 4 days with 15 μM, 10 μM, 7.5 μM, 5 μM, 2.5 μM, 1.25 μM, or 0.625 μM of either ASPH05 (dual TGF-beta1 and TGF-beta2 oligonucleotide) or ASPH36 (selective TGF-beta2 oligonucleotide) modified oligonucleotide in the absence of a transfection reagent. Remaining TGF-beta1 (FIG. 8a) or TGF-beta2 mRNA (FIG. 8b) was measured after 4 days. Experiments are described in Example 6.
Figure 8B:
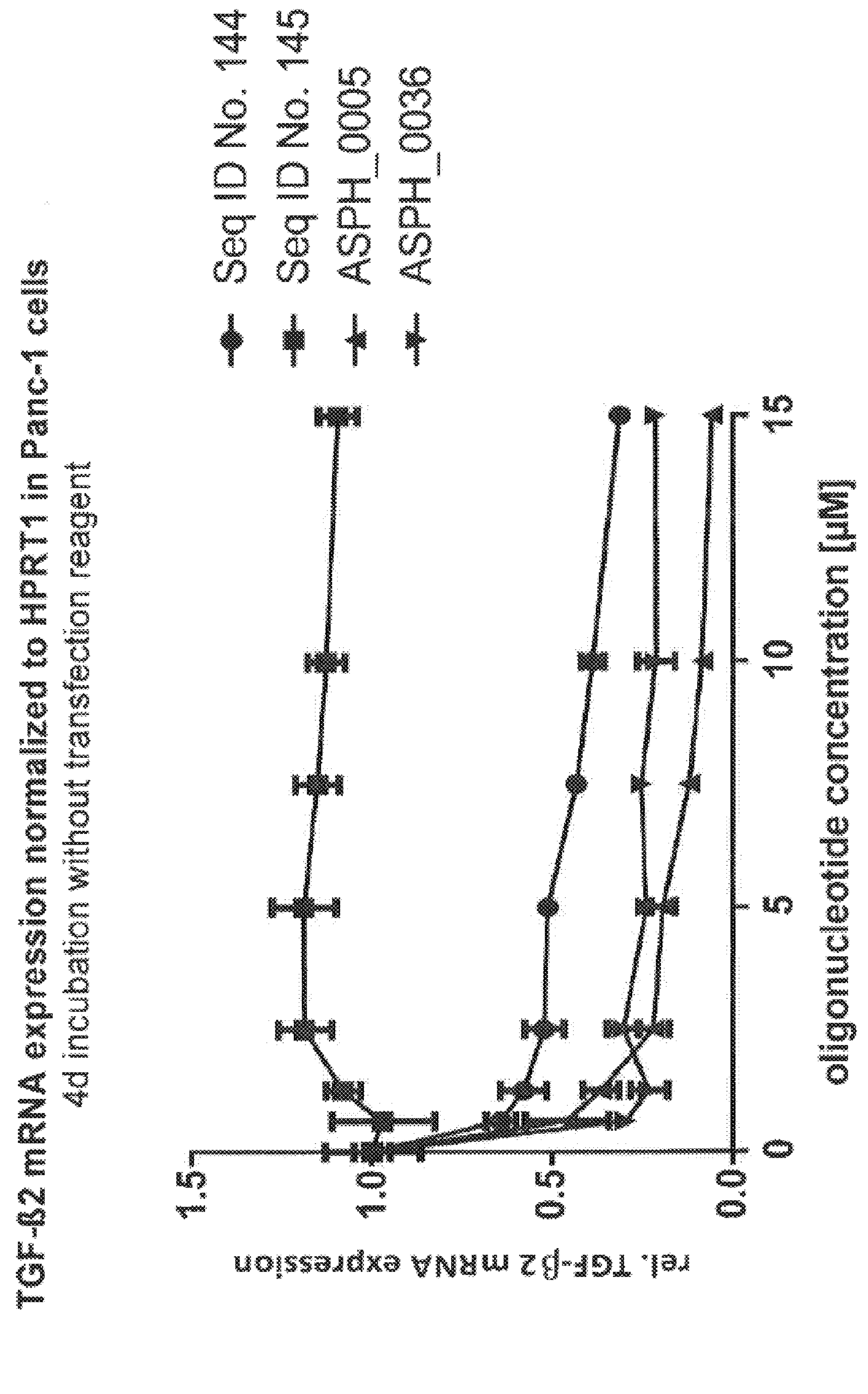

In another experiment dose dependency of the inhibitory effect of modified oligonucleotides of the present invention was tested. Human Panc-1 pancreatic cancer cells were treated with 15 μM, 10 μM, 7.5 μM, 5 μM, 2.5 μM, 1.25 μM, or 0.625 μM ASPH05 or ASPH36, or the controls of SEQ ID NO. 144 and 145, respectively, without using a transfection reagent. The oligonucleotides were added to the cells for 2 days. Thereafter media were changed and cells were incubated for 2 further days in oligonucleotide-containing medium, after which (total treatment time: 4 days) the expression of TGF-beta1 (FIG. 8*a*) and TGF-beta2 (FIG. 8*b*) mRNA was measured. The dual TGF-beta1 and TGF-beta2 reactive oligonucleotide ASPH05 shows a marked dose dependent inhibition of both TGF-beta1 and TGF-beta2 mRNA expression, and ASPH36 inhibits specifically the expression of TGF-beta2 mRNA in a dose-dependent manner.

Example 7

Figure 9:
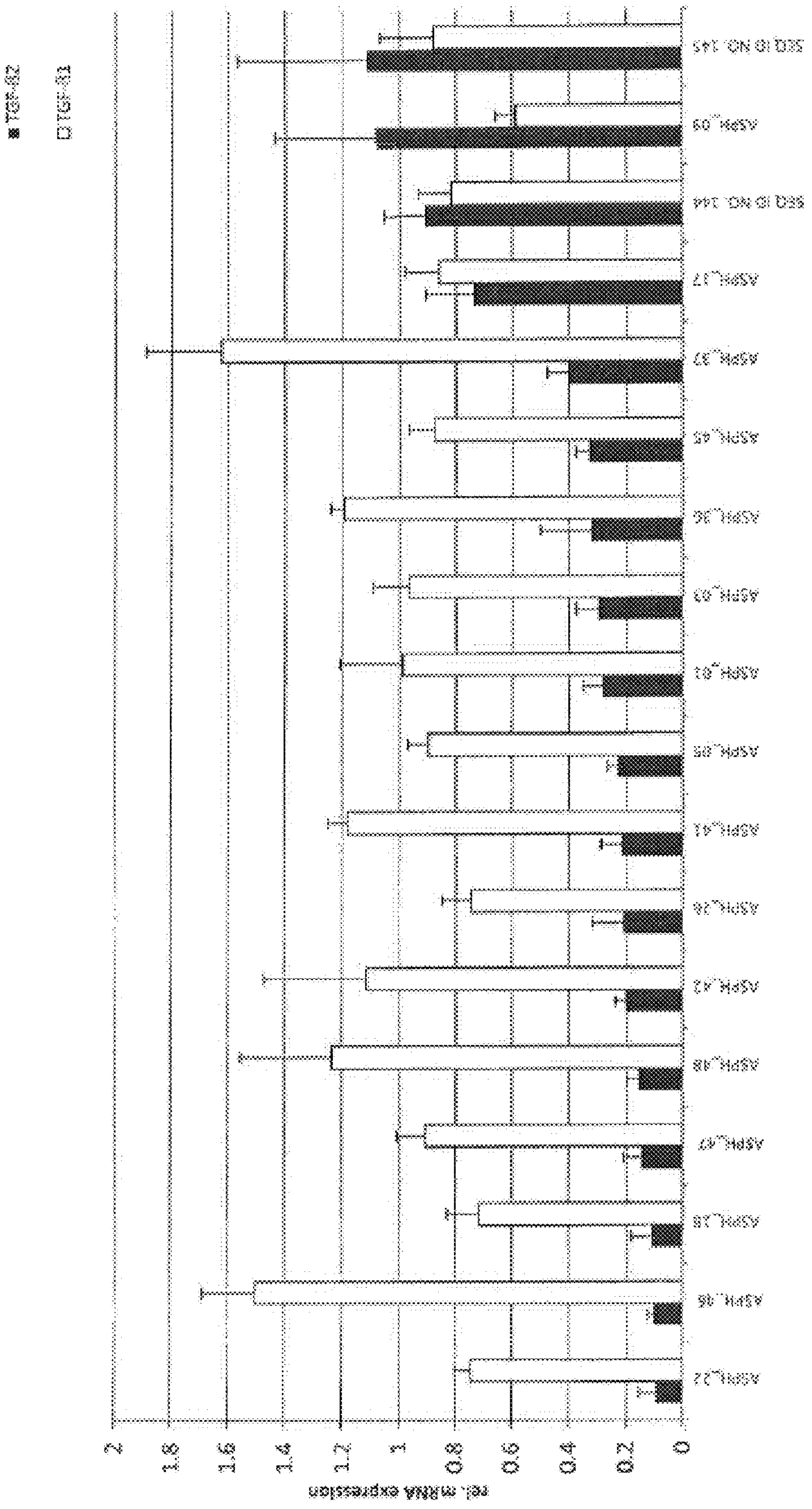
FIG. 9 shows the inhibition of the expression of TGF-beta1 and TGF-beta2 mRNA in mouse SMA-560 glioma cells. SMA-560 cells were transfected with ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48 in a dose of 10 nM (in the presence of a transfecting agent). Inhibition of the mouse TGF-beta1 (white columns) and TGF-beta2 (black columns) mRNA expression was determined 24 h after transfection. Experiments are described in Example 7.

Mouse SMA-560 glioma cells were transfected with 10 nM ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48, or the controls of SEQ ID NO. 144 and 145, respectively, in the presence of a transfecting agent. 24 h after transfection, the inhibition of the expression of TGF-beta1 (white columns) and TGF-beta2 (black columns) mRNA was determined. The pan-specific ASPH09 inhibits the expression of the mouse TGF-beta1 mRNA, and the other oligonucleotides tested strongly inhibit the expression of the mouse TGF-beta2 mRNA. The results are presented in FIG. 9.

Example 8

Figure 10:
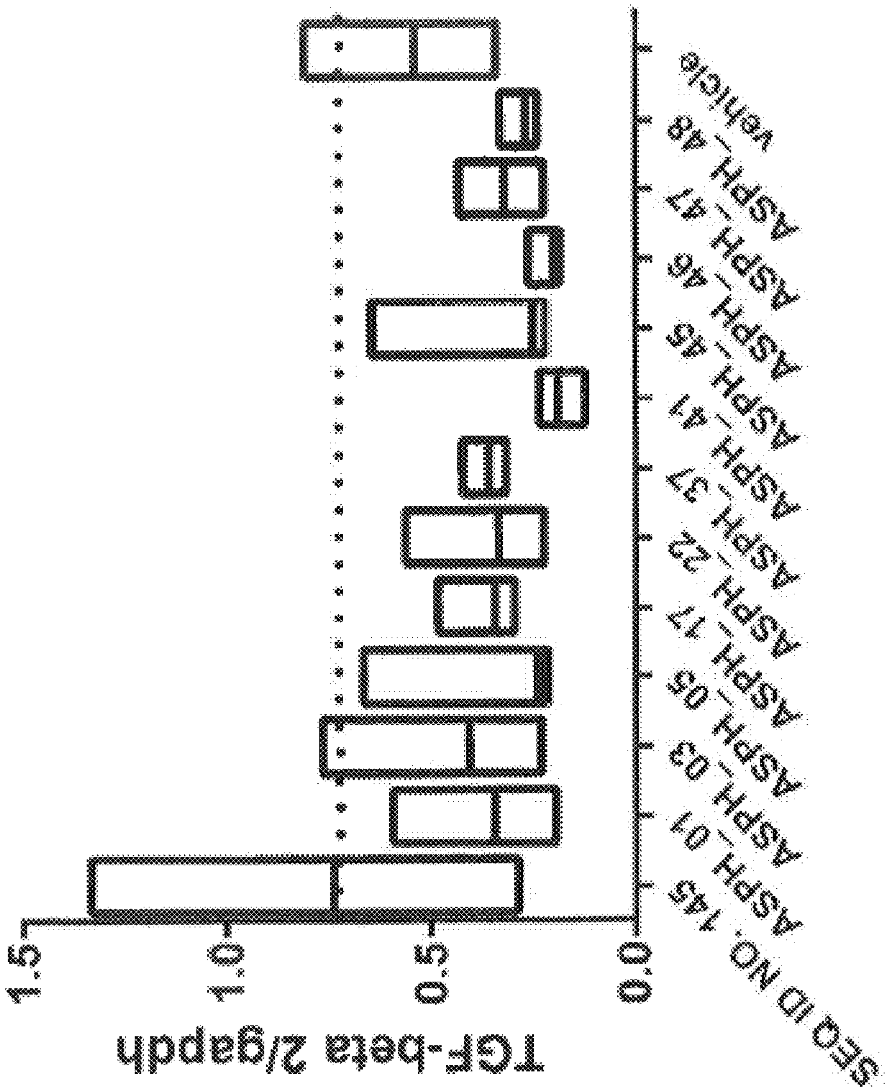
FIG. 10 presents in vivo data referring to the treatment of female athymic nude mice with ASPH01, ASPH03, ASPH05, ASPH17, ASPH22, ASPH37, ASPH41, ASPH45, ASPH46, ASPH47, or ASPH48 at 14 mg/kg body weight by subcutaneous injection for 5 consecutive days. 24 h after the last treatment, mice were sacrificed and mouse TGF-beta 2 mRNA was quantified in kidney tissue lysates. Data—representing TGF-beta2 to GAPDH mRNA ratio—are shown as a box plot in which median values and min. and max. values are presented (data expressed as n=4, except ASPH46 group n=3). Experiments are described in Example 8.

Female athymic nude mice (Hsd: Athymic Nude-Foxn1$^{nu}$) were treated for 5 consecutive days with 14 mg/kg or 50 mg/kg of oligonucleotide ASPH01, ASPH03, ASPH05, ASPH17, ASPH22, ASPH37, ASPH41, ASPH45, ASPH46, ASPH47, or ASPH48, and control of SEQ ID NO. 145, respectively, or saline by subcutaneous injection. The day after the last treatment, the mice were sacrificed. Mouse TGF-beta2 mRNA was quantified in kidney tissue lysates. In FIG. 10, data—representing TGF-beta2 to GAPDH mRNA ratio—are shown as a box plot in which median values and min. and max. values are presented (data expressed as n=4, except ASPH46 group n=3). All the tested oligonucleotides inhibited the expression of TGF-beta2 mRNA in the kidney of these mice.

Example 9

Figure 11:
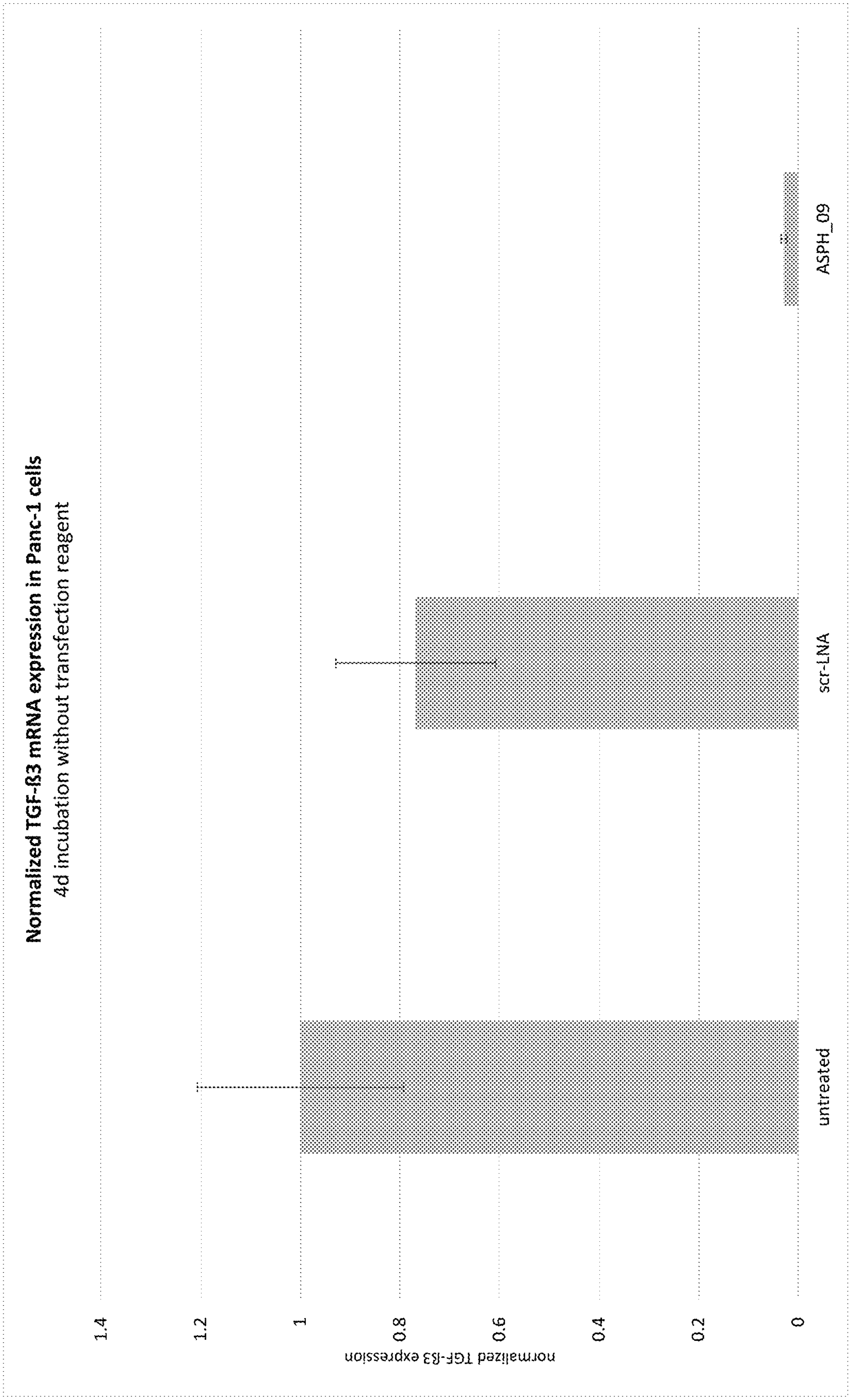
FIG. 11 shows the inhibition of the expression of TGF-beta3 mRNA in Panc-1 cells. Panc-1 cells were treated with ASPH09 in a dose of 10 μM in the absence of any transfection reagent (gymnotic transfection or unassisted transfection), and inhibition of the TGF-beta3 mRNA expression was measured after 4 days. ASPH09 is a pan-specific oligonucleotide inhibiting the expression of TGF-beta3 as well as TGF-beta1 and TGF-beta2 (FIG. 6a and FIG. 6b). Experiment is described in Example 9.

In another experiment human Panc-1 pancreatic cancer cells were transfected with 10 μM of modified oligonucleotide ASPH09 or the control of SEQ ID NO. 145 in the absence of any transfecting agent (gymnotic transfection or gymnotic delivery). The oligonucleotides were added to the cells for 2 days, after medium was changed, and further incubation for 2 days was carried out in oligonucleotide-containing medium. Expression of TGF-beta3 mRNA (see FIG. 11) was then measured and normalized to HPRT 1 (Hypoxanthin-Phosphoribosyl-Transferase1). Under gymnotic delivery experimental conditions, the pan-specific oligonucleotide ASPH09 significantly inhibits the expression of TGF-beta3 mRNA.

Example 10

Human Panc-1 pancreatic cancer cells were treated with 10 μM, 3.3 μM, 1.1 μM, 0.37 μM, and 0.12 μM of ASPH03, ASPH36, ASPH45, ASPH47, ASPH65, ASPH69, AASPH71, ASPH80, ASPH115, ASPH 121, ASPH153, ASPH185, and ASPH189, respectively, in the absence of a transfecting agent (gymnotic transfection or gymnotic delivery). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic delivery experimental conditions, the oligonucleotides enter the cells and strongly inhibit the expression of TGF-beta2 mRNA. The results of the experiments are shown in Table 3:

| Name | IC50 (μM) |
|---|---|
| ASPH_065 | 0.37 |
| ASPH_071 | 0.371 |
| ASPH_115 | 0.6 |
| ASPH_069 | 0.655 |
| ASPH_047 | 0.78 |
| ASPH_080 | 0.81 |
| ASPH_153 | 0.9 |
| ASPH_045 | 1.21 |
| ASPH_121 | 1.27 |

-continued

| Name | IC50 (μM) |
|---|---|
| ASPH_036 | 1.5 |
| ASPH_185 | 3.05 |
| ASPH_003 | 3.62 |
| ASPH_189 | 4.26 |

All the modified oligonucleotides show an $IC_{50}$ in the low micromolar or even submicromolar range, showing that they have very high potency even without the requirement of a transfection reagent.

Example 11

Human Panc-1 pancreatic cancer cells were treated with 10 μM, 3.3 μM, 1.1 μM, 0.37 μM, and 0.12 μM of ASPH47, ASPH190, ASPH191, ASPH192, and ASPH193, respectively, in the absence of a transfecting agent (gymnotic transfection or gymntic delivery). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic delivery experimental conditions, the oligonucleotides enter the cells and strongly inhibit the expression of TGF-beta2 mRNA. The results of the experiments are shown in Table 4:

| Name | IC50 (μM) |
|---|---|
| ASPH_047 | 0.76 |
| ASPH_190 | 0.18 |
| ASPH_191 | 0.97 |
| ASPH_192 | 0.145 |
| ASPH_193 | 0.144 |

All the modified oligonucleotides show an $IC_{50}$ in the submicromolar to lower submicromolar range, showing that they have extremely high potency even without the requirement of a transfection reagent.

Example 12

Figure 13A:
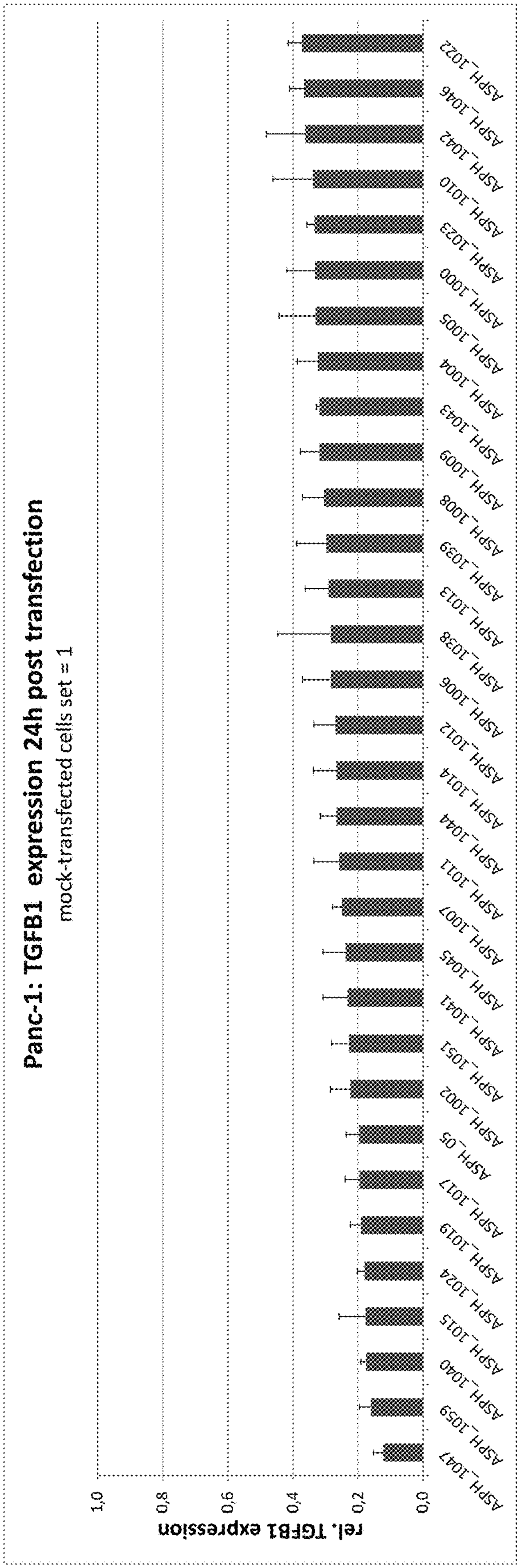
FIG. 13a and FIG. 13b depicts the inhibition of the expression of TGF-beta1 mRNA in human Panc-1 pancreatic cancer cells. Panc-1 cells were transfected with different modified oligonucleotides in a dose of 10 nM (in the presence of a transfecting agent), and inhibition of the TGF-beta1 mRNA expression was measured 24 h after transfection.
Figure 13B:
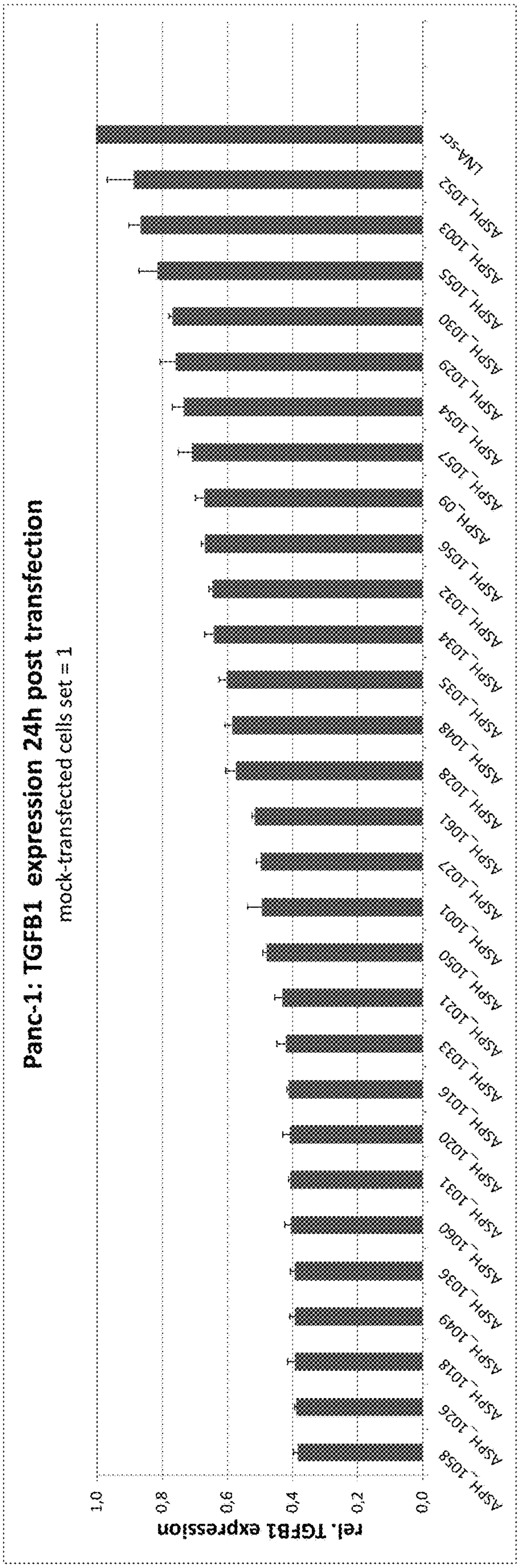

Human Panc-1 pancreatic cancer cells were transfected with 10 nM of ASPH05, ASPH09, ASPH1000, ASPH1001, ASPH1002, ASPH1003, ASPH1004, ASPH1005, ASPH1006, ASPH 1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH 1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, or ASPH1061 and the control of SEQ ID NO. 145, respectively, in the presence of a transfecting agent. The expression of TGF-beta1 mRNA was determined 24 h after transfection. Significant reduction of the expression of TGF-beta1 in Panc-1 cells is shown in FIG. 13*a* and FIG. 13*b*.

Example 13

Figure 14:
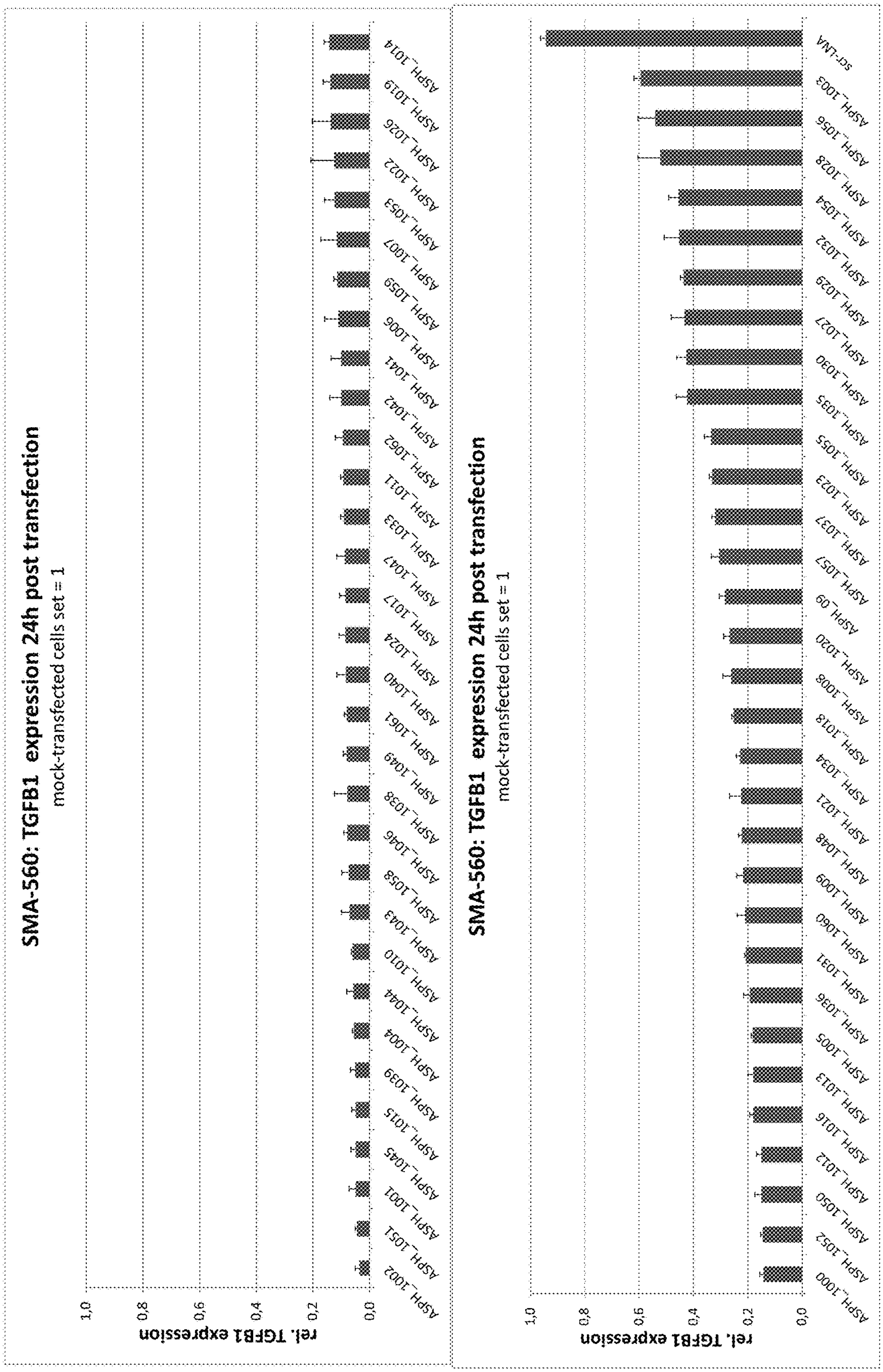
FIG. 14 shows the inhibition of the expression of TGF-beta1 mRNA in mouse SMA-560 glioma cells. Cells were transfected with different modified oligonucleotides in a dose of 10 nM (in the presence of a transfecting agent), and inhibition of the TGF-beta1 mRNA expression was measured 24 h after transfection.

Mouse SMA-560 glioma cells were transfected with 10 nM of ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH 1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062 and the control of SEQ ID NO. 145, respectively, in the presence of a transfecting agent. The expression of TGF-beta1 mRNA was determined 24 h after transfection. Significant reduction of the expression of TGF-beta1 in SMA-560 cells is shown in FIG. 14.

Example 14

Figure 15A:
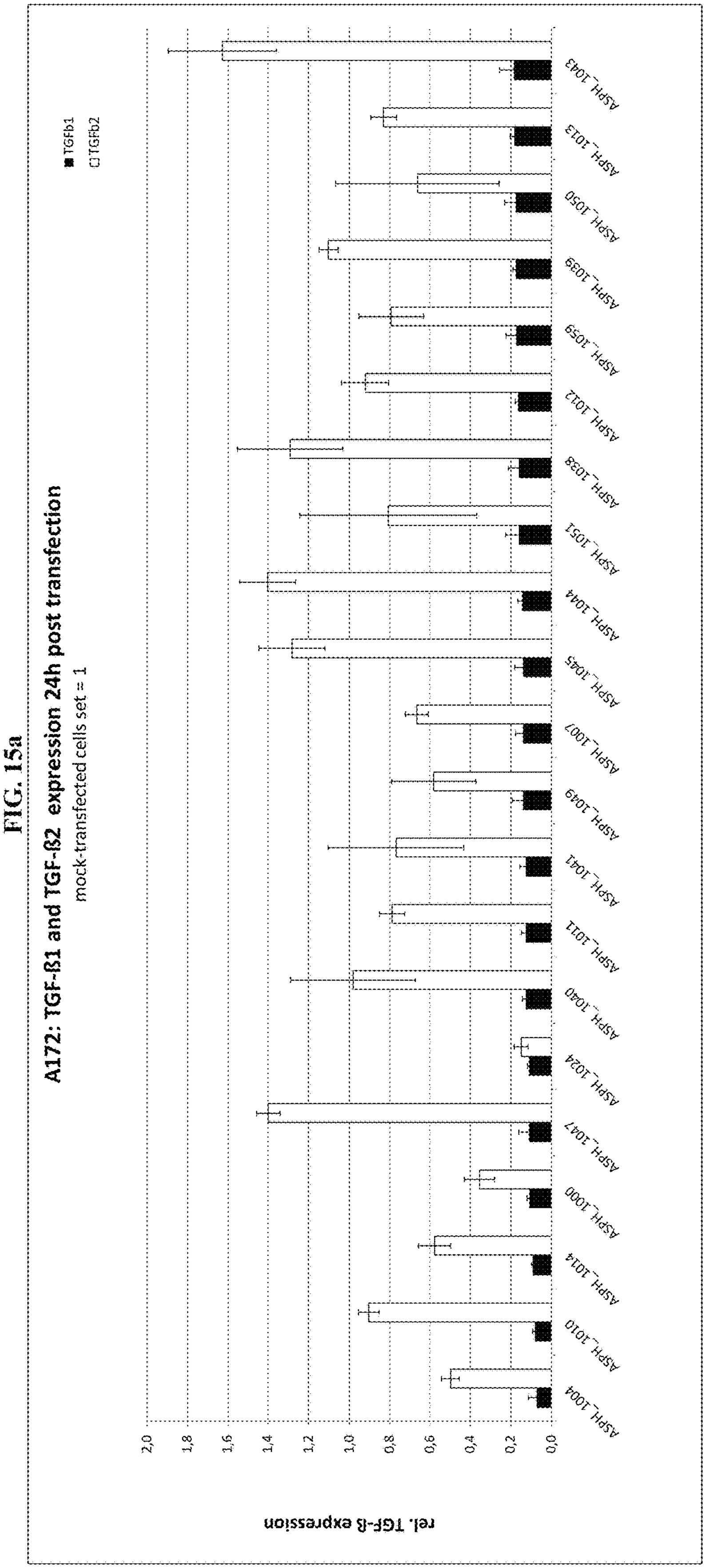
FIG. 15*a*, FIG. 15*b*, and FIG. 15*c* depict the inhibition of the expression of TGF-beta1 and TGF-beta2 mRNA in human A172 cells. Cells were transfected with different modified oligonucleotides in a dose of 10 nM (in the presence of a transfecting agent), and inhibition of the TGF-beta1 and TGF-beta2 mRNA expression was measured 24 h after transfection.
Figure 15B:
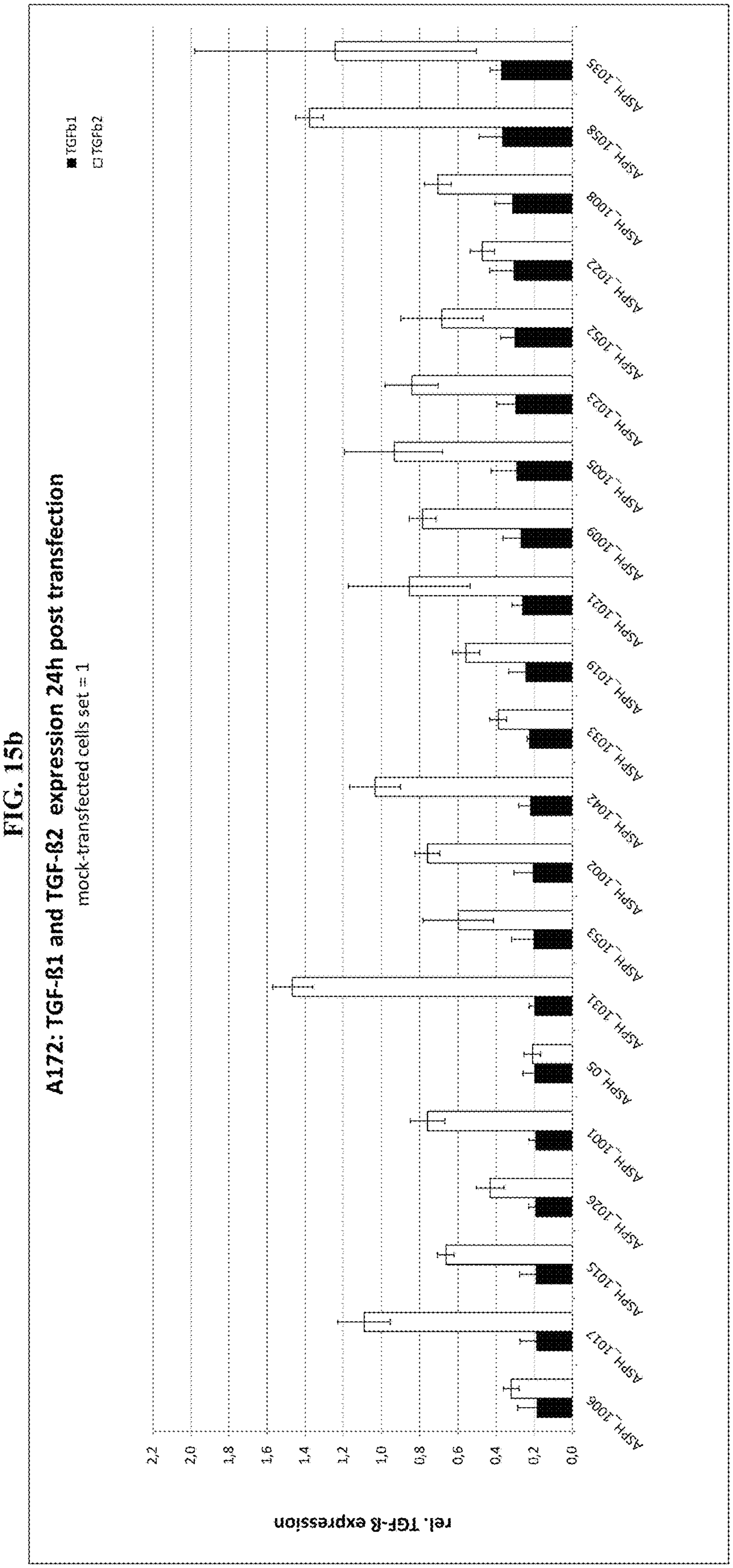
Figure 15C:
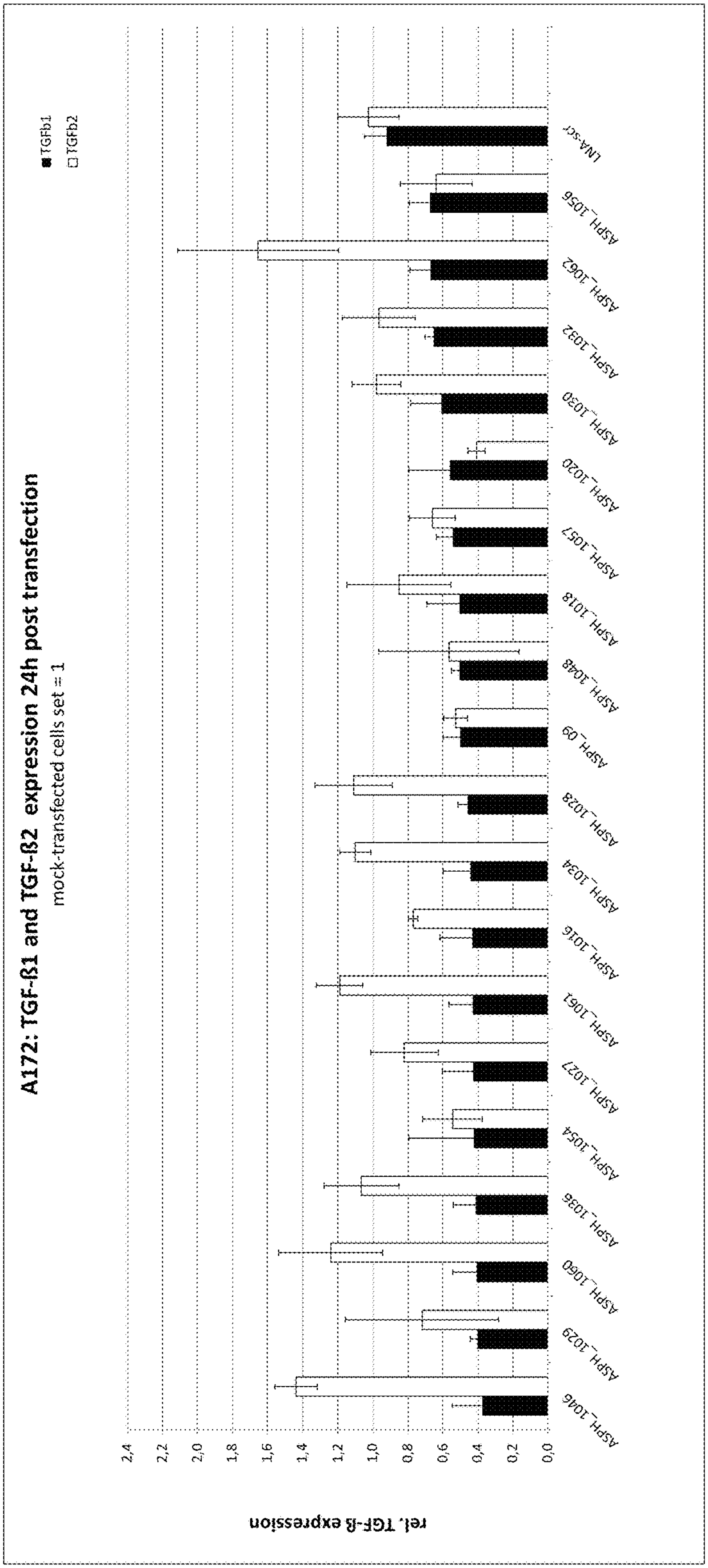

In these experiments, human A172 glioma cells were transfected with 10 nM of ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, or ASPH1062, and the control of SEQ ID NO. 145, respectively, in the presence of a transfecting agent. The expression of TGF-beta1 and TGF-beta2 mRNA was determined 24 h after transfection. Significant reduction of the expression of TGF-beta1 mRNA is shown in FIG. 15*a*, FIG. 15*b*, and FIG. 15*c*. The dual TGF-beta1 and TGF-beta2 reactive oligonucleotides ASPH05 shows a significant reduction of the expression of both TGF-beta1 and TGF-beta2 mRNAs, while the selective TGF-beta1 oligonucleotides significantly inhibit TGF-beta1 mRNA expression.

Example 15

Figure 16A:
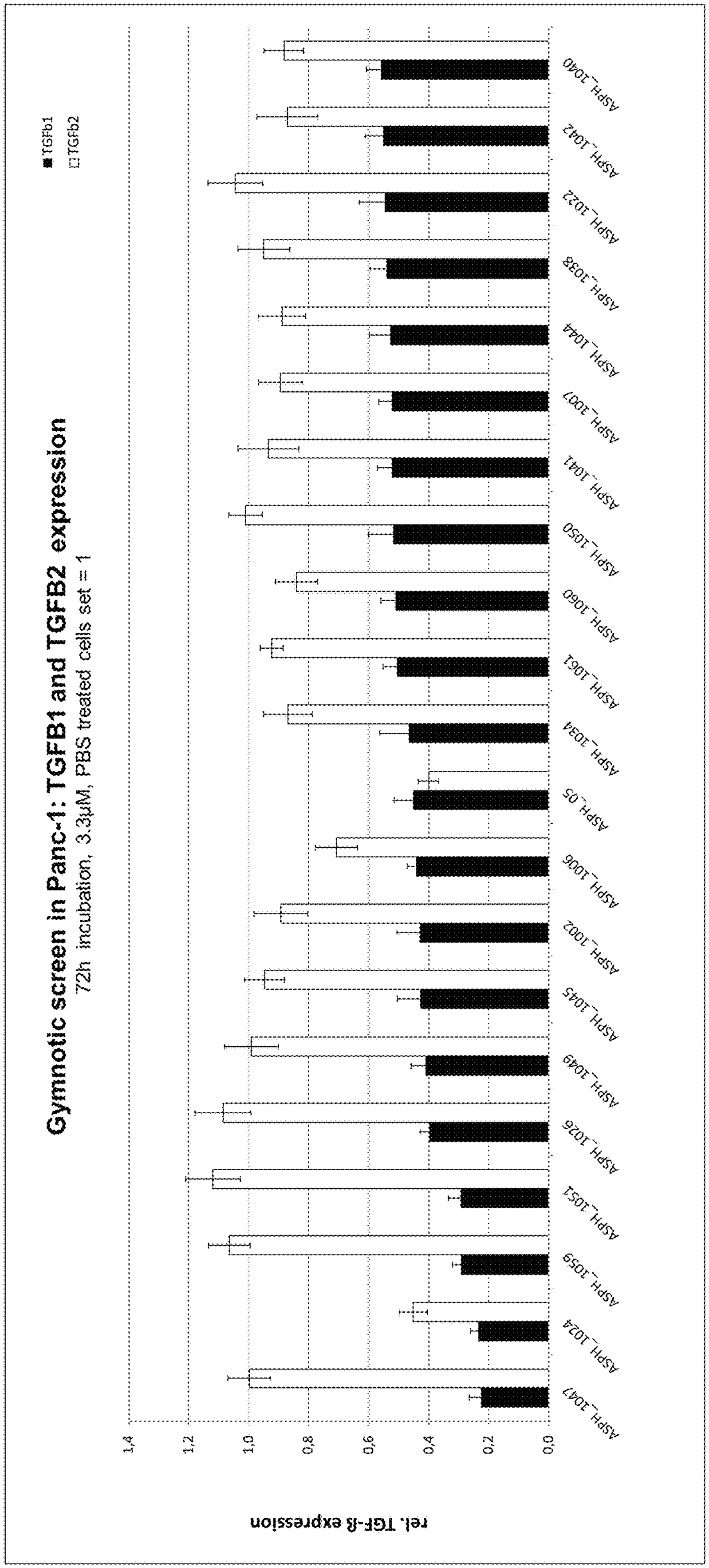
FIG. 16*a*, FIG. 16*b*, and FIG. 16*c* show the inhibition of the expression of TGF-beta1 and TGF-beta2 mRNA in Panc-1 cells. Panc-1 cells were treated with different modified oligonucleotides in a dose of 3.3 μM in the absence of any transfection reagent (gymnotic transfection or unassisted transfection or gymnotic delivery), and inhibition of the TGF-beta1 (black columns) and TGF-beta2 (white columns) mRNA expression was measured after 72 h.
Figure 16B:
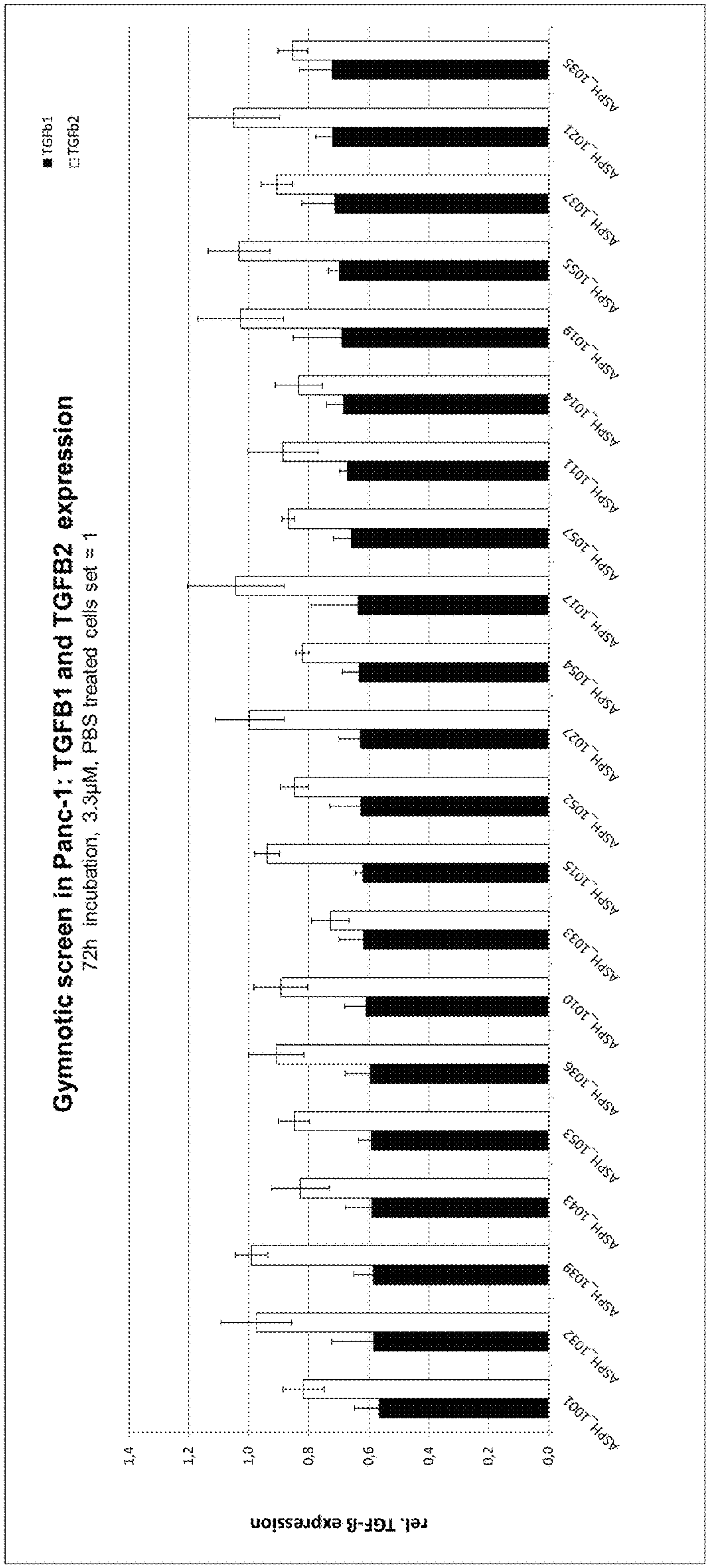
Figure 16C:
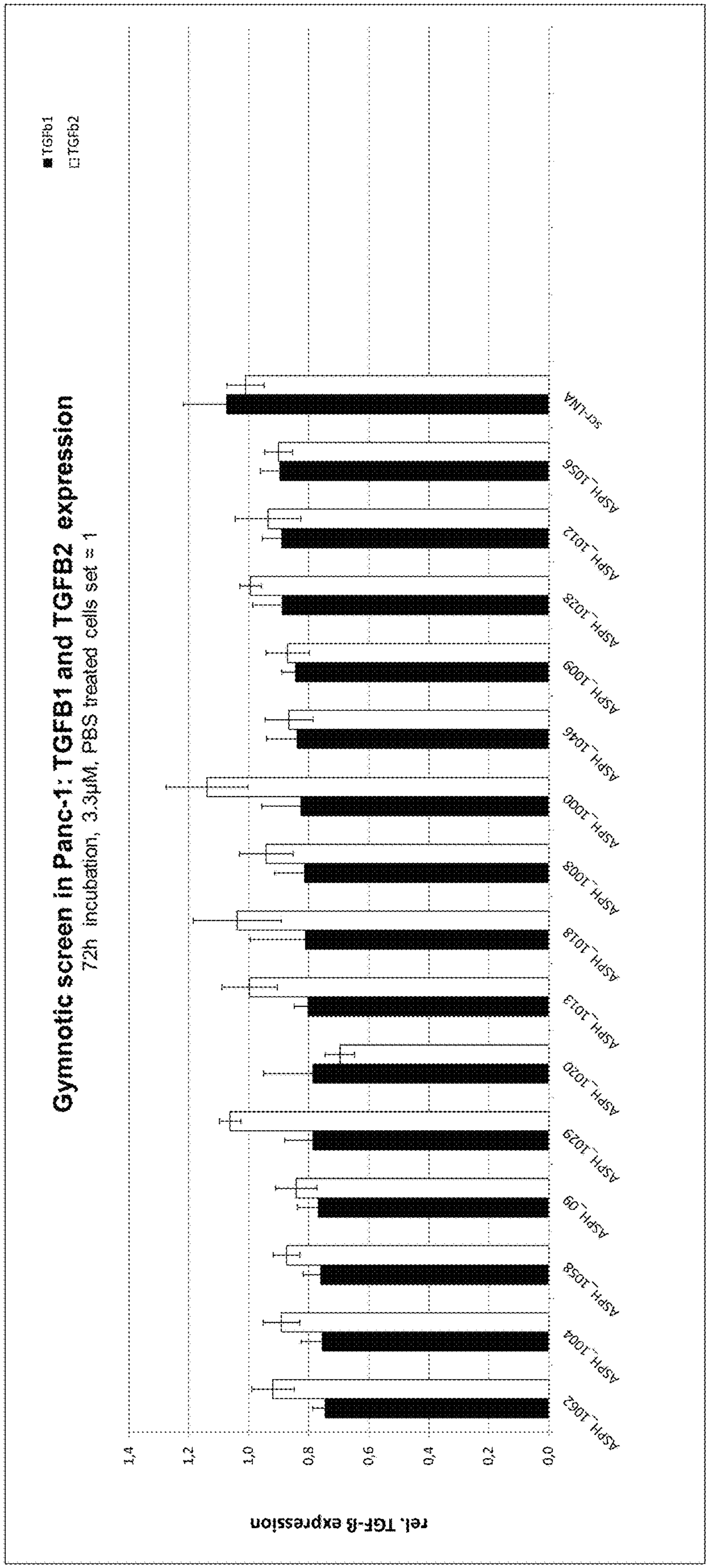

Human Panc-1 pancreatic cancer cells were treated with 3.3 μM of ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062, or the control of SEQ ID NO. 145 in the absence of a transfecting agent (gymnotic transfection or gymnotic delivery). The inhibitory effect of the modified oligonucleotides on expression of TGF-beta1 and TGF-beta2 mRNA, respectively, was determined 72 h after treatment start. Significant reduction of the expression of TGF-beta1 mRNA is shown in FIG. 16*a*, FIG. 16*b*. and FIG. 16*c*. The dual TGF-beta1 and TGF-beta2 reactive oligonucleotides ASPH05 shows a significant reduction of the expression of both TGF-beta1 and TGF-beta2 mRNAs, while the selective TGF-beta1 oligonucleotides significantly inhibit TGF-beta1 mRNA expression.

Example 16

Figure 17:
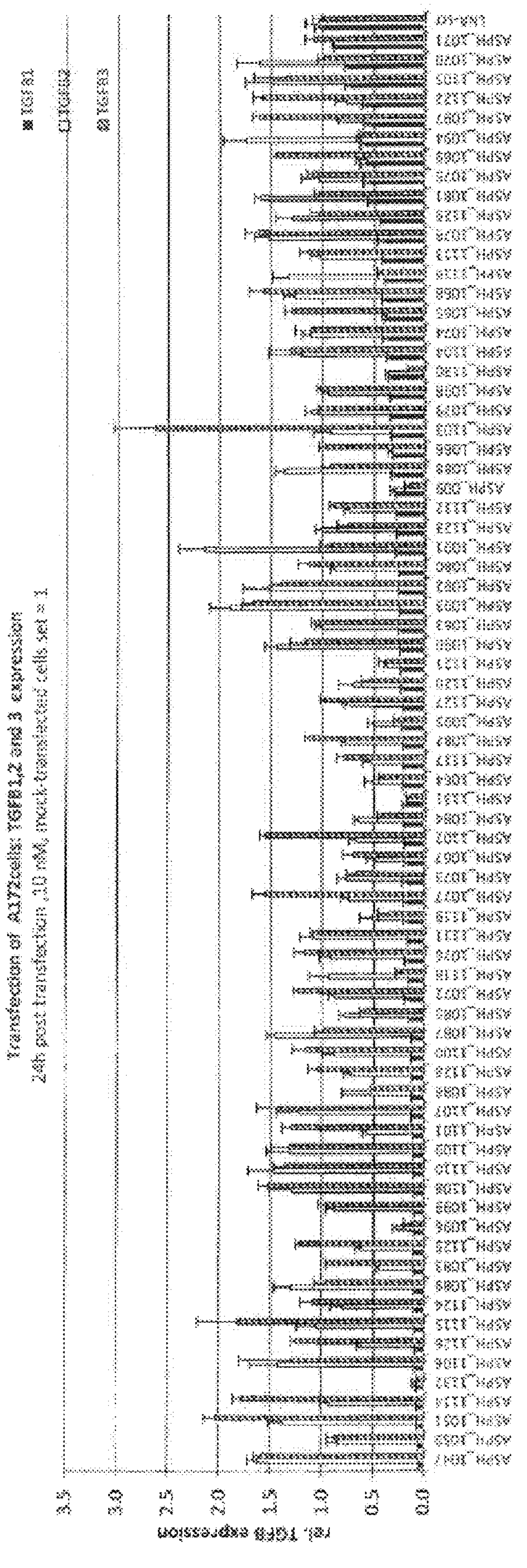
FIG. 17 depicts the inhibition of the expression of TGF-beta1, TGF-beta2 and TGF-beta3 mRNA in human A172 cells. Cells were transfected with different modified oligonucleotides in a dose of 10 nM (in the presence of a transfecting agent), and inhibition of the TGF-beta1 (black column), TGF-beta2 (white column) and TGF-beta3 (striped column) mRNA expression was measured 24 h after transfection.

Human A172 glioma cells were treated with 10 nM (in the presence of a transfecting agent), of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, respectivel, or the positive control ASPH1047. The expression of TGF-beta1 (black column), TGF-beta2 (white column) and TGF-beta3 (striped column) mRNA was determined 24 h after transfection. Significant reduction of the expression of TGF-beta1 mRNA is shown in FIG. 17. The pan-specific TGF-beta1, TGF-beta2 and TGF-beta3 reactive oligonucleotides ASPH0009, ASPH1096, ASPH1131, and ASPH1132 show a significant reduction of the expression of all three isoforms, while the selective TGF-beta1 oligonucleotides significantly inhibit TGF-beta1 mRNA expression.

Example 17

Figure 18A:
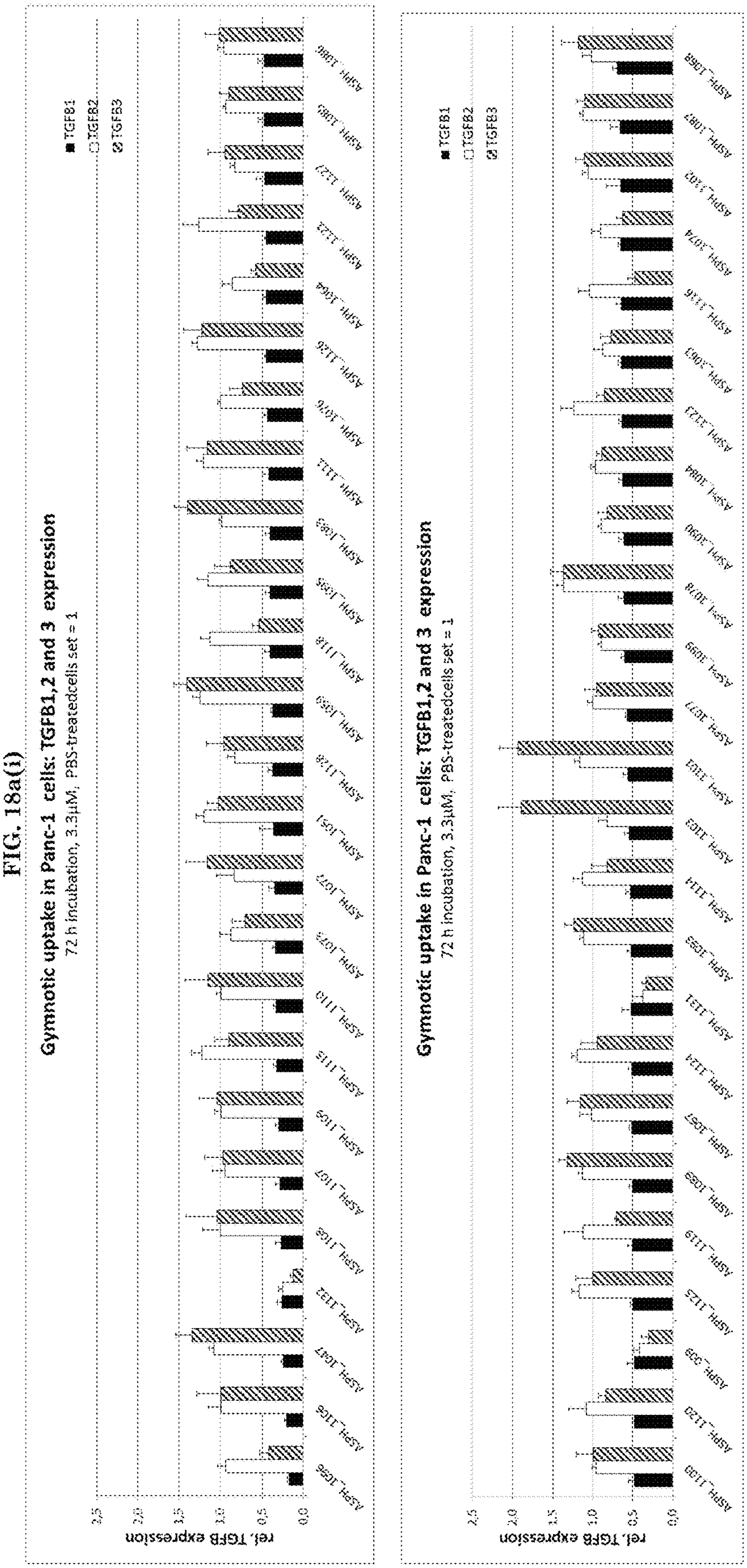
FIG. 18*a*(*i*), and FIG. 18*a*(*ii*) show the inhibition of the expression of TGF-beta1, TGF-beta2 and TGF-beta3 mRNA in human Panc-1 and RenCa cells. Cells were transfected with different modified oligonucleotides in a dose dose of 3.3 μM in the absence of any transfection reagent (gymnotic transfection or unassisted transfection or gymnotic delivery), and inhibition of the TGF-beta1 (black column), TGF-beta2 (white column) and TGF-beta3 (striped column) mRNA expression was measured 72 h after transfection.
Figure 18B:
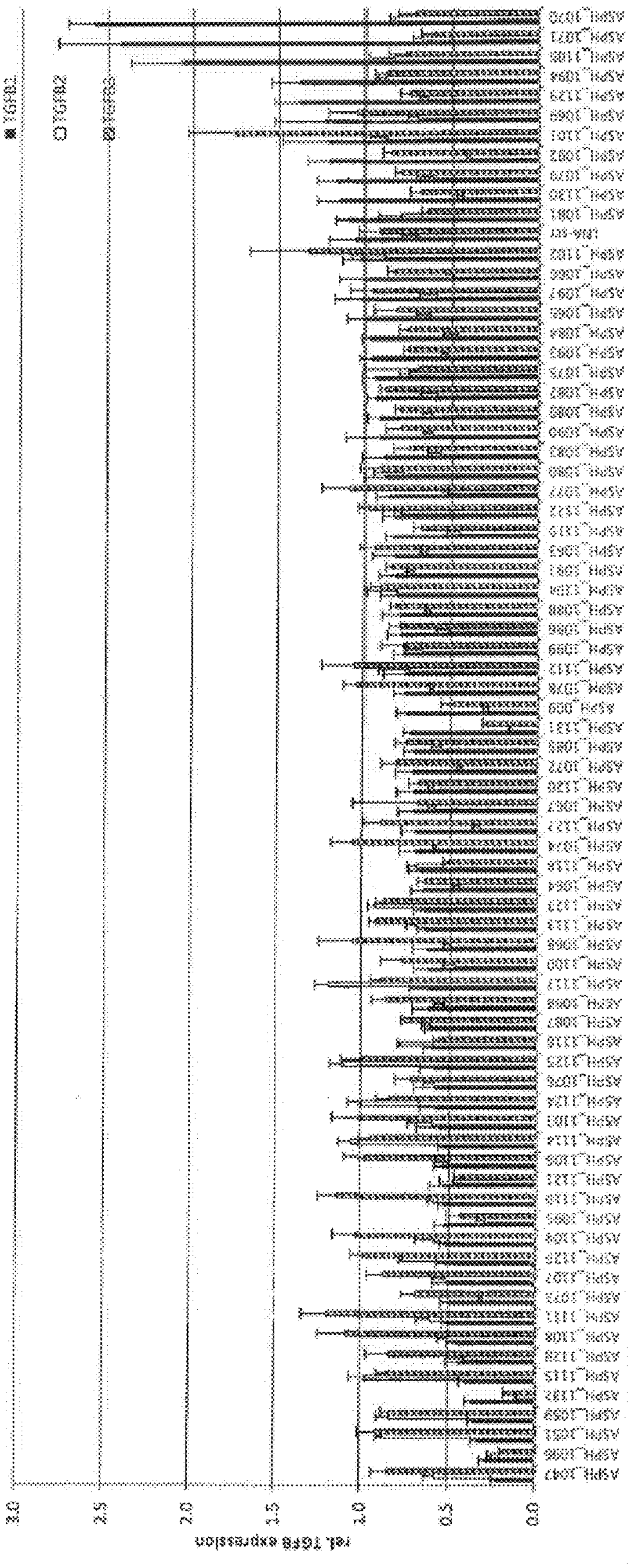
FIG. 18*b* presents the inhibiting effect of these oligonucleotides in RenCa cells.

Either human Panc-1 pancreatic cancer cells (FIG. 18*a*(*i*), and FIG. 18*a*(*ii*) or mouse RenCa renal cell carcinoma cells (FIG. 18*a*(*i*), and FIG. 18*a*(*ii*)) were treated with 3.3 µM of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, respectively, or the positive control ASPH1047 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is shown in FIG. 17. The pan-specific TGF-beta1, TGF-beta2 and TGF-beta3 reactive oligonucleotides ASPH0009, ASPH1096, ASPH1131, and ASPH1132 show significant reduction of the expression of all three isoforms, while the selective TGF-beta1 oligonucleotides significantly inhibit TGF-beta1 mRNA expression.

Example 18

Figure 22:
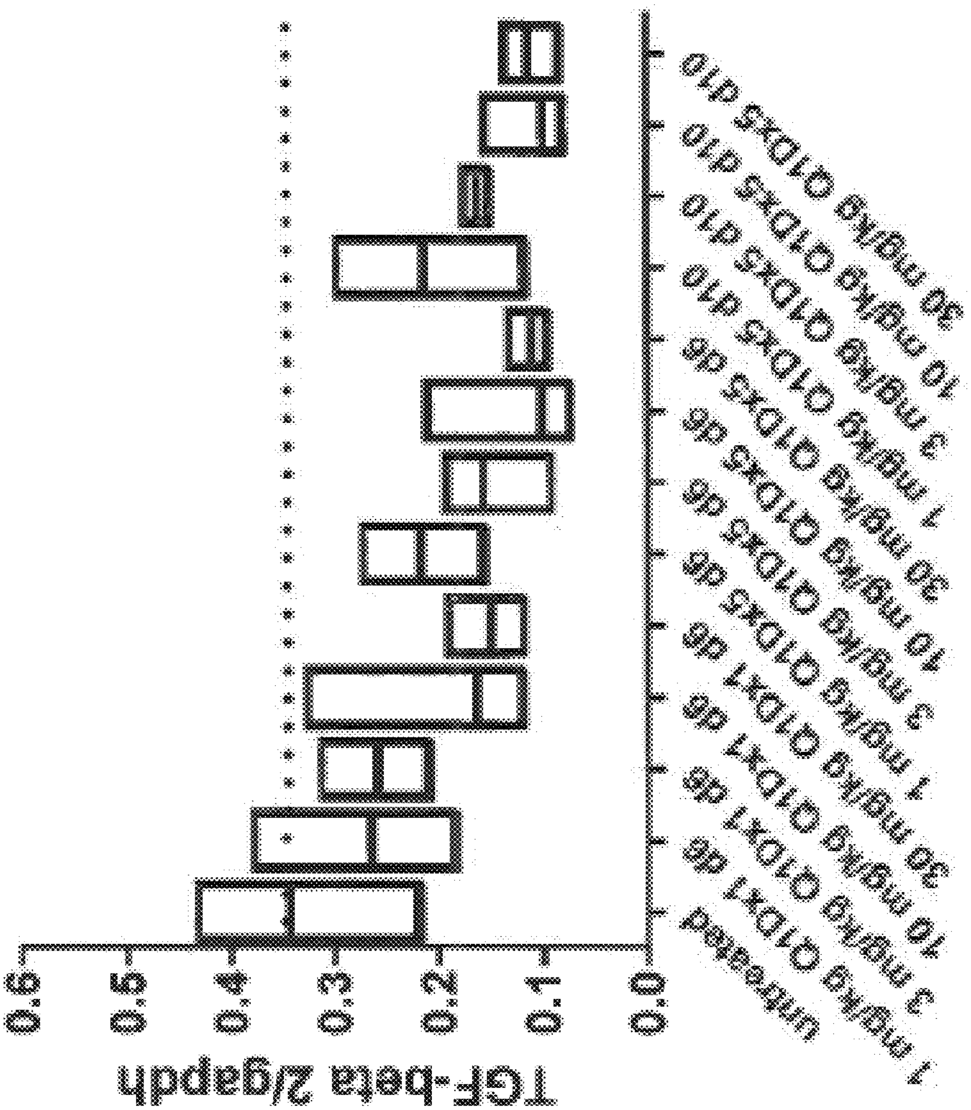
FIG. 22 shows TGF-beta2 mRNA expression in the kidney of mice bearing subcutaneous human pancreatic carcinoma Panc-1. Mice were treated with 1, 3, 10, and 30 mg/kg of ASPH47 after indicated treatment schedules for 5 days: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). TGF-beta2 expression was detected by bDNA assay and normalized to GAPDH. Data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

Mice bearing human Panc-1 pancreatic carcinoma subcutaneous tumors were treated with 1, 3, 10, and 30 mg/kg of ASPH47 under various treatment schedules: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). There was a dose dependent down-regulation of TGF-beta2 mRNA in the kidney of these animals. TGF-beta2 down-regulation was persistent up to 5 days after the last treatment with ASPH47, even after only single administration. TGF-beta2 expression was detected by bDNA assay (branched DNA assay, which is a sandwich nucleic acid hybridization method that uses bDNA molecules to amplify signal from captured target RNA) and normalized to GAPDH. As shown in FIG. 22, data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

Example 19

Figure 23:
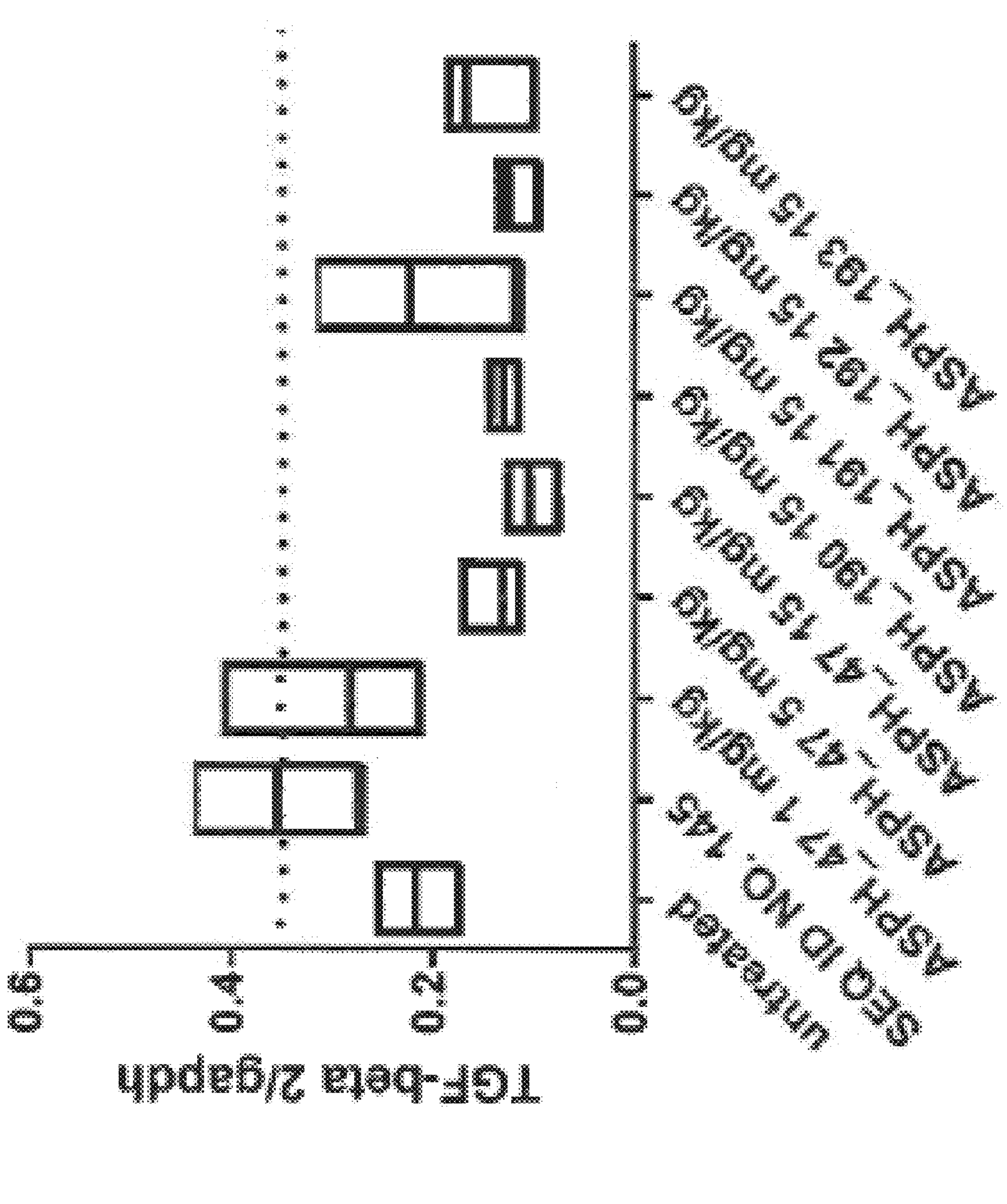
FIG. 23 depicts TGF-beta2 mRNA expression in the kidneys of mice bearing human pancreatic carcinoma Panc-1 tumors. Mice were treated with subcutaneous injections of various oligonucleotides for 5 consecutive days using indicated treatment doses: daily injection of 1, 5, 15 or 50 mg/kg oligonucleotides for five consecutive days. TGF-beta2 mRNA expression was detected by bDNA assay and normalized to GAPDH. Data—representing TGF-beta2 to GAPDH mRNA ratio—are shown as a box plot in which median values and min. and max. values are presented (data expressed as n=5).

Mice bearing human Panc-1 pancreatic carcinoma subcutaneous tumors on both left and right flanks were treated with a daily subcutaneous injection of 1, 5, 15 or 50 mg/kg oligonucleotides for five consecutive days. The tumors were collected 24 hours after the last treatment and snap frozen. TGF-beta mRNA expression in tumors was detected by bDNA assay. Data—representing TGF-beta2 to GAPDH mRNA ratio—are shown as a box plot in which median values and min. and max. values are presented (data expressed as n=5). TGF-beta2 mRNA was down-regulated in tumors treated with various oligonucleotides (FIG. 23). There was no significant TGF-beta1 mRNA down-regulation in those groups (data not shown).

Example 20

Figure 24:
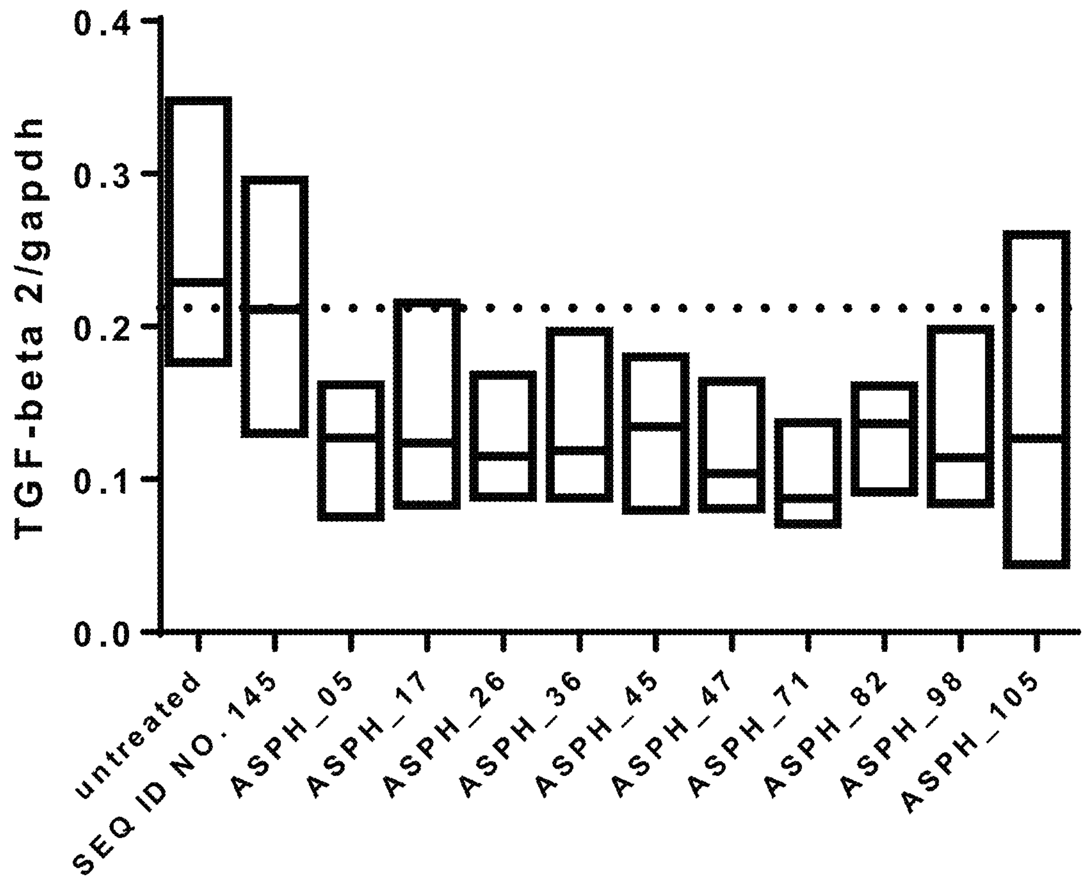
FIG. 24 presents TGF-beta2 mRNA expression in subcutaneous human renal cell carcinomas 786-O tumors. Mice were treated with a daily injection of 50 mg/kg oligonucleotides for five consecutive days. TGF-beta2 and GAPDH mRNA expression was detected by bDNA. Data—representing TGF-beta2 to GAPDH mRNA ratio—are shown as a box plot in which median values and min. and max. values are presented (data expressed as n=10, except for ASPH71 group n=9).

Mice bearing human 786-O renal cell carcinoma subcutaneous tumors on both left and right flanks were treated with a daily injection of 50 mg/kg oligonucleotides for five consecutive days. The tumors were collected 24 hours after the last treatment and snap frozen. TGF-beta mRNA expression in tumors was detected by bDNA assay. There was significant down-regulation of TGF-beta2 mRNA in tumors treated with ASPH05, ASPH17, ASPH26, ASPH36, ASPH45, ASPH47, ASPH71, ASPH82, ASPH98, and ASPH105 (FIG. 24). Data—representing TGF-beta2 to GAPDH mRNA ratio—are shown as a box plot in which median values and min. and max. values are presented (data expressed as n=10, except for ASPH71 group n=9).

Example 21

Figure 26A:
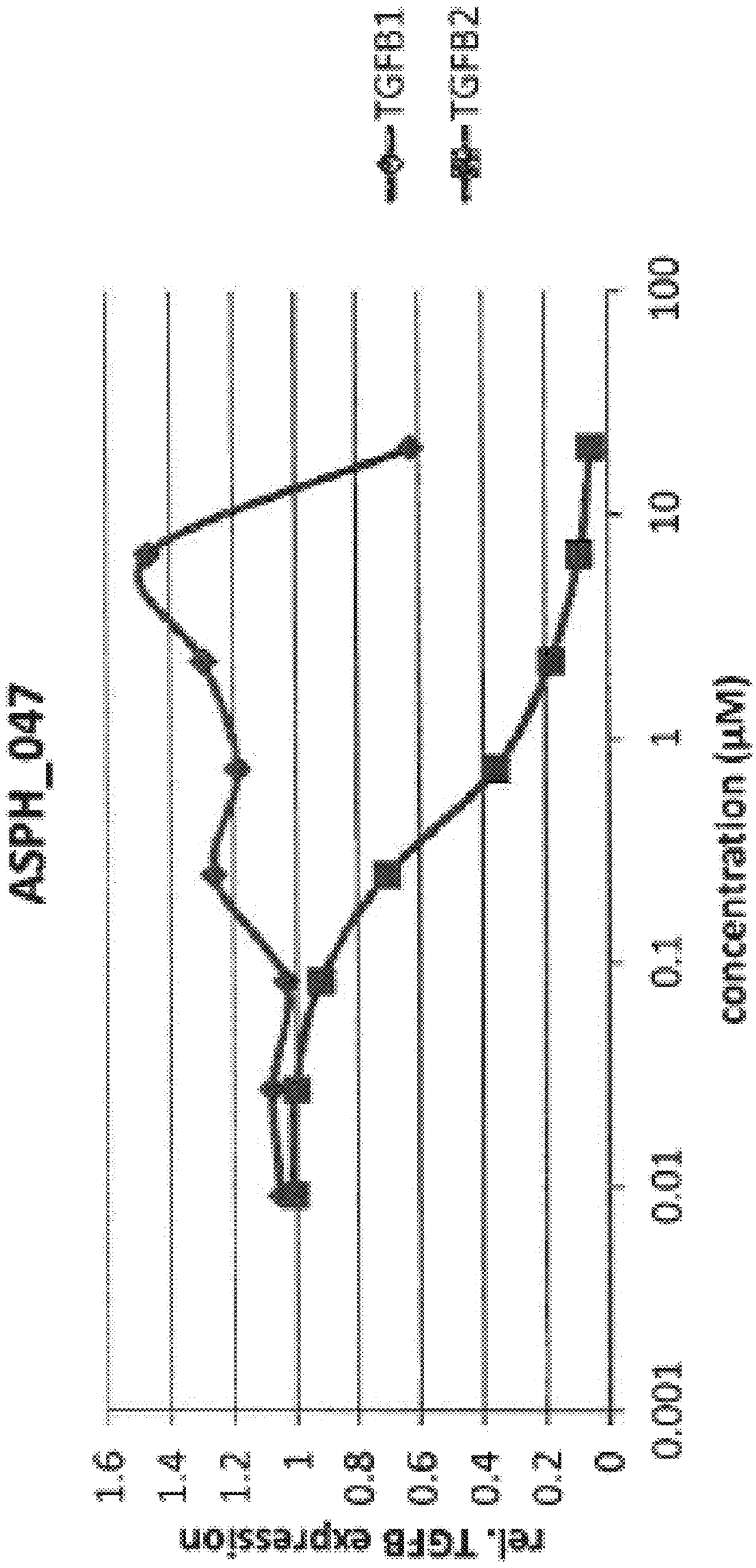
FIG. 26*a*, FIG. 26*b*, FIG. 26*c*, FIG. 26*d*, FIG. 26*e*, and FIG. 26*f* depict the inhibiting effect of oligonucleotides of the present invention on the expression of TGF-beta1 and TGF-beta2 protein. Panc-1 cells were transfected with 20, 6.67, 2.22, 0.74, 0.25, 0.08 or 0.009 μM of the modified oligonucleotides ASPH47 (FIG. 26*a*), ASPH1047 (FIG. 26*b*), ASPH1106 (FIG. 26*c*), ASPH1132 (FIG. 26*d*), or ASPH47 in combination with ASPH1047 (FIG. 26*e*). Negative control is the scrambled oligonucleotide (scrLNA) of SEQ ID No. 145 (FIG. 26*f*) in concentrations of 40, 13.33, 4.44, 1.48, 0.49, 0.16, 0.05, or 0.02 μM. TGF-beta1 (diamonds) and TGF-beta2 protein (squares) levels in cell supernatants were determined by ELISA.
Figure 26B:
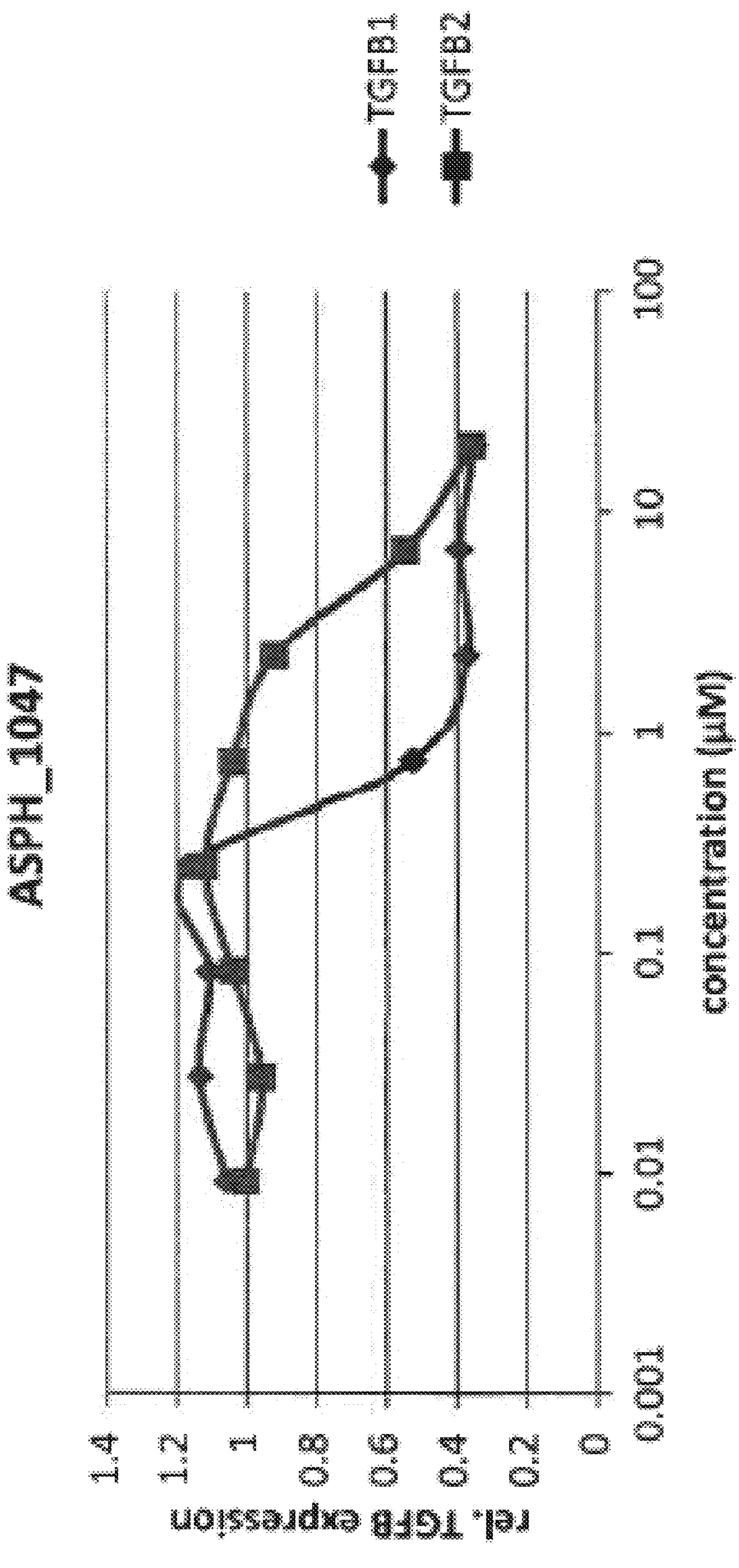
Figure 26C:
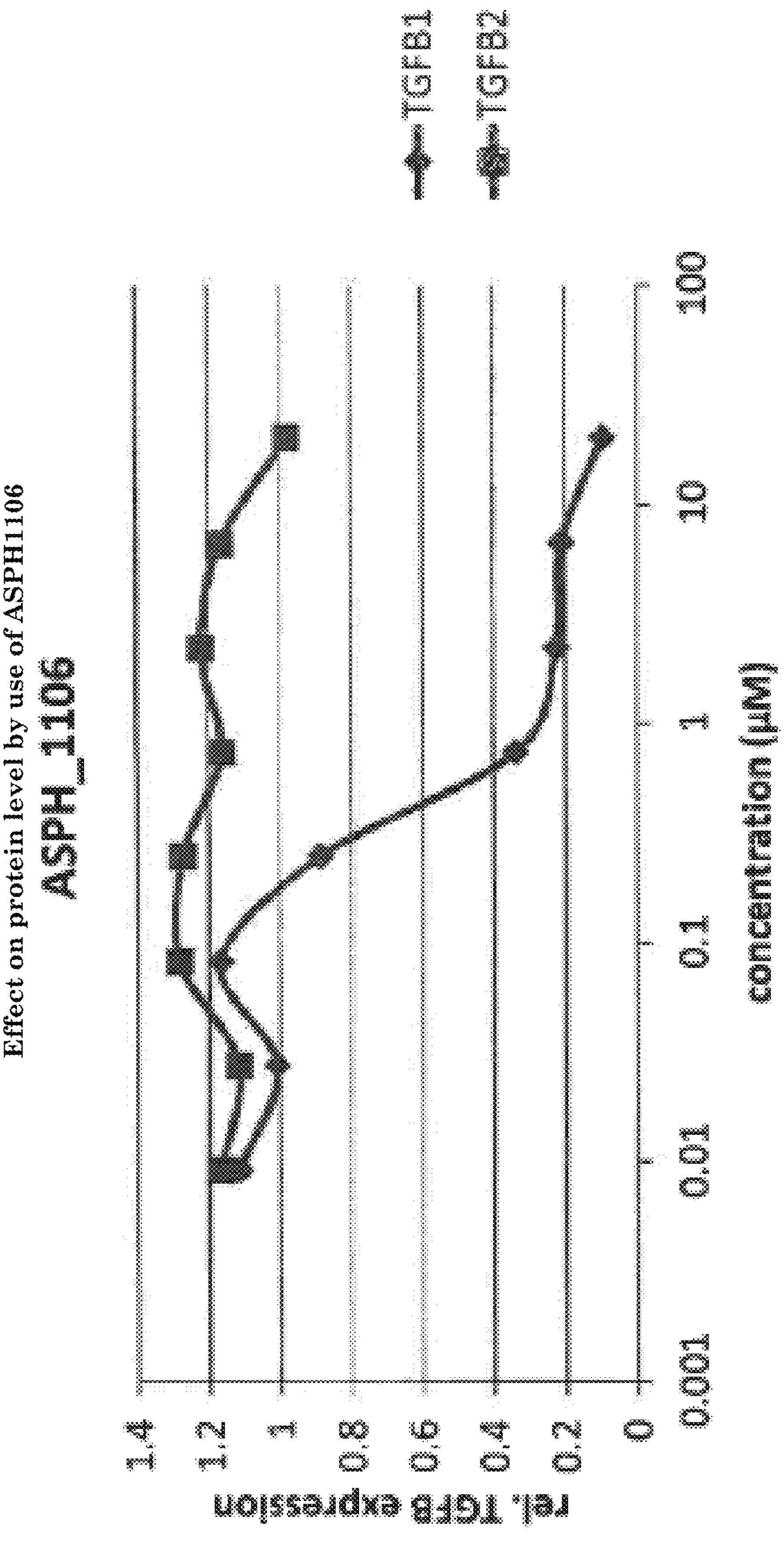
Figure 26D:
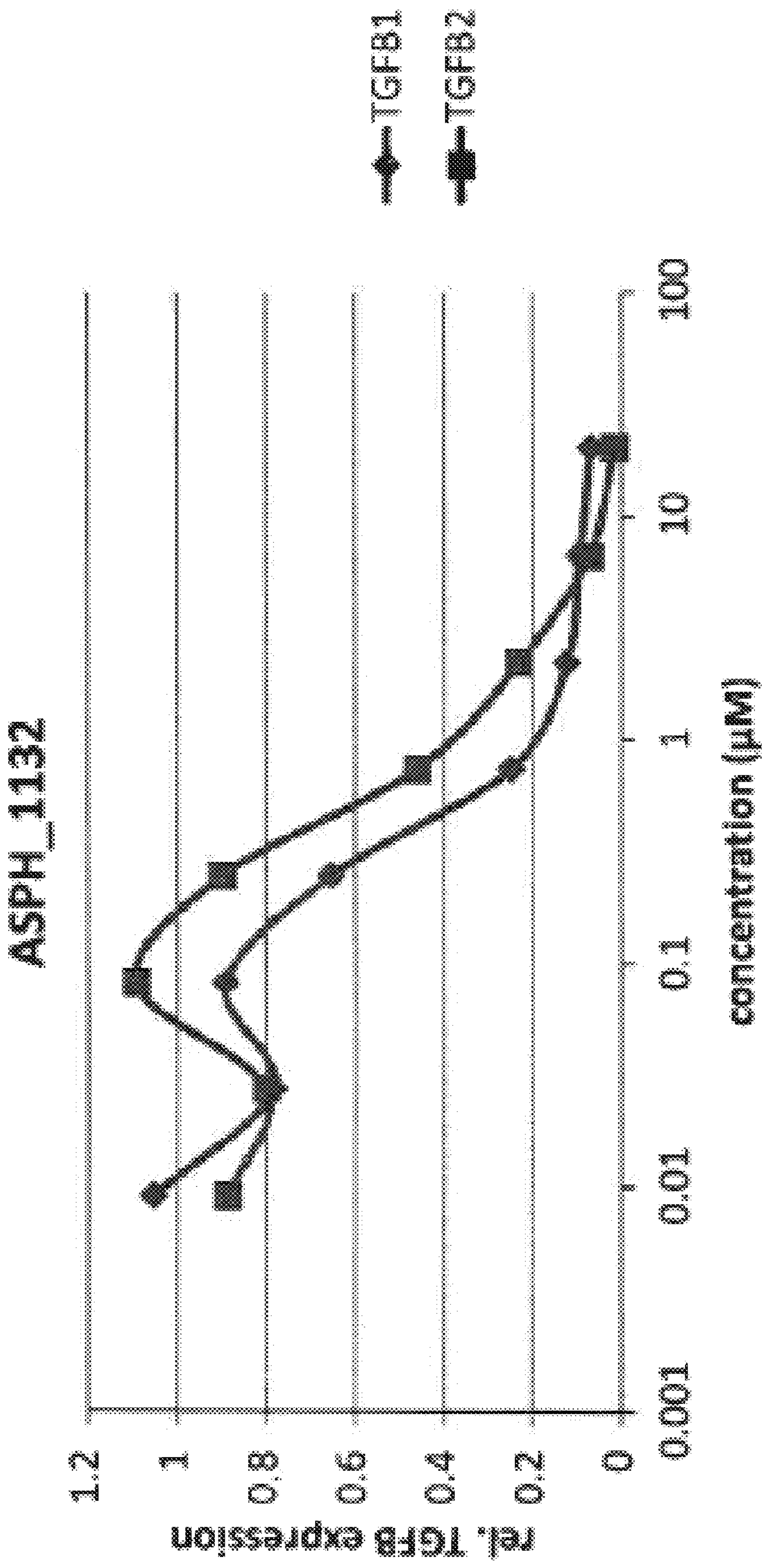
Figure 26E:
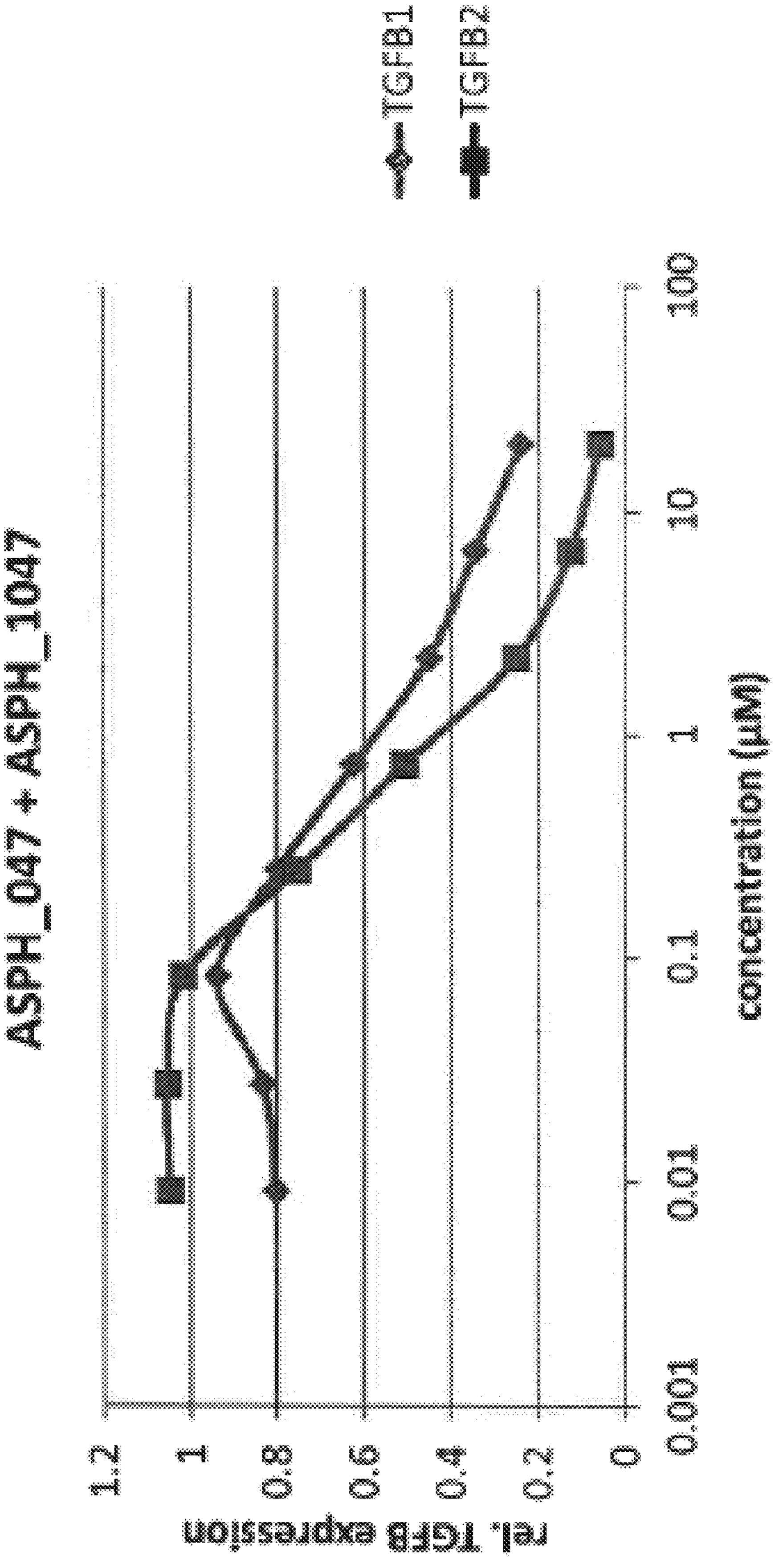
Figure 26F:
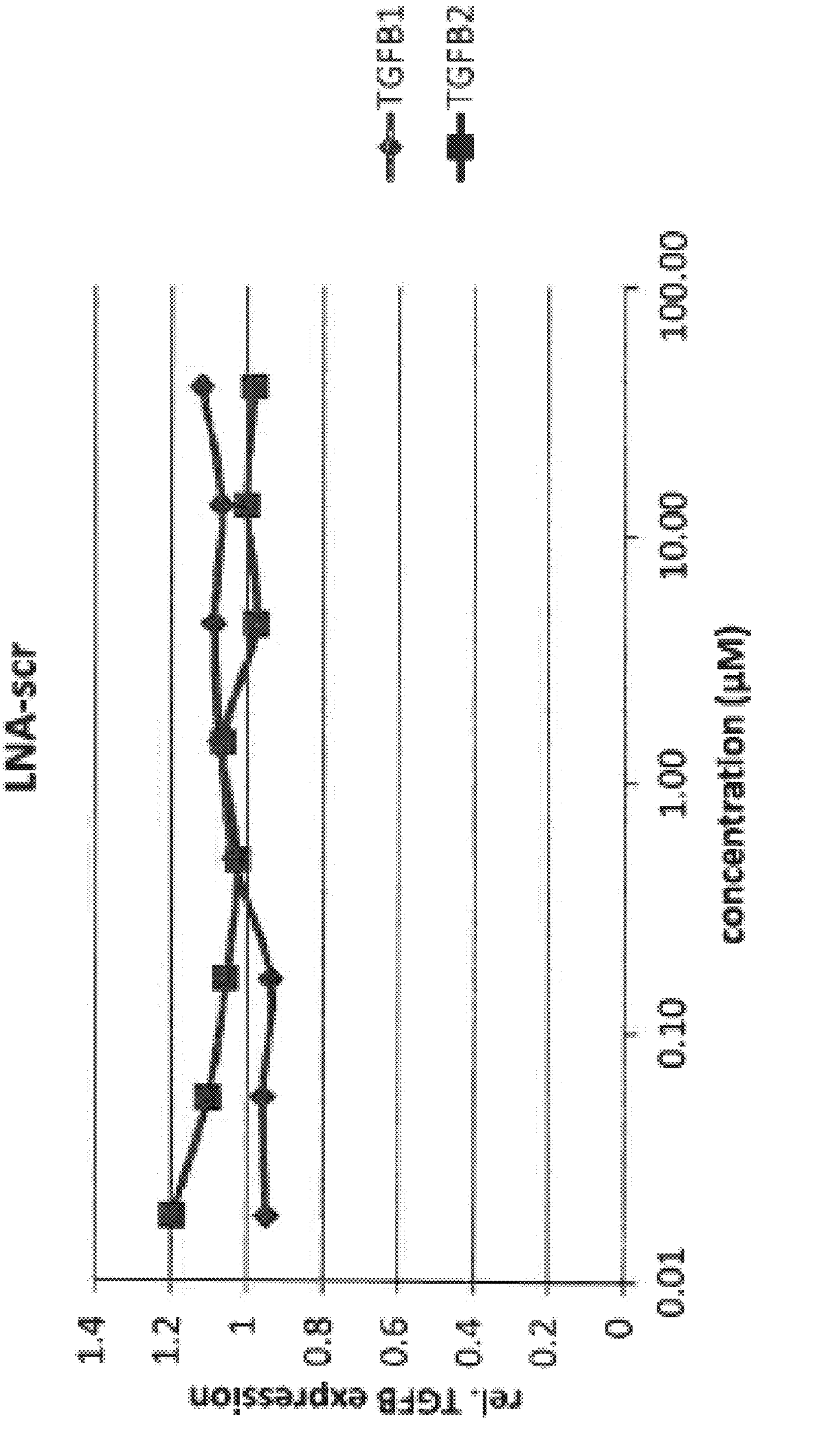

Human Panc-1 pancreatic cancer cells were transfected with 20, 6.67, 2.22, 0.74, 0.25, 0.08 or 0.009 μM of the modified oligonucleotides ASPH47, ASPH1047, ASPH1106, ASPH1132, or ASPH47 in combination with ASPH1047; results are shown in FIG. 26*a* to 26*e*). Negative control is the scrambled oligonucleotide (scrLNA) of SEQ ID No. 145 (FIG. 26*f*). All cells were transfected in the absence of transfecting agent (gymnotic transfection or gymnotic delivery). The modified oligonucleotides were added to the cells for 3 days, which were incubated at 37° C. Thereafter medium was exchanged with fresh oligonucleotide containing medium and cells were incubated for further 4 days at 37° C. TGF-beta1 and TGF-beta2 protein levels in cell supernatants were determined by ELISA. ASPH47 specifically inhibits the expression of TGF-beta2 in a dose-dependent manner and does not have any target inhibiting effect on TGF-beta1 (FIG. 26*a*). ASPH1047 specifically inhibits the expression of TGF-beta1 and does not have any target inhibiting effect on TGF-beta2 (FIG. 26*b*), or only a slight TGF-beta2 inhibiting effect at higher concentrations. Also ASPH1106 inhibits TGF-beta1 expression in a dose dependent manner (FIG. 26*c*). The pan-specific ASPH 1132 shows a dose-dependent inhibition of the expression of TGF-beta1 and TGF-beta2 protein (FIG. 26*d*). When ASPH47 and ASPH1047 are combined, the expression of both, TGF-beta1 and TGF-beta2 protein is inhibited in a dose dependent manner (FIG. 26*e*). The scrLNA of SEQ ID No. 145 does not show any inhibiting effect on the expression of neither TGF-beta1 nor TGF-beta2, even if the concentrations were doubled (40, 13.33, 4.44, 1.48, 0.49, 0.16, 0.05, or 0.02 μM) in comparison to the individual concentrations of ASPH47, ASPH1047, ASPH1106, or ASPH1132. Results for TGF-beta1 are indicated in diamonds, and results for TGF-beta2 in squares in FIG. 26*a*, FIG. 26*b*, FIG. 26*c*, FIG. 26*d*, FIG. 26*e*, FIG. 26*f*.

Example 22

Figure 27A:
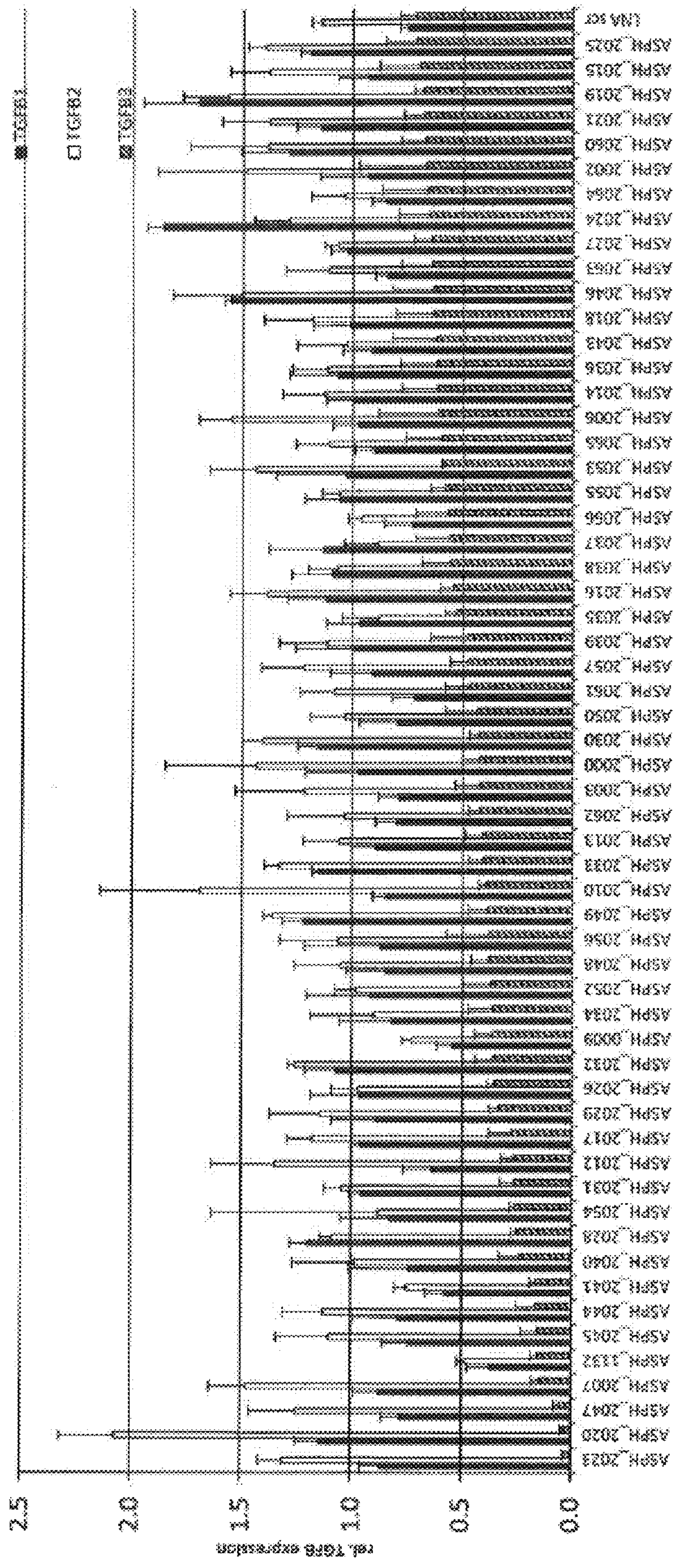
FIG. 27*a* and FIG. 27*b* present the inhibiting effect of oligonucleotides of the present invention on the expression of TGF-beta1, TGF-beta2, and TGF-beta3. Panc-1 cells (FIG. 27*a*) or RenCa cells (FIG. 27*b*) were transfected with 3.3 μM of different TGF-beta specific oligonucleotides in the absence of a transfecting agent. The expression of TGF-beta1 (black column), TGF-beta2 (white column) and TGF-beta3 (striped column) mRNA was determined 72 h after transfection.
Figure 27B:
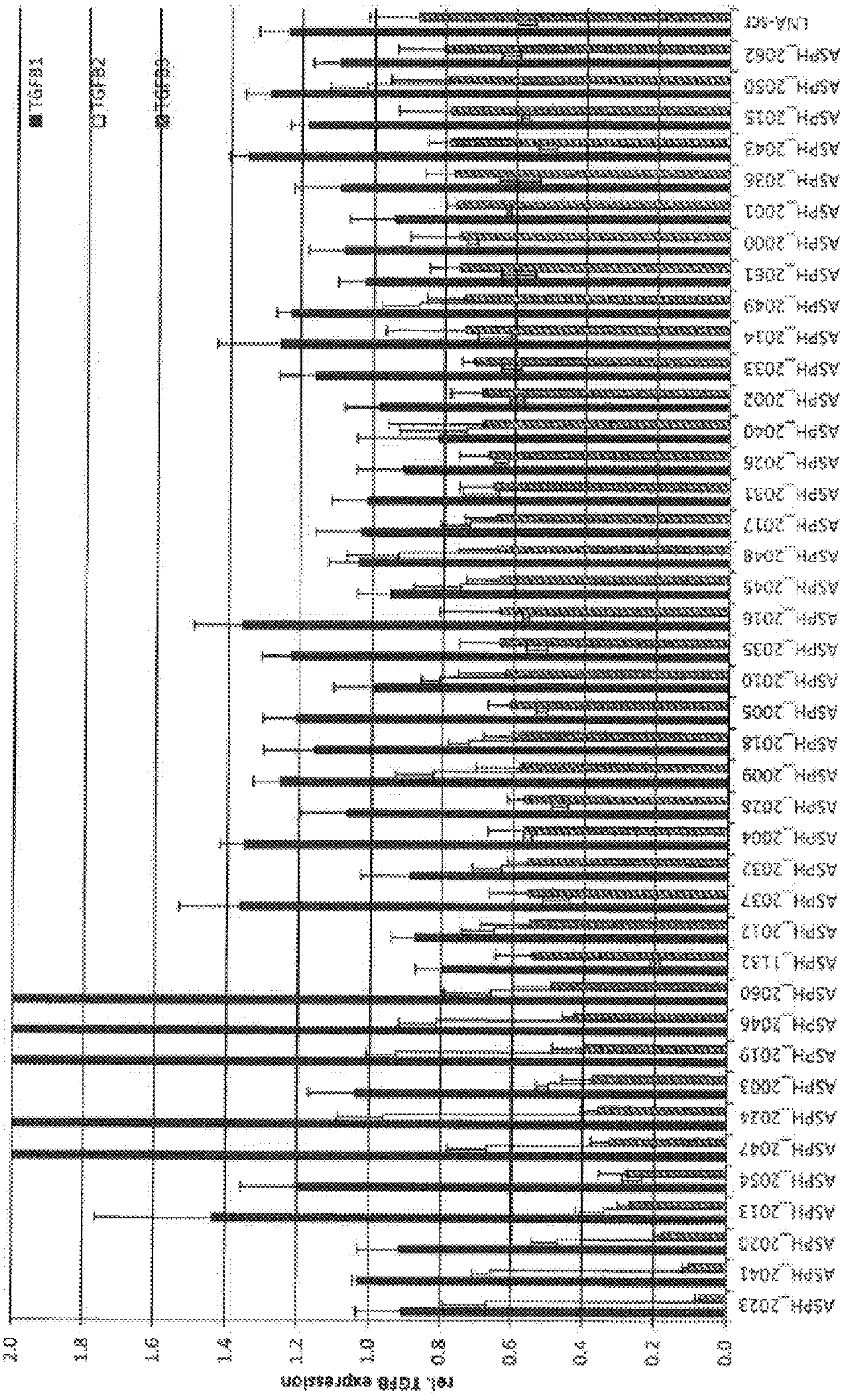

Human Panc-1 pancreatic cancer cells (FIG. 27*a*) or mouse RenCa renal cell carcinoma cells (FIG. 27*b*) were treated with 3.3 μM of ASPH0009, ASPH1132, ASPH2000, ASPH2001, ASPH2002, ASPH2003, ASPH2004, ASPH2005, ASPH2006, ASPH2007, ASPH2009, ASPH2010, ASPH2012, ASPH2013, ASPH2014 ASPH2015, ASPH2016, ASPH2017, ASPH2018, ASPH2019, ASPH2020, ASPH2021, ASPH2023, ASPH2024, ASPH2025, ASPH23026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2043, ASPH2044, ASPH2045, ASPH2046, ASPH2047, ASPH2048, ASPH2049, ASPH2050, ASPH2052, ASPH2053, ASPH2054, ASPH2055, ASPH2056, ASPH2057, ASPH2060, ASPH2061, ASPH2062, ASPH2063, ASPH2064, ASPH2065, or ASPH2066 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta3 mRNA is shown in FIG. 27*a* and FIG. 27*b*. As anticipated from the sequences, the TGF-beta1, -beta2 and -beta3 reactive oligonucleotide ASPH 0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 23

Figure 28:
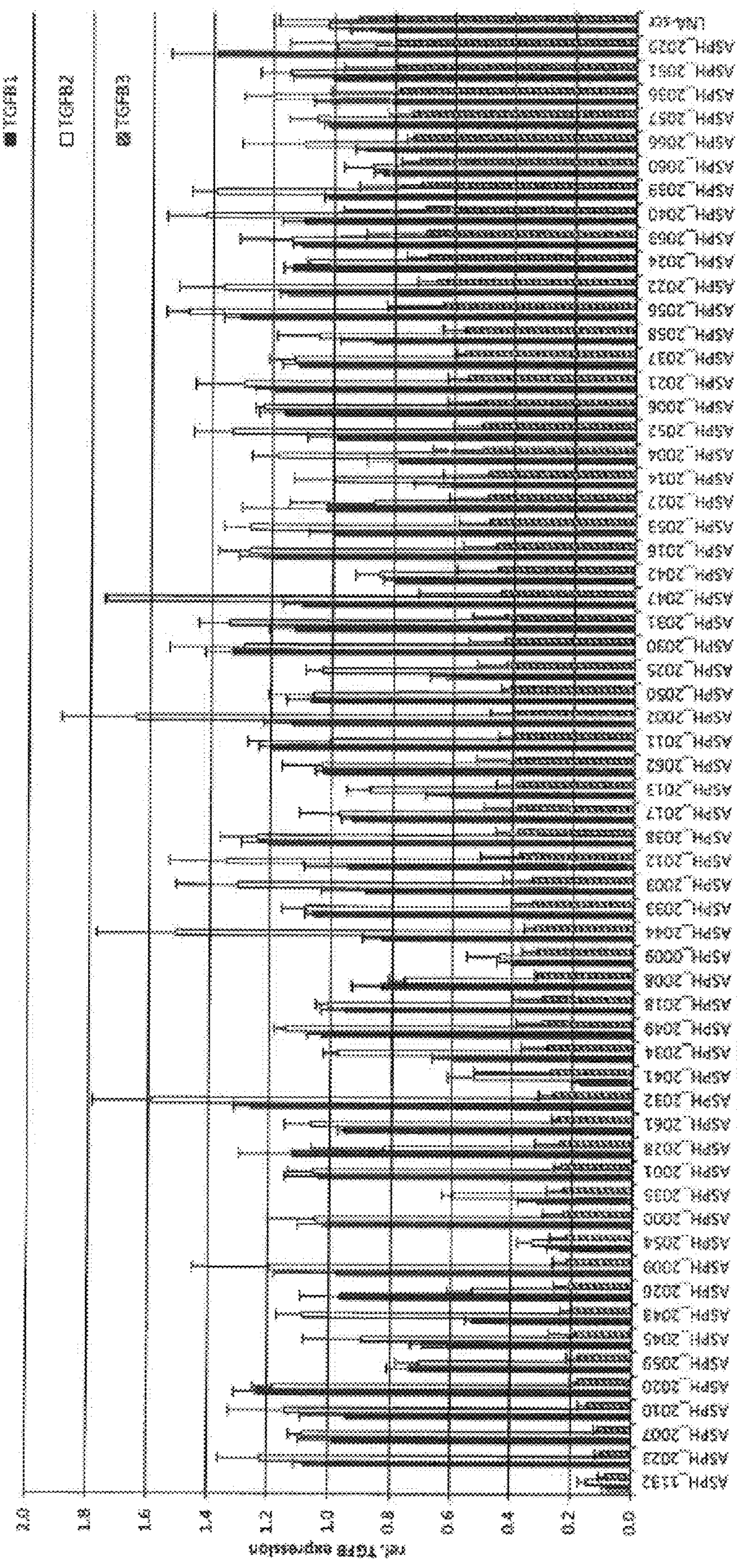
FIG. 28 depicts the inhibiting effect of oligonucleotides of the present invention on the expression of TGF-beta1, TGF-beta2, and TGF-beta3. A172 glioma cells were transfected with 10 nM of different TGF-beta specific oligonucleotides in the presence of transfecting agent. The expression of TGF-beta1 (black column), TGF-beta2 (white column) and TGF-beta3 (striped column) mRNA was determined 24 h after transfection.

Human A172 glioma cells were treated for 24 h with 10 nM (in the presence of a transfecting agent), of ASPH0009, ASPH1132, ASPH2000, ASPH2001, ASPH2002, ASPH2003, ASPH2004, ASPH2006, ASPH2007, ASPH2008, ASPH2009, ASPH2010, ASPH2011, ASPH2012, ASPH2013, ASPH2014, ASPH2016, ASPH2017, ASPH2018, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2047, ASPH2049, ASPH2050, ASPH2051, ASPH2052, ASPH2053, ASPH2054, ASPH2056, ASPH2057, ASPH2058, ASPH2059, ASPH2060, ASPH2061, ASPH2062, ASPH2063, or ASPH2066. The expression of TGF-beta1 (black column), TGF-beta2 (white column) and TGF-beta3 (striped column) mRNA was then determined from cell extracts by bDNA assay. Significant reduction of the expression of TGF-beta3 mRNA is shown in FIG. 28. As anticipated from the sequences, the TGF-beta1, -beta2 and -beta3 reactive oligonucleotide) ASPH_0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 24

Target mRNA downregulation in rabbit cells Sequences of selected oligonucleotides were aligned with rabbit mRNA sequences of TGF-beta1 and 2. ASPH 0036 (TGF-beta2 selective antisense oligonucleotide, based on human mRNA sequence) showed 100% homology with rabbit TGF-beta2 mRNA, while ASPH 1059 (TGF-beta1 selective antisense oligonucleotide, based on human mRNA sequence) showed 100% homology with rabbit TGF-beta1 mRNA.

Rabbit Rab-9 skin fibroblasts were treated with 5 nM or 20 nM of either ASPH_0036 and ASPH_1059 in the presence of a transfecting agent for 24 hr. The expression of TGF-beta1 and TGF-beta2 mRNA was then determined in cell extracts by bDNA assay. Significant reduction of the expression of TGF-beta1 mRNA (51 and 77% at 5 and 20 nM, respectively) was achieved with ASPH 1059. Significant reduction of TGF-beta2 mRNA (79 and 80% at 5 and 20 nM, respectively) was achieved with ASPH_0036.

Example 25

Tissue biodistribution and target mRNA downregulation following systemic administration of ASPH_0047 in Balb/c mice.

Balb/C mice were treated with a single subcutaneous injection of ASPH_0047 (formulated in sterile physiological saline) at 5, 20 and 50 mg/kg animal body weight. Plasma and tissues were collected at the indicated times (from 3 individual animals), immediately snap-frozen and stored at −80° C. until analysis with an AEX-HPLC method (plasma/tissue PK) or for measurement of TGF-β2 and GAPDH mRNA levels by bDNA assay. TGF-β2 mRNA levels were expressed relative to GAPDH mRNA expression level in corresponding samples.

Figure 29A:
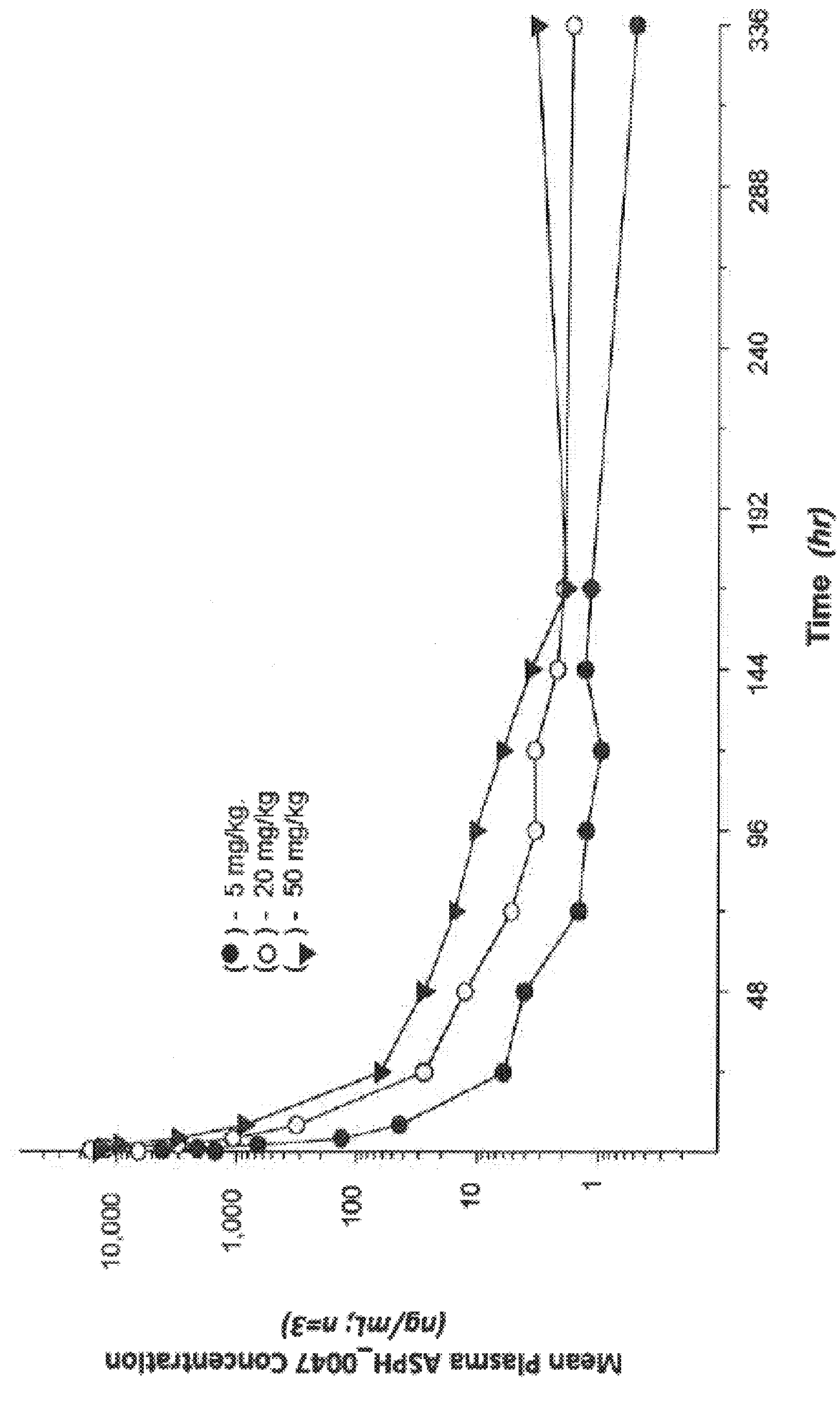
FIG. 29*a* and FIG. 29*b* present a compared analysis of time-dependent plasma (29a) and kidney (29b) concentration (PK profiles; with values expressed in μg/mL or μg/gr) and downregulation of TGF-β2 mRNA (PD profile) in kidney following single subcutaneous bolus administration of 50 mg/kg of ASPH_0047 to Balb/c mice.
Figure 29B:
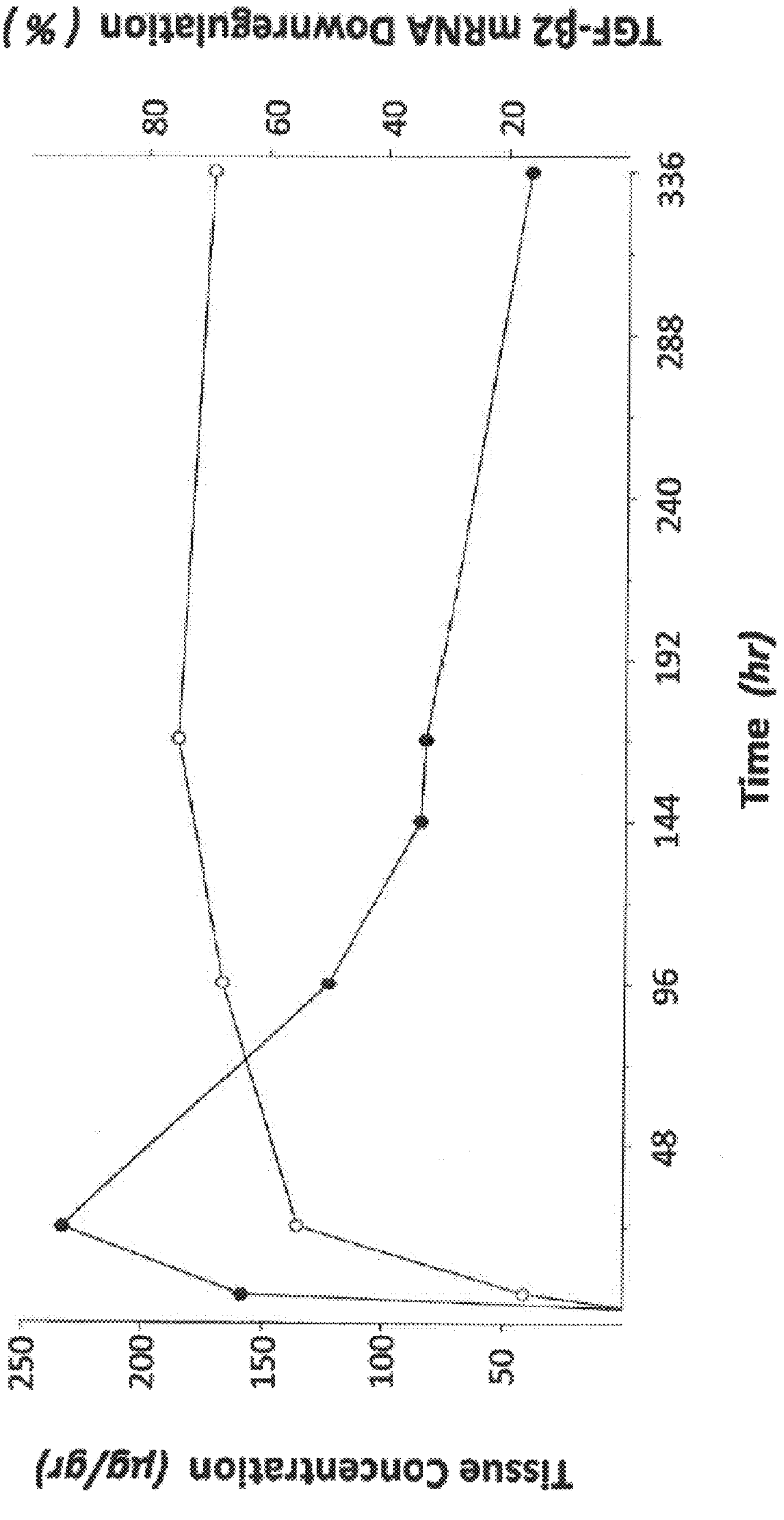

The data depict that a single subcutaneous bolus administration of 50 mg/kg ASPH_0047 resulted in rapid transfer of the drug from subcutaneous to circulating blood compartments ($T_{MAX}$ of ~5-30 min), biphasic pharmacokinetic profile in plasma, with rapid initial elimination phase (within the first 24 hrs), followed by long terminal half-life (FIG. 29*a*). It is further demonstrated that a marked long-lasting accumulation of the drug in various selected tissues. The major target organ (highest exposure/$C_{MAX}$) is the kidney, then the liver, skin and spleen, and lowest in the brain (data not shown). As also depicted in FIG. 29*b*, ASPH_0047 remained in the kidney tissue with pharmacological relevant doses (~50 μg/gr, equivalent to 10 μM) from 24 h and for up to 14 days, with consequent long-lasting and marked suppression of TGF-β2 mRNA expression in the kidney tissue, with effective ~80% target mRNA downregulation observed for at least 14 days.

Example 26

Figure 30:
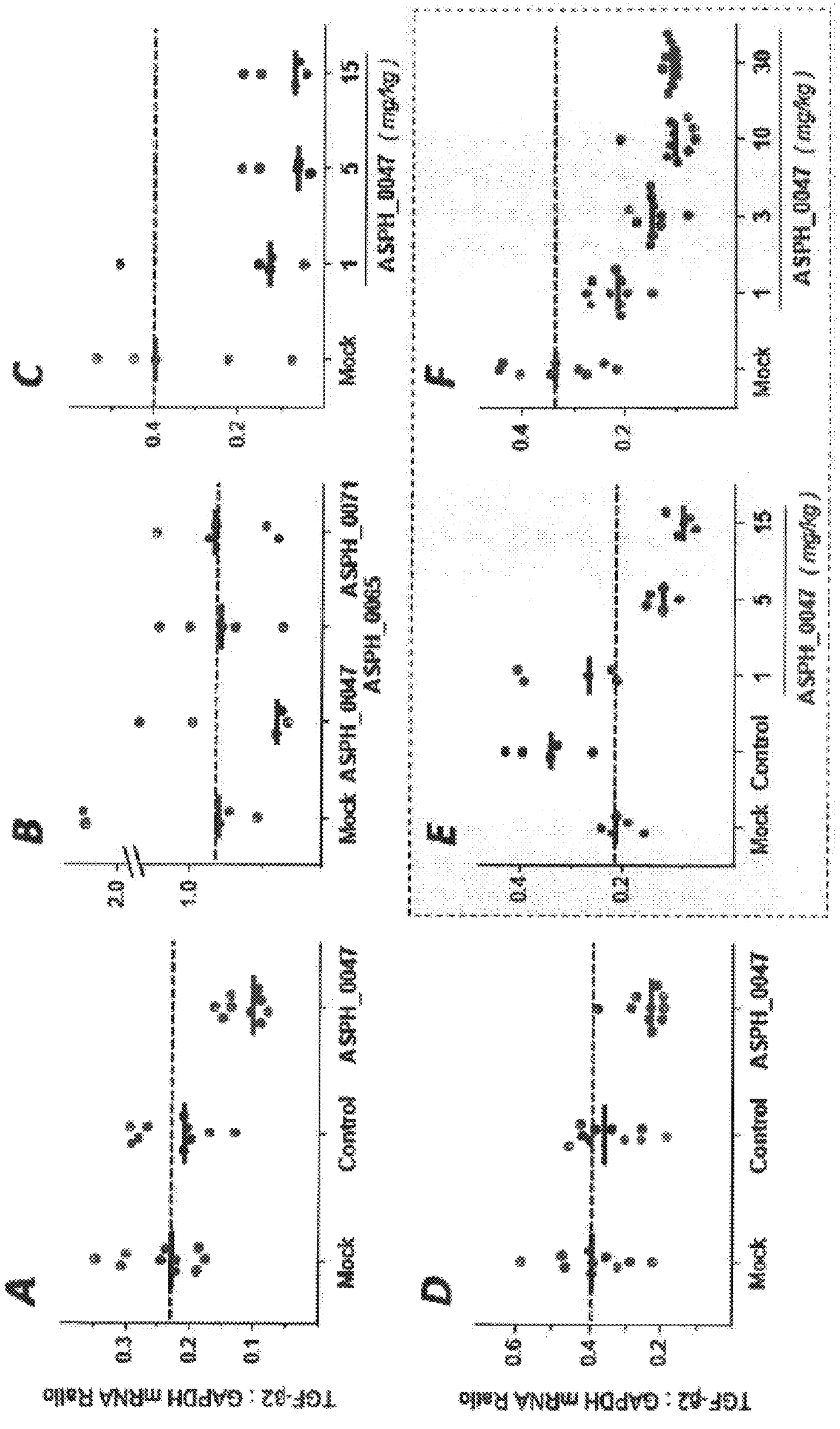
FIG. 30 depicts TGF-β2 mRNA downregulation in established subcutaneous tumors (FIG. 30A-D) or kidney (FIG. 30E-F) in immunodeficient mouse following subcutaneous repeated administration of ASPH_0047 or control oligonucleotide. TGF-beta2 and GAPDH mRNA expression was detected by bDNA. Results are expressed as TGF-beta2/GAPDH mRNA ratio, and each individual tested sample is represented with line indicating median values.

Immunodeficient mice were injected subcutaneously with human 786-O renal cell carcinoma cells (FIG. 30A), pancreatic Panc1 cancer cells (FIG. 30B, C), or mouse SMA-560 glioma cells (FIG. 30D). When subcutaneous tumors reached the size of 100-300 $mm^3$ (established tumors), animals were treated subcutaneously, QDx5, with saline (Mock), control oligonucleotide (Control; 50 mg/kg), inactive oligonucleotides in this context (e.g., ASPH_0065 and ASPH_0071; 50 mg/kg) or ASPH_0047 at 50 mg/kg, or the indicated doses. Tumors (FIG. 30A-D) and kidneys (FIG. 30E-F) were collected 24 hr after the last administration. Tumors/kidneys were then further processed for determination of TGF-□2 and GAPDH mRNA levels by bDNA assay. In these experiments, control oligonucleotide was a 18-mer, 3+3 LNA gapmer scrambled sequence. Results are expressed as TGF-beta2/GAPDH mRNA ratio, and each individual tested sample is represented with median values indicated as red line. Under described experimental conditions (schedule and route of administration), systemic repeated administrations of ASPH 0047 in Balb/c mice led to a sequence-specific downregulation of TGF-beta 2 mRNA in established subcutaneous tumors and kidneys.

Example 27

Figure 31:
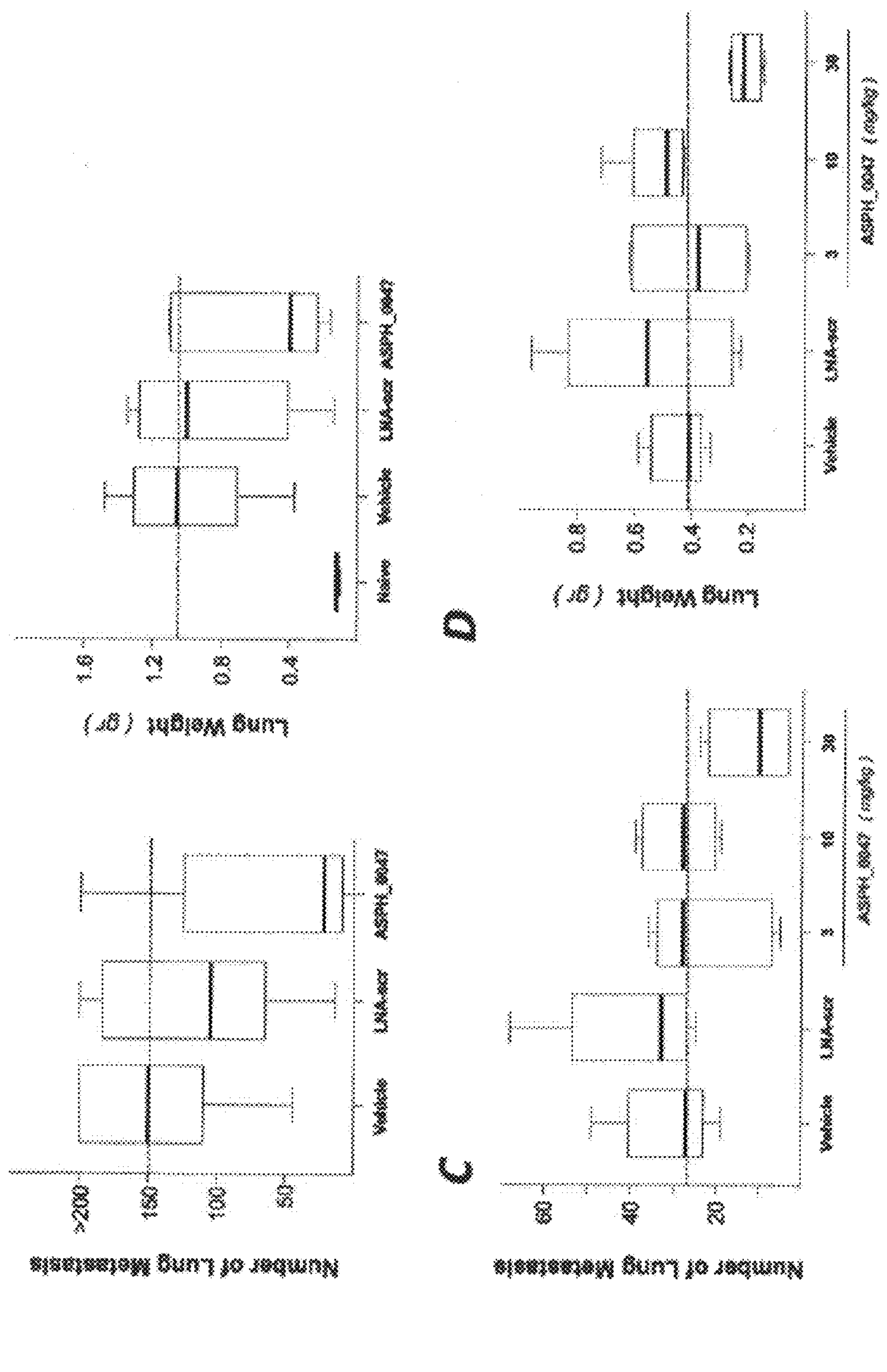
FIG. 31 shows the effect of systemic treatment of Balb/c mice with ASPH_0047 (selective TGF-b2 antisense oligonucleotide) on lung metastasis in orthotopic and in i.v. mouse Renca renal carcinoma model. Level of lung metastasis was determined by either number of metastasis or based on lung weight. Results are shown as a box plot in which median values, upper and lower quartiles, and $90^{th}$ and $10^{th}$ percentiles are presented.

Balb/c mice were injected with mouse Renca cells into renal subcapsule (FIG. 31A, B) or i.v. (FIG. 31C, D) on Day 0. Systemic treatment with vehicle or indicated oligonucleotides started on Day 7 (FIG. 31A; 50 mg/kg, s.c., twice weekly), on Day 1 (FIG. 31B; 12.5 mg/kg, s.c., twice weekly) for two consecutive weeks, or on Day 7 (FIGS. 31C and 31D; indicated doses, s.c., twice weekly) for 26-27 days. Number of lung metastasis was macroscopically evaluated, and level of lung metastasis was determined by either number of metastasis (FIG. 31A, C) or based on lung weight (FIG. 31B, D). Results are represented as box plot; with median values, upper and lower quartiles, and 90th and 10th percentiles. Under described experimental designs, Balb/c mice treated with ASPH_0047 showed a reduced number of lung metastasis or reduced lung weight (lung weight correlates to extent of lung metastasis) in mouse Renca RCC models.

Example 28

Figure 32:
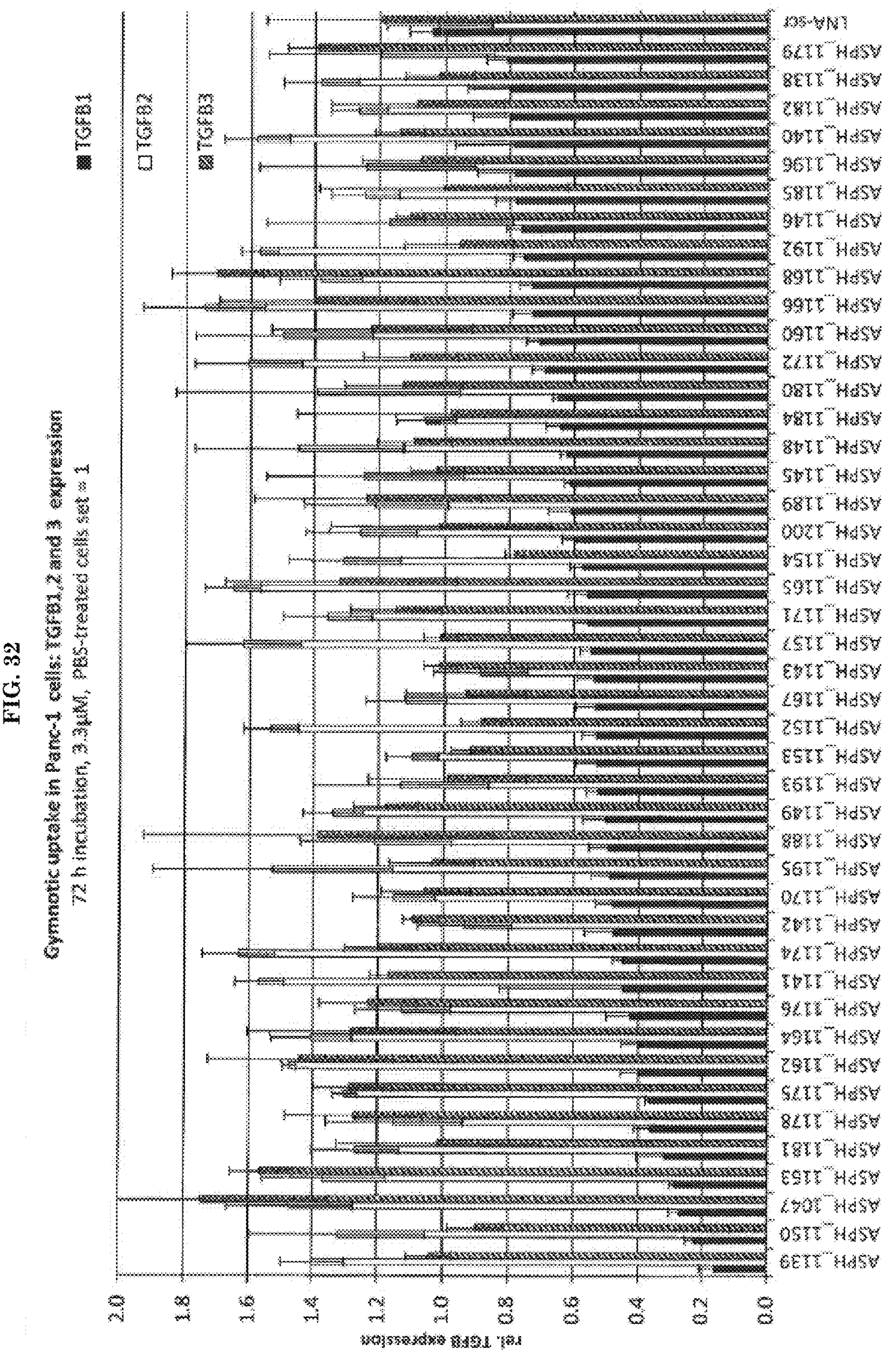
FIG. 32 presents human Panc-1 pancreatic cancer cells were treated with 3.3 μM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection.
Figure 33:
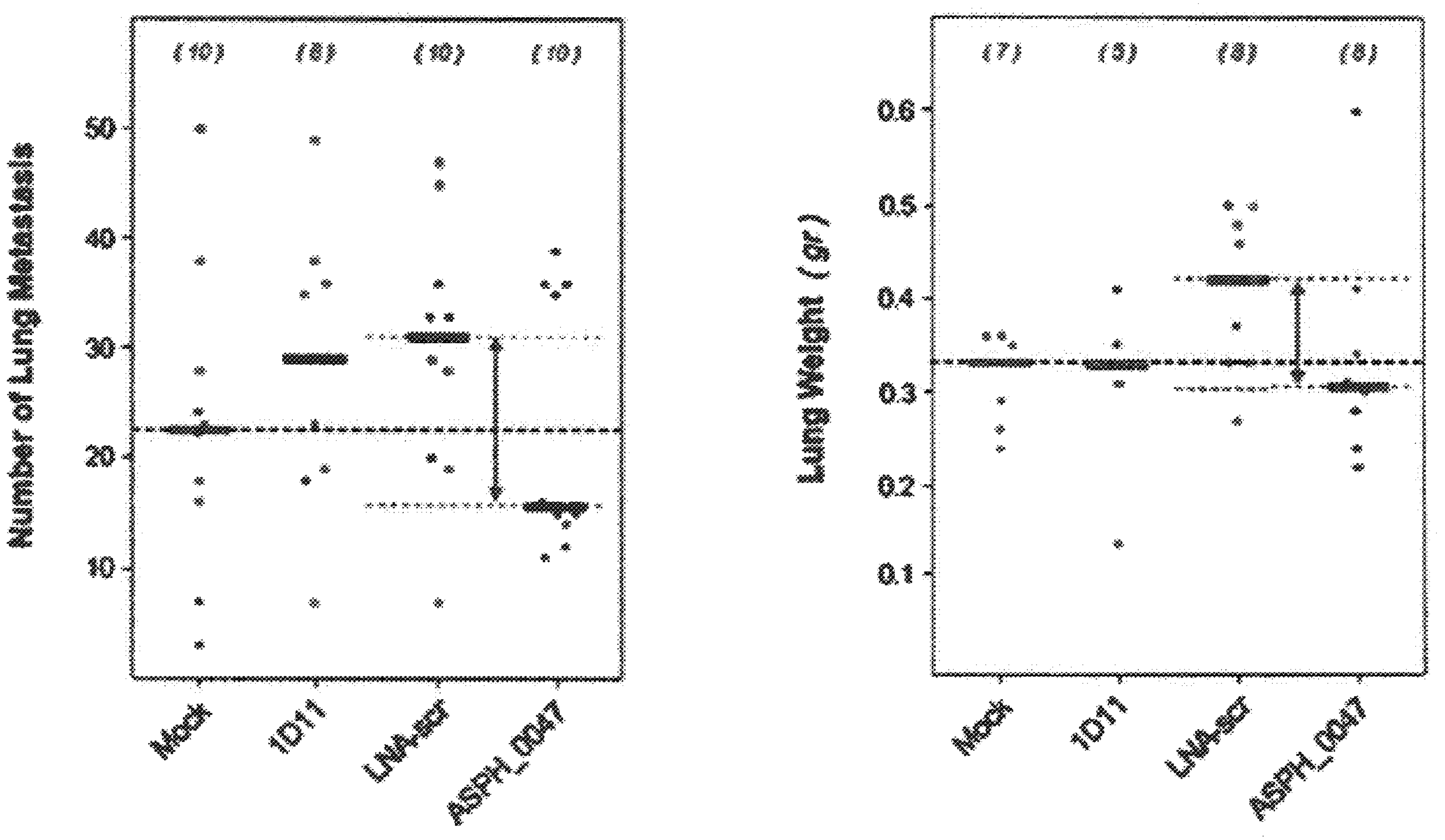
FIG. 33 depicts the effect of systemic treatment of Balb/c mice with ASPH_0047 on lung metastasis in orthotopic mouse 4T1 mammary carcinoma model. Data for each individual animal is represented with median values indicated as bold black line.

Human Panc-1 pancreatic cancer cells were treated with 3.3 μM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is shown in FIG. 32. The selective TGF-beta1 oligonucleotides only significantly inhibit TGF-beta1 mRNA expression while the control oligonucleotide LNA-scr does not affect expression of any TGF-beta isoform.

Example 29

Balb/c mice were injected with mouse 4T1 cells into mammary fat pad on Day 0. Systemic treatment with saline (Mock), pan-TGF-beta antibody (1D11), control oligonucleotide (LNA-scr), or ASPH_0047 started on Day 3 (30 mg/kg, s.c., twice weekly) and continued until D28, when animals were sacrificed. Number of lung metastasis was macroscopically evaluated, and level of lung metastasis was determined by either number of metastasis (left panel) or based on lung weight (right panel).

Example 30

CB17 SCID or Balb/c nude mice (n=3-5, except ASPH 0018 n=1 and ASPH_0037 n=2) were treated with 14-15 mg/kg of indicated LNA-modified oligonucleotides for four or five consecutive days (Q1Dx4-5). Plasma was collected 24 h after the last treatment and ALT levels were determined. Results are expressed as median. The following Table 7 shows liver toxicity of systemically administered LNA-modified oligonucleotides:

| Name | ALT (units/l) | Name | ALT (units/l) |
|---|---|---|---|
| ASPH_0001 | 20.5 | ASPH_0115 | 985.5 |
| ASPH_0003 | 20.0 | ASPH_0190 | 902.0 |
| ASPH_0005 | 33.0 | ASPH_0191 | 36.5 |
| ASPH_0009 | 834.0 | ASPH_0192 | 49.5 |
| ASPH_0017 | 55.0 | ASPH_0193 | 35.0 |
| ASPH_0018 | 7723.0 | ASPH_0005_C1 | 25.5 |
| ASPH_0022 | 28.5 | ASPH_0005_C2 | 35.5 |
| ASPH_0026 | 77.0 | ASPH_0005_C3 | 25.0 |
| ASPH_0027 | 75.0 | ASPH_0036_C1 | 34.0 |
| ASPH_0035 | 25.0 | ASPH_0036_C2 | 26.0 |
| ASPH_0036 | 131.5 | ASPH_0036_C3 | 39.0 |
| ASPH_0037 | 161.0 | ASPH_0045_C1 | 38.5 |
| ASPH_0041 | 655.0 | ASPH_0045_C2 | 23.5 |
| ASPH_0045 | 27.5 | ASPH_0045_C3 | 65.0 |
| ASPH_0046 | 3199.0 | ASPH_0047_C1 | 35.5 |
| ASPH_0047 | 42.5 | ASPH_0047_C2 | 30.0 |
| ASPH_0048 | 29.5 | ASPH_0047_C3 | 29.5 |
| ASPH_0065 | 27.0 | ASPH_0047_C4 | 52.5 |
| ASPH_0069 | 32.5 | ASPH_0047_C5 | 28.0 |
| ASPH_0071 | 23.5 | ASPH_0047_C6 | 33.5 |
| ASPH_0080 | 34.0 | ASPH_0047_C7 | 37.0 |
| ASPH_0082 | 31.0 | ASPH_0047_C8 | 32.0 |
| ASPH_0098 | 33.0 | ASPH_0047_C9 | 49.0 |
| ASPH_0105 | 40.0 | ASPH_0047_C10 | 32.5 |

EMBODIMENTS

1. Oligonucleotide consisting of 12 to 18 nucleotides of the TGF-beta2 nucleic acid sequence of SEQ ID NO. 1, wherein one or more nucleotide(s) of the oligonucleotide is/are a LNA modified, wherein the modified nucleotide is a LNA, and/or an ENA, polyalkylene oxide-, 2'-fluoro-, 2'-O-methoxy-, and/or 2'O-methyl-modified nucleotide.
2. Oligonucleotide according to embodiment 1 consisting of 12 to 18 nucleotides of the region of nucleic acid no. 1380 to 1510, no. 1660 to 1680, no. 2390 to 2410, or no. 2740 to 2810 of the TGF-beta2 nucleic acid sequence of SEQ ID NO. 1.
3. Oligonucleotide according to any one of embodiments 1 or 2, wherein the modified nucleotide is located at the 5'- and/or 3'-end of the oligonucleotide.
4. Oligonucleotide according to any one of embodiments 1 to 3, wherein the oligonucleotide comprises a sequence selected from the group consisting of SEQ ID NO. 46, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 12, SEQ ID NO. 13, SEQ ID NO. 14, SEQ ID NO. 15, SEQ ID NO. 16, SEQ ID NO.17, SEQ ID NO. 18, SEQ ID NO. 25, SEQ ID NO. 31, SEQ ID NO. 35, SEQ ID NO. 44, SEQ ID NO. 47, SEQ ID NO. 57, SEQ ID NO. 61, SEQ ID NO. 63, SEQ ID NO. 73, SEQ ID NO. 95, and SEQ ID NO. 103.
5. Oligonucleotide according to embodiment 1 or 4, wherein the oligonucleotide is selected from the group consisting of CAAAGTATTTGGTCTCC (ASPH47), ACCTCCTTGGCGTAGTA (ASPH01), ACCTCCTTGGCGTAGTA (ASPH02), CCTCCTTGGCGTAGTA (ASPH03), CCTCCTTGGCGTAGTA (ASPH04), CTCCTTGGCGTAGTA (ASPH05), CTCCTTGGCGTAGTA (ASPH06), CTCCTTGGCGTAGTA (ASPH07), TCCTTGGCGTAGTA (ASPH08), CAGAAGTTGGCAT (ASPH09), CAGAAGTTGGCAT (ASPH10), CTGCCCGCGGAT (ASPH15), TCTGCCCGCGGAT (ASPH17), TCGCGCTCGCAGGC (ASPH22), GGATCTGCCCGCGGA (ASPH26), GGATCTGCCCGCGGA (ASPH27), CGATCCTCTTGCGCAT (ASPH30), GGCGGGATGGCAT (ASPH35), GACCAGATGCAGGA (ASPH36), CTTGCTCAGGATCTGCC (ASPH37), TCTGTAGGAGGGC (ASPH45), CCTTAAGCCATCCATGA (ASPH48), TCTGAACTAGTACCGCC (ASPH65), TACTATTATGGCATCCC (ASPH69), AGCGTAATTGGTCATCA (ASPH71), GCGACCGTGACCAGAT (ASPH80), AACTAGTACCGCCTTT (ASPH82), GCGCGACCGTGACC (ASPH98), ACCACTAGAGCACC (ASPH105), AGCGCGACCGTGA (ASPH111), GGATCGCCTCGAT (ASPH112), CTAGTACCGCCTT (ASPH115), CCGCGGATCGCC (ASPH119), GACCGTGACCAGAT (ASPH121), GACCGTGACCAGAT (ASPH153).
6. Pharmaceutical composition comprising the oligonucleotide according to any one of embodiments 1 to 5 and a pharmaceutically acceptable carrier.
7. Oligonucleotide according to any one of embodiments 1 to 5 or pharmaceutical composition according to claim 6 for use in a method of preventing and/or treating a malignant and/or benign tumor, fibrosis, cirrhosis, scleroderma or related dermatologic diseases, or a CNS disease.
8. Oligonucleotide or pharmaceutical composition for use according to embodiment 7, wherein the tumor is selected from the group consisting of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngloma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, or is selected from the group of bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

What is claimed is:

1. A method of inhibiting and/or treating a malignant and/or a benign tumor, fibrosis, cirrhosis, scleroderma or a related dermatologic disease, or a CNS disease comprising administering an oligonucleotide to a subject in need thereof, wherein one or more nucleotide(s) of the oligonucleotide is/are LNA modified nucleotides, wherein the modified nucleotide is a LNA, and/or an ENA, polyalkylene oxide-, 2'-fluoro-, 2'-O-methoxy-, and/or 2'O-methyl-modified nucleotide; wherein said oligonucleotide is GTCTTGCAGGTGGA (SEQ. ID. NO. 252), wherein nucleotides in bold letters are LNA, and wherein the malignant and/or benign tumor, fibrosis, cirrhosis, scleroderma or related dermatologic disease, or CNS disease is at least one of solid tumors, blood born tumors, leukemia, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangioblastoma, Hodgkins-lymphoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, choroidcarcinoma, cystadenocarcinoma, embryonal carcinoma, epithelial carcinoma, esophageal cancer, cervical carcinoma, colon carcinoma, colorectal carcinoma, endometrial cancer, gallbladder cancer, gastric cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, skin cancer, small-cell bronchogenic/lung carcinoma, squamous cell carcinoma, sebaceous gland carcinoma, testicular carcinoma, or uterine cancer.

2. A method of inhibiting and/or treating a malignant and/or a benign tumor, fibrosis, cirrhosis, scleroderma or a related dermatologic disease, or a CNS disease comprising: administering an oligonucleotide to a subject in need thereof, wherein one or more nucleotide(s) of the oligonucleotide is/are LNA modified, wherein the modified nucleotide(s) is/are a LNA and/or an ENA, polyalkylene oxide-, 2'-fluoro-, 2'-O-methoxy-, and/or 2'O-methyl-modified nucleotide; and wherein said oligonucleotide is GTCTTGCAGGTGGA (SEQ ID NO. 252; ASPH1106) wherein nucleotides in bold letters are LNA.

3. The method according to claim 2, wherein the tumor is at least one of solid tumors, blood born tumors, leukemia, tumor metastasis, hemangiomas, acoustic neuromas, neurofibromas, trachomas, pyogenic granulomas, psoriasis, astrocytoma, acoustic neuroma, blastoma, Ewing's tumor, craniopharyngloma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, or wherein the malignant and/or a benign tumor, fibrosis, cirrhosis, scleroderma or related dermatologic disease, or CNS disease is at least one of bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, or uterine cancer.

4. A method of inhibiting and/or treating tumor, fibrosis, cirrhosis, scleroderma or a related dermatologic disease, or a CNS disease comprising: administering an oligonucleotide to a subject in need thereof, wherein one or more nucleotide(s) of the oligonucleotide is/are LNA modified, wherein the modified nucleotide(s) is/are a LNA and/or an ENA, polyalkylene oxide, 2'-fluoro-, 2'-O-methoxy-, and/or 2'O-methyl-modified nucleotide; and wherein said oligonucleotide is GTCTTGCAGGTGGA (SEQ ID NO. 252) wherein nucleotides in bold letters are LNA.

5. A method of inhibiting and/or treating a malignant and/or a benign tumor, fibrosis, cirrhosis, scleroderma or a related dermatologic disease, or a CNS disease comprising: administering an oligonucleotide to a subject in need thereof, wherein one or more nucleotide(s) of the oligonucleotide is/are modified, wherein the modified nucleotide(s) is/are a LNA and/or an ENA, polyalkylene oxide-, 2'-fluoro-, 2'-O-methoxy-, and/or 2'O-methyl-modified nucleotide; and wherein said oligonucleotide is GTCT-TGCAGGTGGA (SEQ ID NO. 252; ASPH1106) wherein nucleotides in bold letters are LNA.

* * * * *

SEQUENCE LISTING

```
<160> NUMBER OF SEQ ID NOS: 402

<210> SEQ ID NO 1
<211> LENGTH: 5882
<212> TYPE: DNA
<213> ORGANISM: Homo sapiens

<400> SEQUENCE: 1

gtgatgttat ctgctggcag cagaaggttc gctccgagcg gagctccaga agctcctgac      60

aagagaaaga cagattgaga tagagataga aagagaaaga gagaaagaga cagcagagcg     120

agagcgcaag tgaaagaggc aggggagggg gatggagaat attagcctga cggtctaggg     180

agtcatccag gaacaaactg aggggctgcc cggctgcaga caggaggaga cagagaggat     240

ctattttagg gtggcaagtg cctacctacc ctaagcgagc aattccacgt tggggagaag     300

ccagcagagg ttgggaaagg gtgggagtcc aagggagccc ctgcgcaacc ccctcaggaa     360

taaaactccc cagccagggt gtcgcaaggg ctgccgttgt gatccgcagg gggtgaacgc     420
```

-continued

```
aaccgcgacg gctgatcgtc tgtggctggg ttggcgtttg gagcaagaga aggaggagca    480
ggagaaggag ggagctggag gctggaagcg tttgcaagcg gcggcggcag caacgtggag    540
taaccaagcg ggtcagcgcg cgcccgccag ggtgtaggcc acggagcgca gctcccagag    600
caggatccgc gccgcctcag cagcctctgc ggcccctgcg gcacccgacc gagtaccgag    660
cgccctgcga agcgcaccct cctccccgcg gtgcgctggg ctcgccccca gcgcgcgcac    720
acgcacacac acacacacac acacacacgc acgcacacac gtgtgcgctt ctctgctccg    780
gagctgctgc tgctcctgct ctcagcgccg cagtggaagg caggaccgaa ccgctccttc    840
tttaaatata taaatttcag cccaggtcag cctcggcggc ccccctcacc gcgctcccgg    900
cgcccctccc gtcagttcgc cagctgccag ccccgggacc ttttcatctc ttccctttg     960
gccggaggag ccgagttcag atccgccact ccgcacccga gactgacaca ctgaactcca   1020
cttcctcctc ttaaatttat ttctacttaa tagccactcg tctcttttt tccccatctc   1080
attgctccaa gaattttttt cttcttactc gccaaagtca gggttccctc tgcccgtccc   1140
gtattaatat ttccactttt ggaactactg gccttttctt tttaaaggaa ttcaagcagg   1200
atacgttttt ctgttgggca ttgactagat tgtttgcaaa agtttcgcat caaaaacaac   1260
aacaacaaaa aaccaaacaa ctctccttga tctatacttt gagaattgtt gatttctttt   1320
ttttattctg acttttaaaa acaacttttt tttccacttt tttaaaaaat gcactactgt   1380
gtgctgagcg cttttctgat cctgcatctg gtcacggtcg cgctcagcct gtctacctgc   1440
agcacactcg atatggacca gttcatgcgc aagaggatcg aggcgatccg cgggcagatc   1500
ctgagcaagc tgaagctcac cagtccccca gaagactatc ctgagcccga ggaagtcccc   1560
ccggaggtga tttccatcta caacagcacc agggacttgc tccaggagaa ggcgagccgg   1620
agggcggccg cctgcgagcg cgagaggagc gacgaagagt actacgccaa ggaggtttac   1680
aaaatagaca tgccgccctt cttcccctcc gaaaatgcca tcccgcccac tttctacaga   1740
ccctacttca gaattgttcg atttgacgtc tcagcaatgg agaagaatgc ttccaatttg   1800
gtgaaagcag agttcagagt ctttcgtttg cagaacccaa aagccagagt gcctgaacaa   1860
cggattgagc tatatcagat tctcaagtcc aaagatttaa catctccaac ccagcgctac   1920
atcgacagca aagttgtgaa aacaagagca gaaggcgaat ggctctcctt cgatgtaact   1980
gatgctgttc atgaatggct tcaccataaa gacaggaacc tgggatttaa aataagctta   2040
cactgtccct gctgcacttt tgtaccatct aataattaca tcatcccaaa taaaagtgaa   2100
gaactagaag caagatttgc aggtattgat ggcacctcca catataccag tggtgatcag   2160
aaaactataa agtccactag gaaaaaaaac agtgggaaga ccccacatct cctgctaatg   2220
ttattgccct cctacagact tgagtcacaa cagaccaacc ggcggaagaa gcgtgctttg   2280
gatgcggcct attgctttag aaatgtgcag gataattgct gcctacgtcc actttacatt   2340
gatttcaaga gggatctagg gtggaaatgg atacacgaac ccaaagggta caatgccaac   2400
ttctgtgctg gagcatgccc gtatttatgg agttcagaca ctcagcacag cagggtcctg   2460
agcttatata ataccataaa tccagaagca tctgcttctc cttgctgcgt gtcccaagat   2520
ttagaacctc taaccattct ctactacatt ggcaaaacac ccaagattga acagctttct   2580
aatatgattg taaagtcttg caaatgcagc taaaattctt ggaaaagtgg caagaccaaa   2640
atgacaatga tgatgataat gatgatgacg acgacaacga tgatgcttgt aacaagaaaa   2700
cataagagag ccttggttca tcagtgttaa aaaatttttg aaaaggcggt actagttcag   2760
```

-continued

```
acactttgga agtttgtgtt ctgtttgtta aaactggcat ctgacacaaa aaaagttgaa   2820
ggccttattc tacatttcac ctactttgta agtgagagag acaagaagca aatttttttt   2880
aaagaaaaaa ataaacactg gaagaattta ttagtgttaa ttatgtgaac aacgacaaca   2940
acaacaacaa caacaaacag gaaaatccca ttaagtggag ttgctgtacg taccgttcct   3000
atcccgcgcc tcacttgatt tttctgtatt gctatgcaat aggcaccctt cccattctta   3060
ctcttagagt taacagtgag ttatttattg tgtgttacta tataatgaac gtttcattgc   3120
ccttggaaaa taaaacaggt gtataaagtg gagaccaaat actttgccag aaactcatgg   3180
atggcttaag gaacttgaac tcaaacgagc cagaaaaaaa gaggtcatat taatgggatg   3240
aaaacccaag tgagttatta tatgaccgag aaagtctgca ttaagataaa gaccctgaaa   3300
acacatgtta tgtatcagct gcctaaggaa gcttcttgta aggtccaaaa actaaaaaga   3360
ctgttaataa aagaaacttt cagtcagaat aagtctgtaa gttttttttt ttctttttaa   3420
ttgtaaatgg ttctttgtca gtttagtaaa ccagtgaaat gttgaaatgt tttgacatgt   3480
actggtcaaa cttcagacct taaaatattg ctgtatagct atgctatagg tttttttcctt   3540
tgttttggta tatgtaacca tacctatatt attaaaatag atggatatag aagccagcat   3600
aattgaaaac acatctgcag atctcttttg caaactatta aatcaaaaca ttaactactt   3660
tatgtgtaat gtgtaaattt ttaccatatt ttttatattc tgtaataatg tcaactatga   3720
tttagattga cttaaatttg ggctcttttt aatgatcact cacaaatgta tgtttctttt   3780
agctggccag tacttttgag taaagcccct atagtttgac ttgcactaca aatgcatttt   3840
tttttaata acatttgccc tacttgtgct ttgtgtttct ttcattatta tgacataagc   3900
tacctgggtc cacttgtctt ttcttttttt tgtttcacag aaaagatggg ttcgagttca   3960
gtggtcttca tcttccaagc atcattacta accaagtcag acgttaacaa atttttatgt   4020
taggaaaagg aggaatgtta tagatacata gaaaattgaa gtaaaatgtt ttcattttag   4080
caaggattta gggttctaac taaaactcag aatctttatt gagttaagaa aagtttctct   4140
accttggttt aatcaatatt tttgtaaaat cctattgtta ttacaaagag gacacttcat   4200
aggaaacatc tttttcttta gtcaggtttt taatattcag ggggaaattg aaagatatat   4260
attttagtcg atttttcaaa aggggaaaaa agtccaggtc agcataagtc attttgtgta   4320
tttcactgaa gttataaggt ttttataaat gttctttgaa ggggaaaagg cacaagccaa   4380
tttttcctat gatcaaaaaa ttctttcttt cctctgagtg agagttatct atatctgagg   4440
ctaaagttta ccttgcttta ataaataatt tgccacatca ttgcagaaga ggtatcctca   4500
tgctggggtt aatagaatat gtcagtttat cacttgtcgc ttatttagct ttaaaataaa   4560
aattaatagg caaagcaatg gaatatttgc agtttcacct aaagagcagc ataaggaggc   4620
gggaatccaa agtgaagttg tttgatatgg tctacttctt ttttggaatt tcctgaccat   4680
taattaaaga attggatttg caagtttgaa aactggaaaa gcaagagatg ggatgccata   4740
atagtaaaca gcccttgtgt tggatgtaac ccaatcccag atttgagtgt gtgttgatta   4800
ttttttgtc ttccactttt ctattatgtg taaatcactt ttatttctgc agacattttc   4860
ctctcagata ggatgacatt ttgttttgta ttattttgtc tttcctcatg aatgcactga   4920
taatatttta aatgctctat tttaagatct cttgaatctg tttttttttt ttttaatttg   4980
ggggttctgt aaggtcttta tttcccataa gtaaatattg ccatgggagg ggggtggagg   5040
tggcaaggaa ggggtgaagt gctagtatgc aagtgggcag caattatttt tgtgttaatc   5100
agcagtacaa tttgatcgtt ggcatggtta aaaaatggaa tataagatta gctgttttgt   5160
```

-continued

```
attttgatga ccaattacgc tgtattttaa cacgatgtat gtctgttttt gtggtgctct   5220

agtggtaaat aaattatttc gatgatatgt ggatgtcttt ttcctatcag taccatcatc   5280

gagtctagaa aacacctgtg atgcaataag actatctcaa gctggaaaag tcataccacc   5340

tttccgattg ccctctgtgc tttctccctt aaggacagtc acttcagaag tcatgcttta   5400

aagcacaaga gtcaggccat atccatcaag gatagaagaa atccctgtgc cgtcttttta   5460

ttcccttatt tattgctatt tggtaattgt ttgagattta gtttccatcc agcttgactg   5520

ccgaccagaa aaaatgcaga gagatgtttg caccatgctt tggctttctg gttctatgtt   5580

ctgccaacgc cagggccaaa agaactggtc tagacagtat cccctgtagc cccataactt   5640

ggatagttgc tgagccagcc agatataaca agagccacgt gctttctggg gttggttgtt   5700

tgggatcagc tacttgcctg tcagtttcac tggtaccact gcaccacaaa caaaaaaacc   5760

caccctattt cctccaattt ttttggctgc tacctacaag accagactcc tcaaacgagt   5820

tgccaatctc ttaataaata ggattaataa aaaaagtaat tgtgactcaa aaaaaaaaaa   5880

aa                                                                  5882


<210> SEQ ID NO 2
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 2

gaccagatgc agga                                                       14


<210> SEQ ID NO 3
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 3

gcgaccgtga ccagat                                                     16


<210> SEQ ID NO 4
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 4

gcgcgaccgt gacc                                                       14


<210> SEQ ID NO 5
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 5

agcgcgaccg tga                                                        13


<210> SEQ ID NO 6
<211> LENGTH: 14
<212> TYPE: DNA
```

<213> ORGANISM: Artificial Sequence
<220> FEATURE:
<223> OTHER INFORMATION: modified TGF-beta2 oligonucleotide

<400> SEQUENCE: 6
gaccgtgacc agat 14

<210> SEQ ID NO 7
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 7
ctgcccgcgg at 12

<210> SEQ ID NO 8
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 8
tctgcccgcg gat 13

<210> SEQ ID NO 9
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 9
ggatctgccc gcgga 15

<210> SEQ ID NO 10
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 10
cttgctcagg atctgcc 17

<210> SEQ ID NO 11
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 11
gctcaggatc tgcccgcgga 20

<210> SEQ ID NO 12
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 12
ggatcgcctc gat 13

<210> SEQ ID NO 13
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 13
ccgcggatcg cc 12

<210> SEQ ID NO 14
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 14
acctccttgg cgtagta 17

<210> SEQ ID NO 15
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 15
cctccttggc gtagta 16

<210> SEQ ID NO 16
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 16
ctccttggcg tagta 15

<210> SEQ ID NO 17
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 17
tccttggcgt agta 14

<210> SEQ ID NO 18
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 18
cagaagttgg cat 13

<210> SEQ ID NO 19
<211> LENGTH: 13
<212> TYPE: DNA
<213> ORGANISM: Artificial Sequence
<220> FEATURE:

-continued

<223> OTHER INFORMATION: modified TGF-beta2 oligonucleotide

<400> SEQUENCE: 19
aagtgggcgg gat 13

<210> SEQ ID NO 20
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 20
gcgggatggc at 12

<210> SEQ ID NO 21
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 21
gaaatcacct ccg 13

<210> SEQ ID NO 22
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 22
aagtgggcgg gat 13

<210> SEQ ID NO 23
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 23
tgtagcgctg ggt 13

<210> SEQ ID NO 24
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 24
cgaaggagag cca 13

<210> SEQ ID NO 25
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 25
tcgcgctcgc aggc 14

<210> SEQ ID NO 26
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 26
aagtgggcgg gatg 14

<210> SEQ ID NO 27
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 27
atgtagcgct gggt 14

<210> SEQ ID NO 28
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 28
cgaaggagag ccat 14

<210> SEQ ID NO 29
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 29
gaaagtgggc gggat 15

<210> SEQ ID NO 30
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 30
cgaaggagag ccatt 15

<210> SEQ ID NO 31
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 31
cgatcctctt gcgcat 16

<210> SEQ ID NO 32
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 32
aagtgggcgg gatggc 16

<210> SEQ ID NO 33
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 33
gatggaaatc acctccg 17

<210> SEQ ID NO 34
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 34
aaacctcctt ggcgtag 17

<210> SEQ ID NO 35
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 35
tagaaagtgg gcgggat 17

<210> SEQ ID NO 36
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 36
ggcgggatgg cat 13

<210> SEQ ID NO 37
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 37
gggtctgtag aaagtg 16

<210> SEQ ID NO 38
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 38
gaaggagagc cattc 15

<210> SEQ ID NO 39
<211> LENGTH: 15

```
<212> TYPE: DNA
<213> ORGANISM: Artificial Sequence
<220> FEATURE:
<223> OTHER INFORMATION: modified TGF-beta2 oligonucleotide

<400> SEQUENCE: 39

ccaggttcct gtctt                                                    15


<210> SEQ ID NO 40
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 40

tctgatcacc actgg                                                    15


<210> SEQ ID NO 41
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 41

tttctgatca ccactgg                                                  17


<210> SEQ ID NO 42
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 42

gtctgtagga gggca                                                    15


<210> SEQ ID NO 43
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 43

agtctgtagg agggca                                                   16


<210> SEQ ID NO 44
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 44

tctgtaggag ggc                                                      13


<210> SEQ ID NO 45
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 45
```

cagatgccag ttttaac 17

<210> SEQ ID NO 46
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 46
caaagtattt ggtctcc 17

<210> SEQ ID NO 47
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 47
ccttaagcca tccatga 17

<210> SEQ ID NO 48
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 48
gtactggcca gctaa 15

<210> SEQ ID NO 49
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 49
gcctcgatcc tcttgcgcat 20

<210> SEQ ID NO 50
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 50
aaacctcctt ggcgtagtac 20

<210> SEQ ID NO 51
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 51
gaaagtgggc gggatggcat 20

<210> SEQ ID NO 52
<211> LENGTH: 17
<212> TYPE: DNA
<213> ORGANISM: Artificial Sequence -continued
<220> FEATURE:
<223> OTHER INFORMATION: modified TGF-beta2 oligonucleotide

<400> SEQUENCE: 52
gaattgctcg cttaggg 17

<210> SEQ ID NO 53
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 53
cgtcgcggtt gcgttca 17

<210> SEQ ID NO 54
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 54
cgtggcctac accctgg 17

<210> SEQ ID NO 55
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 55
ttctaaagca ataggcc 17

<210> SEQ ID NO 56
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 56
agaatggtta gaggttc 17

<210> SEQ ID NO 57
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 57
tctgaactag taccgcc 17

<210> SEQ ID NO 58
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 58
cccattaata tgacctc 17

<210> SEQ ID NO 59
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 59
tttagttaga accctaa 17

<210> SEQ ID NO 60
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 60
cctcagatat agataac 17

<210> SEQ ID NO 61
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 61
tactattatg gcatccc 17

<210> SEQ ID NO 62
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 62
tgcccacttg catacta 17

<210> SEQ ID NO 63
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 63
agcgtaattg gtcatca 17

<210> SEQ ID NO 64
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 64
cgttggcaga acataga 17

<210> SEQ ID NO 65
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 65
gggatactgt ctagacc 17

<210> SEQ ID NO 66
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 66
attggcaact cgtttga 17

<210> SEQ ID NO 67
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 67
cgtcaggcta atattc 16

<210> SEQ ID NO 68
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 68
ggatgactcc ctagac 16

<210> SEQ ID NO 69
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 69
gtcgcggttg cgttca 16

<210> SEQ ID NO 70
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 70
ctcggtactc ggtcgg 16

<210> SEQ ID NO 71
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 71
ggttcggtcc tgcctt 16

<210> SEQ ID NO 72

-continued

<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 72
aataggccgc atccaa 16

<210> SEQ ID NO 73
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 73
aactagtacc gccttt 16

<210> SEQ ID NO 74
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 74
tcggtcatat aataac 16

<210> SEQ ID NO 75
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 75
agaccgtcag gctaa 15

<210> SEQ ID NO 76
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 76
gtcgcggttg cgttc 15

<210> SEQ ID NO 77
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 77
ttccactgcg gcgct 15

<210> SEQ ID NO 78
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 78
aaggagcggt tcggt 15

<210> SEQ ID NO 79
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 79
ctcgggtgcg gagtg 15

<210> SEQ ID NO 80
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 80
ctgactttgg cgagt 15

<210> SEQ ID NO 81
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 81
gataggaacg gtacg 15

<210> SEQ ID NO 82
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 82
cactttggat tcccg 15

<210> SEQ ID NO 83
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 83
gtcgcggttg cgtt 14

<210> SEQ ID NO 84
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 84
tacaccctgg cggg 14

<210> SEQ ID NO 85
<211> LENGTH: 14
<212> TYPE: DNA

-continued

<213> ORGANISM: Artificial Sequence
<220> FEATURE:
<223> OTHER INFORMATION: modified TGF-beta2 oligonucleotide

<400> SEQUENCE: 85
ctcggtactc ggtc 14

<210> SEQ ID NO 86
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 86
aggagcggtt cggt 14

<210> SEQ ID NO 87
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 87
gtctcgggtg cgga 14

<210> SEQ ID NO 88
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 88
tacgggacgg gcag 14

<210> SEQ ID NO 89
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 89
cgtcgctcct ctcg 14

<210> SEQ ID NO 90
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 90
tagcgctggg ttgg 14

<210> SEQ ID NO 91
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 91
aagcaatagg ccgc 14

<210> SEQ ID NO 92
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 92
tacgggcatg ctcc 14

<210> SEQ ID NO 93
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 93
aggcgcggga tagg 14

<210> SEQ ID NO 94
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 94
tttggattcc cgcc 14

<210> SEQ ID NO 95
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 95
accactagag cacc 14

<210> SEQ ID NO 96
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 96
gcgttggcag aaca 14

<210> SEQ ID NO 97
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 97
ttgctcgctt agg 13

<210> SEQ ID NO 98
<211> LENGTH: 13
<212> TYPE: DNA
<213> ORGANISM: Artificial Sequence
<220> FEATURE:

<223> OTHER INFORMATION: modified TGF-beta2 oligonucleotide

<400> SEQUENCE: 98
gtcgcggttg cgt 13

<210> SEQ ID NO 99
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 99
ggcgctcggt act 13

<210> SEQ ID NO 100
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 100
atctgaactc ggc 13

<210> SEQ ID NO 101
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 101
cggttggtct gtt 13

<210> SEQ ID NO 102
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 102
tccaccctag atc 13

<210> SEQ ID NO 103
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 103
ctagtaccgc ctt 13

<210> SEQ ID NO 104
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 104
ggtcggcagt caa 13

<210> SEQ ID NO 105
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 105
cttgcgacac cc 12

<210> SEQ ID NO 106
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 106
gagcggttcg gt 12

<210> SEQ ID NO 107
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 107
acacagtagt gcat 14

<210> SEQ ID NO 108
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 108
gggtctgtag aaag 14

<210> SEQ ID NO 109
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 109
ggttggagat gtta 14

<210> SEQ ID NO 110
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 110
tgggttggag atgt 14

<210> SEQ ID NO 111
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 111
gctgggttgg agat 14

<210> SEQ ID NO 112
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 112
gcgctgggtt ggag 14

<210> SEQ ID NO 113
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 113
agcgctgggt tgga 14

<210> SEQ ID NO 114
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 114
tagcgctggg ttgg 14

<210> SEQ ID NO 115
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 115
gtagcgctgg gttg 14

<210> SEQ ID NO 116
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 116
gatgtagcgc tggg 14

<210> SEQ ID NO 117
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 117
ccattcgcct tctg 14

<210> SEQ ID NO 118
<211> LENGTH: 14

<212> TYPE: DNA
<213> ORGANISM: Artificial Sequence
<220> FEATURE:
<223> OTHER INFORMATION: modified TGF-beta2 oligonucleotide

<400> SEQUENCE: 118
gagagccatt cgcc 14

<210> SEQ ID NO 119
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 119
agcagggaca gtgt 14

<210> SEQ ID NO 120
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 120
gcaggagatg tggg 14

<210> SEQ ID NO 121
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 121
cggttggtct gttg 14

<210> SEQ ID NO 122
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 122
ccggttggtc tgtt 14

<210> SEQ ID NO 123
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 123
gccggttggt ctgt 14

<210> SEQ ID NO 124
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 124
agttggcatt gtac 14

<210> SEQ ID NO 125
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 125
ggttagaggt tcta 14

<210> SEQ ID NO 126
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 126
atggttagag gttc 14

<210> SEQ ID NO 127
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 127
agaatggtta gagg 14

<210> SEQ ID NO 128
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 128
agagaatggt taga 14

<210> SEQ ID NO 129
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 129
cgttgtcgtc gtca 14

<210> SEQ ID NO 130
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 130
accaaggctc tctt 14

<210> SEQ ID NO 131
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 131
gcttcttgtc tctc 14

<210> SEQ ID NO 132
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 132
ggaacggtac gtac 14

<210> SEQ ID NO 133
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 133
taggaacggt acgt 14

<210> SEQ ID NO 134
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 134
gggataggaa cggt 14

<210> SEQ ID NO 135
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 135
cgcgggatag gaac 14

<210> SEQ ID NO 136
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 136
aggcgcggga tagg 14

<210> SEQ ID NO 137
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 137
gtcaagctgg atgg 14

<210> SEQ ID NO 138
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 138
tctgtaggag ggc 13

<210> SEQ ID NO 139
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 139
gaccagatgc agga 14

<210> SEQ ID NO 140
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 140
ctccttggcg tagta 15

<210> SEQ ID NO 141
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 141
cctccttggc gtagta 16

<210> SEQ ID NO 142
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 142
cagatgccag ttttaac 17

<210> SEQ ID NO 143
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 143
agcgtaattg gtcatca 17

<210> SEQ ID NO 144
<211> LENGTH: 17
<212> TYPE: DNA
<213> ORGANISM: Artificial Sequence
<220> FEATURE:
<223> OTHER INFORMATION: fake sequence

<400> SEQUENCE: 144
aaaaaaaaaa aaaaaaa 17

<210> SEQ ID NO 145
<211> LENGTH: 18
<212> TYPE: DNA
<213> ORGANISM: Artificial Sequence
<220> FEATURE:
<223> OTHER INFORMATION: fake sequence

<400> SEQUENCE: 145
aaaaaaaaaa aaaaaaaa 18

<210> SEQ ID NO 146
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 146
agtatttggt ctcc 14

<210> SEQ ID NO 147
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 147
aagtatttgg tctc 14

<210> SEQ ID NO 148
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 148
caaagtattt ggtctcc 17

<210> SEQ ID NO 149
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 149
aagtatttgg tctcc 15

<210> SEQ ID NO 150
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 150
agctcgtccc tcctccc 17

<210> SEQ ID NO 151

<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 151
gagggctggt ccggaat 17

<210> SEQ ID NO 152
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 152
cgagggctgg tccggaa 17

<210> SEQ ID NO 153
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 153
gagggcggca tggggga 17

<210> SEQ ID NO 154
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 154
gcgggtgctg ttgtaca 17

<210> SEQ ID NO 155
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 155
cgcgggtgct gttgtac 17

<210> SEQ ID NO 156
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 156
gtcgcgggtg ctgttgt 17

<210> SEQ ID NO 157
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 157
ggtcgcgggt gctgttg 17

<210> SEQ ID NO 158
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 158
ccggtcgcgg gtgctgt 17

<210> SEQ ID NO 159
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 159
cccggtcgcg ggtgctg 17

<210> SEQ ID NO 160
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 160
agcacgcggg tgacctc 17

<210> SEQ ID NO 161
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 161
ttagcacgcg ggtgacc 17

<210> SEQ ID NO 162
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 162
gggctcgtgg atccact 17

<210> SEQ ID NO 163
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 163
ccttgggctc gtggatc 17

<210> SEQ ID NO 164
<211> LENGTH: 17
<212> TYPE: DNA

<213> ORGANISM: Artificial Sequence
<220> FEATURE:
<223> OTHER INFORMATION: modified TGF-beta1 oligonucleotide

<400> SEQUENCE: 164
tggcatggta gcccttg 17

<210> SEQ ID NO 165
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 165
cgagggctgg tccgga 16

<210> SEQ ID NO 166
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 166
gcgggtgctg ttgtac 16

<210> SEQ ID NO 167
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 167
gcacgcgggt gacctc 16

<210> SEQ ID NO 168
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 168
ccttgggctc gtggat 16

<210> SEQ ID NO 169
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 169
ggcatggtag cccttg 16

<210> SEQ ID NO 170
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 170
gggtgctgtt gtac 14

-continued

<210> SEQ ID NO 171
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 171
tcgcgggtgc tgtt 14

<210> SEQ ID NO 172
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 172
gtcgcgggtg ctgt 14

<210> SEQ ID NO 173
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 173
ctcgtggatc cact 14

<210> SEQ ID NO 174
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 174
atggtagccc ttgg 14

<210> SEQ ID NO 175
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 175
tggcatggta gccc 14

<210> SEQ ID NO 176
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 176
gaagttggca tggt 14

<210> SEQ ID NO 177
<211> LENGTH: 13
<212> TYPE: DNA
<213> ORGANISM: Artificial Sequence
<220> FEATURE:

<223> OTHER INFORMATION: modified TGF-beta1 oligonucleotide

<400> SEQUENCE: 177
tcgcgggtgc tgt 13

<210> SEQ ID NO 178
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 178
cacccggtcg cgg 13

<210> SEQ ID NO 179
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 179
ccacccggtc gcg 13

<210> SEQ ID NO 180
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 180
cgccaggaat tgt 13

<210> SEQ ID NO 181
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 181
ggctcgtgga tcc 13

<210> SEQ ID NO 182
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 182
tgggctcgtg gat 13

<210> SEQ ID NO 183
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 183
gcatggtagc cct 13

<210> SEQ ID NO 184
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 184
agttggcatg gta 13

<210> SEQ ID NO 185
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 185
ttgcaggagc gca 13

<210> SEQ ID NO 186
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 186
attagcacgc gggtgac 17

<210> SEQ ID NO 187
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 187
accattagca cgcgggt 17

<210> SEQ ID NO 188
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 188
caccattagc acgcggg 17

<210> SEQ ID NO 189
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 189
ccaccattag cacgcgg 17

<210> SEQ ID NO 190
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 190
tccaccatta gcacgcg 17

<210> SEQ ID NO 191
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 191
tccaccttgg gcttgcg 17

<210> SEQ ID NO 192
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 192
ttagcacgcg ggtgac 16

<210> SEQ ID NO 193
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 193
accattagca cgcggg 16

<210> SEQ ID NO 194
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 194
caccattagc acgcgg 16

<210> SEQ ID NO 195
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 195
caccattagc acgcg 15

<210> SEQ ID NO 196
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 196
gcggcacgca gcacg 15

<210> SEQ ID NO 197
<211> LENGTH: 14

```
<212> TYPE: DNA
<213> ORGANISM: Artificial Sequence
<220> FEATURE:
<223> OTHER INFORMATION: modified TGF-beta1 oligonucleotide

<400> SEQUENCE: 197

tcgatgcgct tccg                                                        14


<210> SEQ ID NO 198
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 198

tagcacgcgg gtga                                                        14


<210> SEQ ID NO 199
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 199

attagcacgc gggt                                                        14


<210> SEQ ID NO 200
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 200

cattagcacg cggg                                                        14


<210> SEQ ID NO 201
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 201

accattagca cgcg                                                        14


<210> SEQ ID NO 202
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 202

caccattagc acgc                                                        14


<210> SEQ ID NO 203
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 203
```

ccaccattag cacg 14

<210> SEQ ID NO 204
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 204
tccaccatta gcac 14

<210> SEQ ID NO 205
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 205
gaccttgctg tact 14

<210> SEQ ID NO 206
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 206
ggaccttgct gtac 14

<210> SEQ ID NO 207
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 207
aggaccttgc tgta 14

<210> SEQ ID NO 208
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 208
cggcacgcag cacg 14

<210> SEQ ID NO 209
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 209
accttgggct tgcg 14

<210> SEQ ID NO 210
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 210
ttagcacgcg ggt 13

<210> SEQ ID NO 211
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 211
accattagca cgc 13

<210> SEQ ID NO 212
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 212
cggcacgcag cac 13

<210> SEQ ID NO 213
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 213
caccagctcc atgtcga 17

<210> SEQ ID NO 214
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 214
tcgcgggtgc tgttgta 17

<210> SEQ ID NO 215
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 215
gtgtccaggc tccaaat 17

<210> SEQ ID NO 216
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 216
gctcgtccct cctccc 16

<210> SEQ ID NO 217
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 217
accagctcgt ccctcc 16

<210> SEQ ID NO 218
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 218
ggaggccccg cccctg 16

<210> SEQ ID NO 219
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 219
catgggggag gcggcg 16

<210> SEQ ID NO 220
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 220
accagctcca tgtcga 16

<210> SEQ ID NO 221
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 221
ggtcgcgggt gctgtt 16

<210> SEQ ID NO 222
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 222
ggaccttgct gtactg 16

<210> SEQ ID NO 223
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 223
tccaccttgg gcttgc 16

<210> SEQ ID NO 224
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 224
agctcgtccc tcctc 15

<210> SEQ ID NO 225
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 225
ccagctcgtc cctcc 15

<210> SEQ ID NO 226
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 226
gagggctggt ccgga 15

<210> SEQ ID NO 227
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 227
tcccgagggc tggtc 15

<210> SEQ ID NO 228
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 228
cggcatgggg gaggc 15

<210> SEQ ID NO 229
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 229
cagctccatg tcgat 15

<210> SEQ ID NO 230

<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 230
accagctcca tgtcg 15

<210> SEQ ID NO 231
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 231
tcgcgggtgc tgttg 15

<210> SEQ ID NO 232
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 232
gtcgcgggtg ctgtt 15

<210> SEQ ID NO 233
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 233
ggtcgcgggt gctgt 15

<210> SEQ ID NO 234
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 234
agcacgcggg tgacc 15

<210> SEQ ID NO 235
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 235
tagcacgcgg gtgac 15

<210> SEQ ID NO 236
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 236
cattagcacg cgggt 15

<210> SEQ ID NO 237
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 237
tccaccatta gcacg 15

<210> SEQ ID NO 238
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 238
ccaggaattg ttgct 15

<210> SEQ ID NO 239
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 239
ttgggctcgt ggatc 15

<210> SEQ ID NO 240
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 240
cttgggctcg tggat 15

<210> SEQ ID NO 241
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 241
ttggcatggt agccc 15

<210> SEQ ID NO 242
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 242
gaagttggca tggta 15

<210> SEQ ID NO 243
<211> LENGTH: 15
<212> TYPE: DNA

<213> ORGANISM: Artificial Sequence
<220> FEATURE:
<223> OTHER INFORMATION: modified TGF-beta1 oligonucleotide

<400> SEQUENCE: 243
agaagttggc atggt 15

<210> SEQ ID NO 244
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 244
tgtccaggct ccaaa 15

<210> SEQ ID NO 245
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 245
aggaccttgc tgtac 15

<210> SEQ ID NO 246
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 246
caccttgggc ttgcg 15

<210> SEQ ID NO 247
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 247
agctcgtccc tcct 14

<210> SEQ ID NO 248
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 248
cagctcgtcc ctcc 14

<210> SEQ ID NO 249
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 249
accagctcgt ccct 14

<210> SEQ ID NO 250
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 250
cccgagggct ggtc 14

<210> SEQ ID NO 251
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 251
gcggcatggg ggag 14

<210> SEQ ID NO 252
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 252
gtcttgcagg tgga 14

<210> SEQ ID NO 253
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 253
tcgatgcgct tccg 14

<210> SEQ ID NO 254
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 254
ggacaggatc tggc 14

<210> SEQ ID NO 255
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 255
acctccccct ggct 14

<210> SEQ ID NO 256
<211> LENGTH: 14
<212> TYPE: DNA
<213> ORGANISM: Artificial Sequence
<220> FEATURE:

<223> OTHER INFORMATION: modified TGF-beta1 oligonucleotide

<400> SEQUENCE: 256
accattagca cgcg 14

<210> SEQ ID NO 257
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 257
cagcagttct tctc 14

<210> SEQ ID NO 258
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 258
tacagctgcc gcac 14

<210> SEQ ID NO 259
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 259
agttggcatg gtag 14

<210> SEQ ID NO 260
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 260
aagttggcat ggta 14

<210> SEQ ID NO 261
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 261
gaagttggca tggt 14

<210> SEQ ID NO 262
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 262
tccaggctcc aaat 14

-continued

<210> SEQ ID NO 263
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 263
accttgctgt actg 14

<210> SEQ ID NO 264
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 264
ttgcaggagc gcac 14

<210> SEQ ID NO 265
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 265
gcagaagttg gcat 14

<210> SEQ ID NO 266
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 266
cgggtgctgt tgta 14

<210> SEQ ID NO 267
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 267
cccagcggca acggaaa 17

<210> SEQ ID NO 268
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 268
caagaggtcc ccgcgcc 17

<210> SEQ ID NO 269
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 269
gcgtccccgg cggcaaa 17

<210> SEQ ID NO 270
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 270
ggtcggcgac tcccgag 17

<210> SEQ ID NO 271
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 271
tcggagagag atccgtc 17

<210> SEQ ID NO 272
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 272
atcccacgga aataacc 17

<210> SEQ ID NO 273
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 273
ctcagtatcc cacggaa 17

<210> SEQ ID NO 274
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 274
actgccgaga gcgcgaa 17

<210> SEQ ID NO 275
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 275
ctgatgtgtt gaagaac 17

<210> SEQ ID NO 276
<211> LENGTH: 17

<212> TYPE: DNA
<213> ORGANISM: Artificial Sequence
<220> FEATURE:
<223> OTHER INFORMATION: modified TGF-beta oligonucleotide

<400> SEQUENCE: 276
tgaggtatcg ccaggaa 17

<210> SEQ ID NO 277
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 277
actgccgcac aactccg 17

<210> SEQ ID NO 278
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 278
cggcccacgt agtacac 17

<210> SEQ ID NO 279
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 279
cccagcggca acggaa 16

<210> SEQ ID NO 280
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 280
tcgcgccaag aggtcc 16

<210> SEQ ID NO 281
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 281
ggtcggcgac tcccga 16

<210> SEQ ID NO 282
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 282
gtcggagaga gatccg 16

<210> SEQ ID NO 283
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 283
tcagtatccc acggaa 16

<210> SEQ ID NO 284
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 284
cgagagcgcg aacagg 16

<210> SEQ ID NO 285
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 285
actgccgaga gcgcga 16

<210> SEQ ID NO 286
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 286
ggcgtcagca ccagta 16

<210> SEQ ID NO 287
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 287
ggtttccacc attagc 16

<210> SEQ ID NO 288
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 288
gaggtatcgc caggaa 16

<210> SEQ ID NO 289
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 289
aaccactgcc gcacaa 16

<210> SEQ ID NO 290
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 290
cggcccacgt agtaca 16

<210> SEQ ID NO 291
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 291
cggcggctcg tctca 15

<210> SEQ ID NO 292
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 292
cccagcggca acgga 15

<210> SEQ ID NO 293
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 293
tcgcgccaag aggtc 15

<210> SEQ ID NO 294
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 294
cgtcgcgcca agagg 15

<210> SEQ ID NO 295
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 295
ggagcaagcg tcccc 15

<210> SEQ ID NO 296
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 296
gtgcgcccga ggtct 15

<210> SEQ ID NO 297
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 297
gtctaggatg cgcgg 15

<210> SEQ ID NO 298
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 298
cagtatccca cggaa 15

<210> SEQ ID NO 299
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 299
ccgagagcgc gaaca 15

<210> SEQ ID NO 300
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 300
ggcgtcagca ccagt 15

<210> SEQ ID NO 301
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 301
gttgctgagg tatcg 15

<210> SEQ ID NO 302
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 302
accactgccg cacaa 15

<210> SEQ ID NO 303
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 303
cggcccacgt agtac 15

<210> SEQ ID NO 304
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 304
ctcggcgact cctt 14

<210> SEQ ID NO 305
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 305
agcggcaacg gaaa 14

<210> SEQ ID NO 306
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 306
tcgcgccaag aggt 14

<210> SEQ ID NO 307
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 307
tccccggcgg caaa 14

<210> SEQ ID NO 308
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 308
tgcgcccgag gtct 14

<210> SEQ ID NO 309

<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 309
gtctaggatg cgcg 14

<210> SEQ ID NO 310
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 310
ggtcggagag agat 14

<210> SEQ ID NO 311
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 311
cacggaaata acct 14

<210> SEQ ID NO 312
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 312
agagcgcgaa cagg 14

<210> SEQ ID NO 313
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 313
atagtcccgc ggcc 14

<210> SEQ ID NO 314
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 314
tagtagtcgg cctc 14

<210> SEQ ID NO 315
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 315
atagatttcg ttgt 14

<210> SEQ ID NO 316
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 316
gaggtatcgc cagg 14

<210> SEQ ID NO 317
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 317
gccgcacaac tccg 14

<210> SEQ ID NO 318
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 318
tcgcgccaag agg 13

<210> SEQ ID NO 319
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 319
aagcgtcccc ggc 13

<210> SEQ ID NO 320
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 320
gacgccgtgt agg 13

<210> SEQ ID NO 321
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 321
gtcggcgact ccc 13

<210> SEQ ID NO 322
<211> LENGTH: 13
<212> TYPE: DNA

<213> ORGANISM: Artificial Sequence
<220> FEATURE:
<223> OTHER INFORMATION: modified TGF-beta oligonucleotide

<400> SEQUENCE: 322
tgcgcccgag gtc 13

<210> SEQ ID NO 323
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 323
gtcggagaga gat 13

<210> SEQ ID NO 324
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 324
tcccacggaa ata 13

<210> SEQ ID NO 325
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 325
tgccgagagc gcg 13

<210> SEQ ID NO 326
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 326
tagtcccgcg gcc 13

<210> SEQ ID NO 327
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 327
tagtagtcgg cct 13

<210> SEQ ID NO 328
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 328
catagatttc gtt 13

<210> SEQ ID NO 329
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 329
tttaacttga gcc 13

<210> SEQ ID NO 330
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 330
gaggtatcgc cag 13

<210> SEQ ID NO 331
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 331
actccggtga cat 13

<210> SEQ ID NO 332
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 332
gcccacgtag tac 13

<210> SEQ ID NO 333
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 333
tcggcgactc cc 12

<210> SEQ ID NO 334
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 334
gtcggcgact cc 12

<210> SEQ ID NO 335
<211> LENGTH: 14
<212> TYPE: DNA
<213> ORGANISM: Artificial Sequence
<220> FEATURE:

<223> OTHER INFORMATION: fake sequence

<400> SEQUENCE: 335
aaaaaaaaaa aaaa 14

<210> SEQ ID NO 336
<211> LENGTH: 16
<212> TYPE: DNA
<213> ORGANISM: Artificial Sequence
<220> FEATURE:
<223> OTHER INFORMATION: fake sequence

<400> SEQUENCE: 336
aaaaaaaaaa aaaaaa 16

<210> SEQ ID NO 337
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 337
caggaagcgc tggcaac 17

<210> SEQ ID NO 338
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 338
ggtgcatgaa ctcactg 17

<210> SEQ ID NO 339
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 339
gtcccctaat ggcttcc 17

<210> SEQ ID NO 340
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 340
atctgtcccc taatggc 17

<210> SEQ ID NO 341
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 341
ccgggtgctg ttgtaaa 17

<210> SEQ ID NO 342
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 342
cctggatcat gtcgaat 17

<210> SEQ ID NO 343
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 343
ccctggatca tgtcgaa 17

<210> SEQ ID NO 344
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 344
gtagcacctg cttccag 17

<210> SEQ ID NO 345
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 345
gggctttcta aatgac 16

<210> SEQ ID NO 346
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 346
tgactcccag caggcc 16

<210> SEQ ID NO 347
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 347
gtgcatgaac tcactg 16

<210> SEQ ID NO 348
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 348
ggtgcatgaa ctcact 16

<210> SEQ ID NO 349
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 349
atctgtcccc taatgg 16

<210> SEQ ID NO 350
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 350
cgggtgctgt tgtaaa 16

<210> SEQ ID NO 351
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 351
ccgggtgctg ttgtaa 16

<210> SEQ ID NO 352
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 352
cctggatcat gtcgaa 16

<210> SEQ ID NO 353
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 353
ccctggatca tgtcga 16

<210> SEQ ID NO 354
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 354
tttgaatttg atttcc 16

<210> SEQ ID NO 355
<211> LENGTH: 16

<212> TYPE: DNA
<213> ORGANISM: Artificial Sequence
<220> FEATURE:
<223> OTHER INFORMATION: modified TGF-beta3 oligonucleotide

<400> SEQUENCE: 355
gggcctgagc agaagt 16

<210> SEQ ID NO 356
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 356
gggggctttc taaat 15

<210> SEQ ID NO 357
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 357
tttgtttaca cttcc 15

<210> SEQ ID NO 358
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 358
ccagctaaag gtggg 15

<210> SEQ ID NO 359
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 359
atggctgggt cccaa 15

<210> SEQ ID NO 360
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 360
gagtttttcc ttagg 15

<210> SEQ ID NO 361
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 361
aggggtggca aggca 15

<210> SEQ ID NO 362
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 362
tgactcccag caggc 15

<210> SEQ ID NO 363
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 363
gaagcgctgg caacc 15

<210> SEQ ID NO 364
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 364
gtgcatgaac tcact 15

<210> SEQ ID NO 365
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 365
gtggtgcaag tggac 15

<210> SEQ ID NO 366
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 366
ctaatggctt ccacc 15

<210> SEQ ID NO 367
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 367
cccctaatgg cttcc 15

<210> SEQ ID NO 368
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 368
atctgtcccc taatg 15

<210> SEQ ID NO 369
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 369
gatctgtccc ctaat 15

<210> SEQ ID NO 370
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 370
agatctgtcc cctaa 15

<210> SEQ ID NO 371
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 371
ggtgctgttg taaag 15

<210> SEQ ID NO 372
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 372
ccgggtgctg ttgta 15

<210> SEQ ID NO 373
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 373
gatcatgtcg aattt 15

<210> SEQ ID NO 374
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 374
cctggatcat gtcga 15

<210> SEQ ID NO 375
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 375
ccctggatca tgtcg 15

<210> SEQ ID NO 376
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 376
gatttccatc acctc 15

<210> SEQ ID NO 377
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 377
ttgaatttga tttcc 15

<210> SEQ ID NO 378
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 378
agcagttctc ctcca 15

<210> SEQ ID NO 379
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 379
gcctgagcag aagtt 15

<210> SEQ ID NO 380
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 380
gggcaagggc ctgag 15

<210> SEQ ID NO 381
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 381
cccacacttt cttta 15

<210> SEQ ID NO 382
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 382
tagcacctgc ttcca 15

<210> SEQ ID NO 383
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 383
cgggggcttt ctaa 14

<210> SEQ ID NO 384
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 384
ccattcatgc tttc 14

<210> SEQ ID NO 385
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 385
aagcgctggc aacc 14

<210> SEQ ID NO 386
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 386
accagagccc tttg 14

<210> SEQ ID NO 387
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 387
cccctaatgg cttc 14

<210> SEQ ID NO 388

<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 388
gtcccctaat ggct 14

<210> SEQ ID NO 389
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 389
atctgcccct aat 13

<210> SEQ ID NO 390
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 390
agatctgtcc ccta 14

<210> SEQ ID NO 391
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 391
cgggtgctgt tgta 14

<210> SEQ ID NO 392
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 392
atcatgtcga attt 14

<210> SEQ ID NO 393
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 393
ccctggatca tgtc 14

<210> SEQ ID NO 394
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 394
cctttgaatt tgat 14

<210> SEQ ID NO 395
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 395
ttgcggaagc agta 14

<210> SEQ ID NO 396
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 396
gcctgagcag aagt 14

<210> SEQ ID NO 397
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 397
gggggctttc taa 13

<210> SEQ ID NO 398
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 398
agcgctggca acc 13

<210> SEQ ID NO 399
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 399
cccctaatgg ctt 13

<210> SEQ ID NO 400
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 400
tcccctaatg gct 13

<210> SEQ ID NO 401
<211> LENGTH: 13
<212> TYPE: DNA

-continued

```
<213> ORGANISM: Artificial Sequence
<220> FEATURE:
<223> OTHER INFORMATION: modified TGF-beta3 oligonucleotide

<400> SEQUENCE: 401

tcatgtcgaa ttt                                                     13


<210> SEQ ID NO 402
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 402

atcatgtcga att                                                     13
```